United States Patent
Saragosa et al.

(10) Patent No.: US 9,920,841 B2
(45) Date of Patent: Mar. 20, 2018

(54) INTERFACE AND FLUID-TRANSFER SYSTEM

(71) Applicant: EMD Millipore Corporation, Burlington, MA (US)

(72) Inventors: John Saragosa, Melrose, MA (US); John Cieciuch, Dracut, MA (US); James E. Kelly, Melrose, MA (US); Luc Messier, Gloucester, MA (US); Nicholas Vigorito, Stoneham, MA (US)

(73) Assignee: EMD Millipore Corporation, Burlington, MA (US)

( * ) Notice: Subject to any disclaimer, the term of this patent is extended or adjusted under 35 U.S.C. 154(b) by 126 days.

(21) Appl. No.: 14/646,438

(22) PCT Filed: Dec. 16, 2013

(86) PCT No.: PCT/US2013/075460
§ 371 (c)(1),
(2) Date: May 21, 2015

(87) PCT Pub. No.: WO2014/099811
PCT Pub. Date: Jun. 26, 2014

(65) Prior Publication Data
US 2015/0276069 A1    Oct. 1, 2015

Related U.S. Application Data

(60) Provisional application No. 61/738,265, filed on Dec. 17, 2012.

(51) Int. Cl.
*G01N 1/20* (2006.01)
*F16K 3/04* (2006.01)
(Continued)

(52) U.S. Cl.
CPC ............. *F16K 3/04* (2013.01); *G01N 1/10* (2013.01); *G01N 1/22* (2013.01); *G01N 1/2226* (2013.01); *G01N 2001/1037* (2013.01)

(58) Field of Classification Search
CPC ............ F16K 3/04; F16K 15/00; F16K 31/44; G01N 1/10; G01N 1/22; G01N 1/2226;
(Continued)

(56) References Cited

U.S. PATENT DOCUMENTS

| 3,736,099 A | 5/1973 | Begg et al. |
| 3,779,082 A | 12/1973 | Galloway |

(Continued)

FOREIGN PATENT DOCUMENTS

| EP | 0 508 749 A2 | 10/1992 |
| EP | 1 548 420 A2 | 6/2005 |

(Continued)

OTHER PUBLICATIONS

International Search Report and the Written Opinion for International Application No. PCT/US2013/075460, entitled "Interface and Fluid-Transfer System"; dated Mar. 4, 2014.

(Continued)

*Primary Examiner* — Harshad R Patel
*Assistant Examiner* — Octavia Hollington
(74) *Attorney, Agent, or Firm* — Hamilton, Brook, Smith & Reynolds, P.C.

(57) ABSTRACT

A fluid transfer system (100) includes a transfer device (104) and an interface device (102). The transfer device (104) includes a fluid transfer member (164) and a transfer coupling member (125) to align the fluid transfer member (164) with the interface device (102). The interface device (102) includes a reservoir port (108), a fluid transfer member receptacle (144), an interface coupling member (124), and a reservoir valve (110). The interface coupling member (124)

(Continued)

is configured to close the fluid transfer member receptacle (144) and to couple to the transfer coupling member (125) and open the fluid transfer member receptacle (144) to receive the fluid transfer member (164). The reservoir valve (110), e.g., a sliding seal, is configured to close the reservoir port (108) from the fluid transfer member receptacle (144) and to open the reservoir port (108) to the fluid transfer member (164) when the fluid transfer member (164) is positioned in the fluid transfer member receptacle (144). The fluid transfer member (164) can include a plunger assembly configured to open and close the reservoir port (108).

6 Claims, 45 Drawing Sheets

(51) Int. Cl.
    *G01N 1/10*         (2006.01)
    *G01N 1/22*         (2006.01)

(58) Field of Classification Search
    CPC .......... G01N 1/20; G01N 1/2035; A61B 5/00; A61B 19/00; A61M 39/00; A61M 39/10; A61M 39/16
    USPC ............................................. 73/863, 863.84
    See application file for complete search history.

(56) References Cited

U.S. PATENT DOCUMENTS

| | | | |
|---|---|---|---|
| 4,306,705 | A | 12/1981 | Svensson |
| 4,941,517 | A | 7/1990 | Galloway |
| 5,535,635 | A | 7/1996 | Shaw |
| 5,549,568 | A | 8/1996 | Shields |
| 5,658,256 | A | 8/1997 | Shields |
| 5,885,255 | A | 3/1999 | Jaeger, Jr. et al. |
| 6,032,543 | A | 3/2000 | Årthun et al. |
| 6,516,677 | B1 | 2/2003 | Suter |
| 7,137,974 | B2 | 11/2006 | Almasian et al. |
| 7,293,475 | B2 | 11/2007 | Furey et al. |
| 7,293,477 | B2 | 11/2007 | Furey et al. |
| 7,658,201 | B2 | 2/2010 | Salomon |
| 7,832,293 | B2 | 11/2010 | Hermet et al. |
| 7,921,740 | B2 | 4/2011 | Furey et al. |
| 7,927,316 | B2 | 4/2011 | Proulx et al. |
| 8,029,023 | B2 | 10/2011 | Årthun et al. |
| 8,517,998 | B2 | 8/2013 | Proulx et al. |
| 8,522,832 | B2 * | 9/2013 | Lopez ................... A61J 1/2096 141/27 |
| 8,539,988 | B2 | 9/2013 | Guedon |
| 8,544,497 | B2 * | 10/2013 | Hillier ...................... F16K 1/12 137/542 |
| 8,549,935 | B2 | 10/2013 | Furey et al. |
| 8,562,572 | B2 | 10/2013 | Proulx et al. |
| 8,579,871 | B2 | 11/2013 | Proulx et al. |
| 8,646,342 | B2 | 2/2014 | Furey et al. |
| 8,690,120 | B2 | 4/2014 | Hartnett et al. |
| 9,028,779 | B2 | 5/2015 | Olivier |
| 9,482,351 | B2 * | 11/2016 | Proulx .................. A61M 39/10 |
| 2004/0186432 | A1 * | 9/2004 | Barry ...................... A61M 5/30 604/152 |
| 2008/0087860 | A1 | 4/2008 | Vaillancourt et al. |
| 2009/0229671 | A1 | 9/2009 | Hartnett et al. |
| 2010/0123094 | A1 | 5/2010 | Zumbrum |
| 2010/0133459 | A1 | 6/2010 | Zumbrum |
| 2010/0154569 | A1 | 6/2010 | Guedon |
| 2010/0158759 | A1 | 6/2010 | Olivier |
| 2010/0301060 | A1 | 12/2010 | Bernard et al. |
| 2011/0155258 | A1 | 6/2011 | Zumbrum |
| 2013/0334450 | A1 | 12/2013 | Proulx et al. |

FOREIGN PATENT DOCUMENTS

| | | |
|---|---|---|
| EP | 1 729 106 A2 | 12/2006 |
| JP | H 04-120358 | 10/1992 |
| JP | 2005-181336 | 7/2005 |
| WO | WO 2007/143426 A2 | 12/2007 |
| WO | WO 2009/071829 A2 | 6/2009 |
| WO | WO 2010/112081 A1 | 10/2010 |
| WO | WO 2011/137437 A2 | 11/2011 |
| WO | WO 2012/114105 A1 | 8/2012 |
| WO | WO 2013/011231 A1 | 1/2013 |

OTHER PUBLICATIONS

Vanasyl LLC., The Vanasyl Sampling System: The Vanasyl Sampling Valve and Vanasyl Sampling Bags. Informative Documentation, downloaded from internet Sep. 18, 2012 http://www.vanasyl.com/home/html, 8 pages.
IPRP for International Application No. PCT/US2013/075460, entitled "Interface and Fluid-Transfer System"; dated Jun. 23, 2015.
AllPure Takeone Aseptic Sampling System Overview, 2010, 2 pages.
ASI Life Sciences, three 60, Single Use Aseptic Sampling System, www.asisus.com, Jan. 10, 2013, 8 pages.
Gore Single-Use Valve, for Steam-In-Place Applications, 2009, 4 pages.
Gore STA-Pure Fluid Sampling System, for Single-Use Aseptic Applications, Secure Sampling for Bioprocessing Fluids, Dec. 2008, 4 pages.
Sterisart® NF—gamma Septum 16476 System with Short Dual-Needle Metal Spike, "Sartorius Stedim Biotech GmbH", Publication No. S-2077-e11082, Ver. Aug. 2011.

* cited by examiner

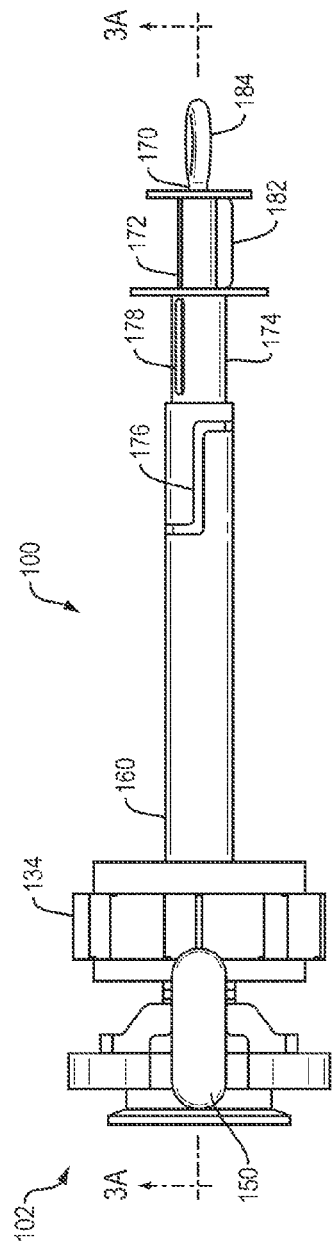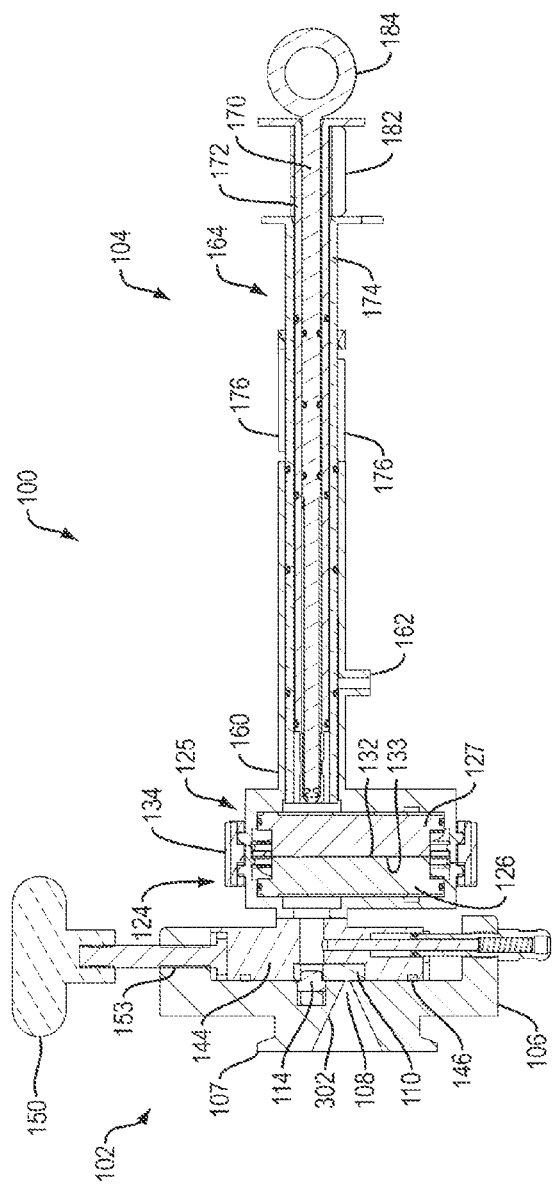

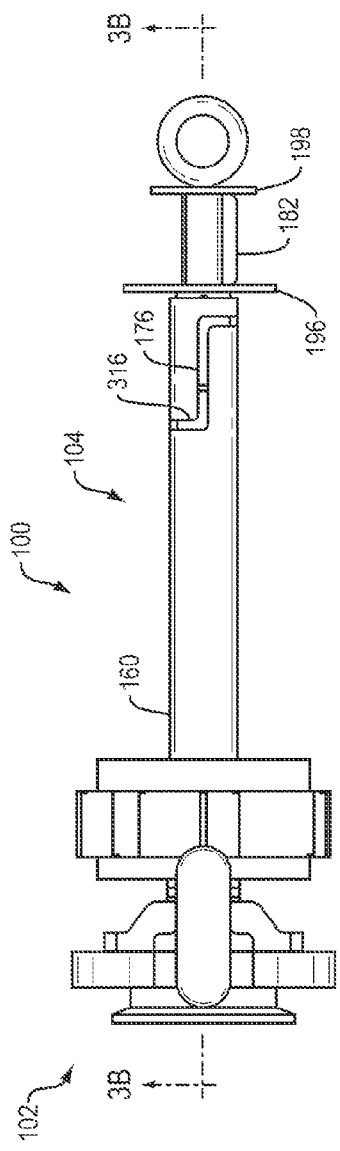
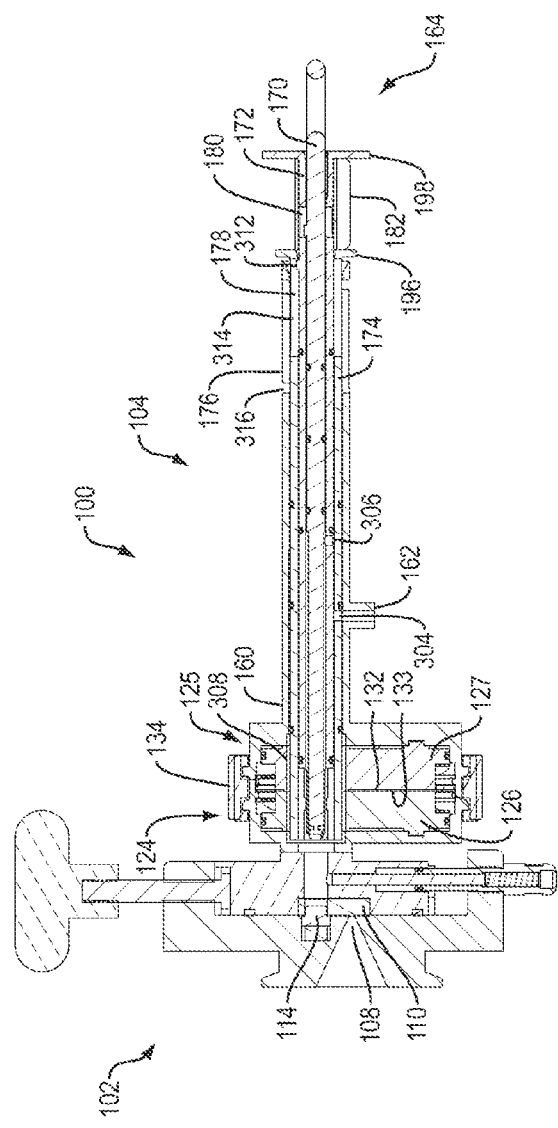

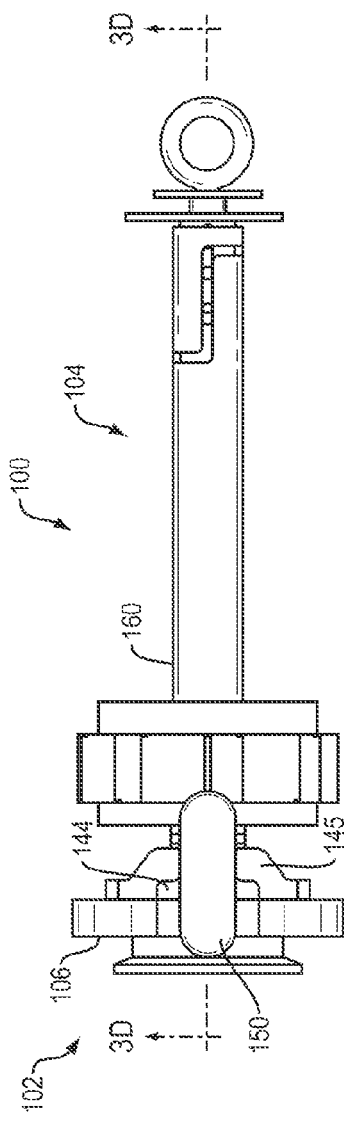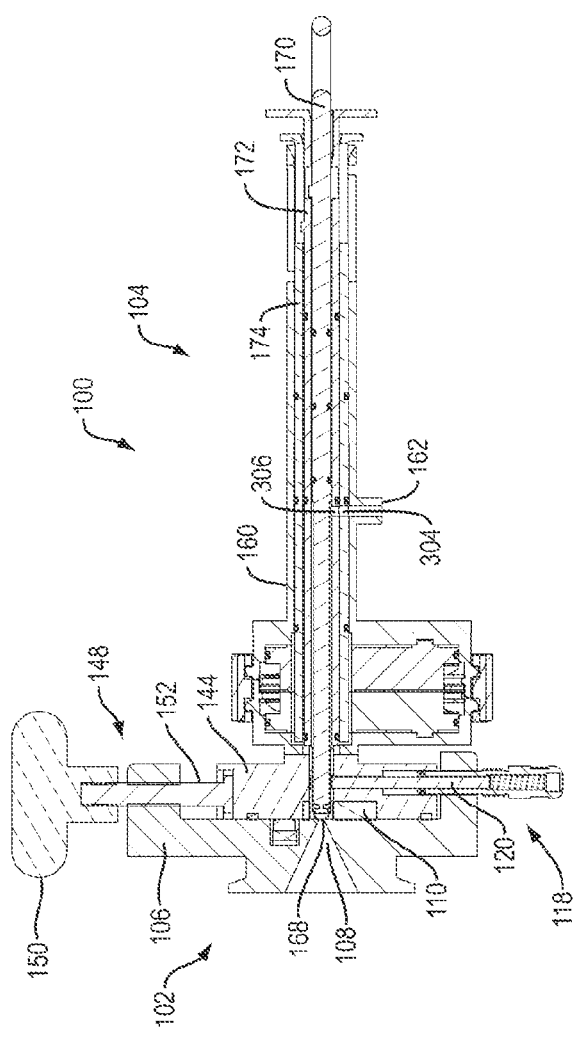
FIG. 2D
FIG. 3D

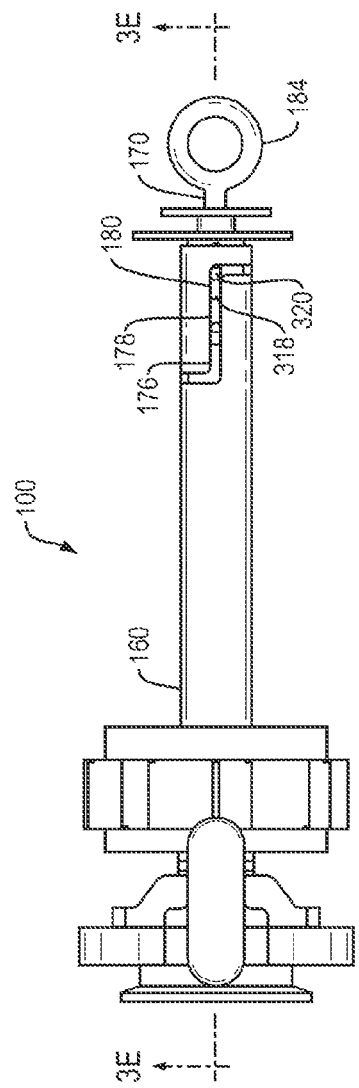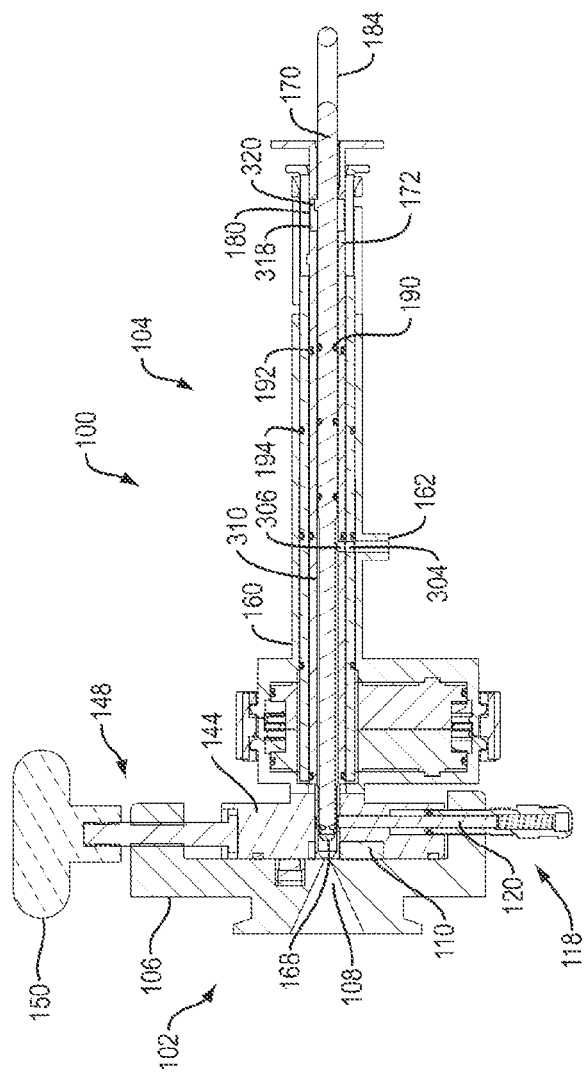

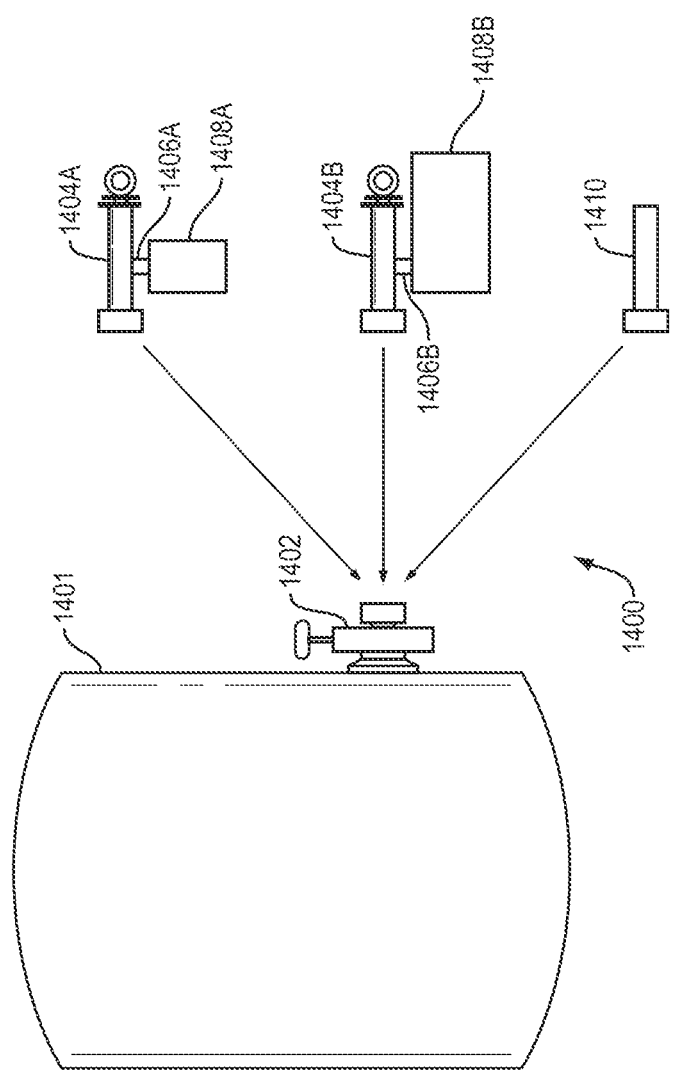

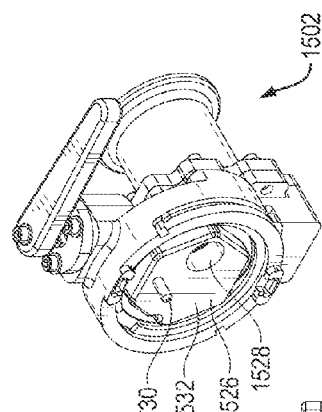
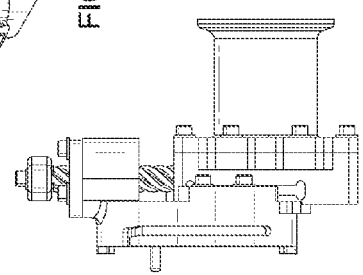
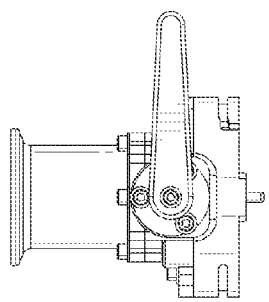
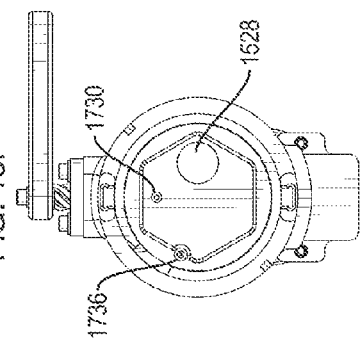
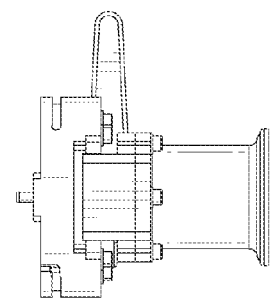
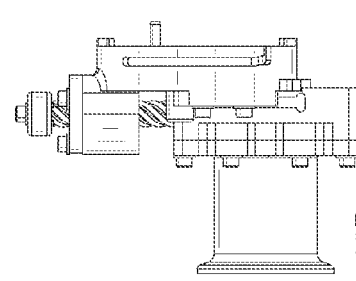
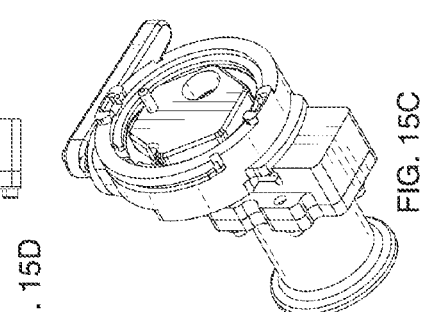

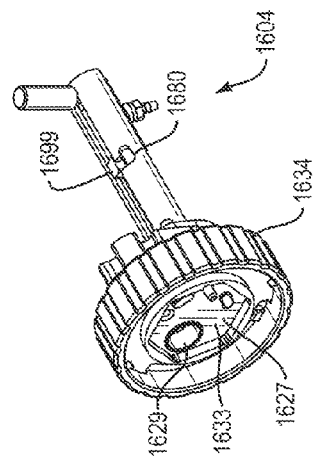
FIG. 16B
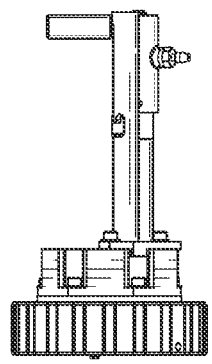
FIG. 16E
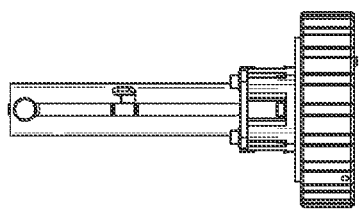
FIG. 16F  FIG. 16H  FIG. 16G
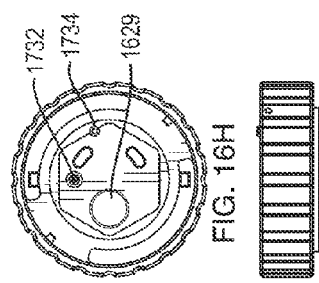
FIG. 16D  FIG. 16C
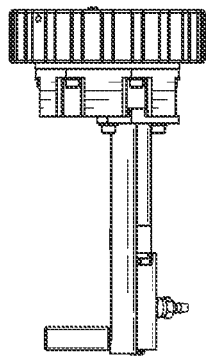
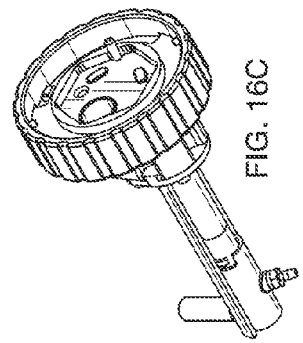

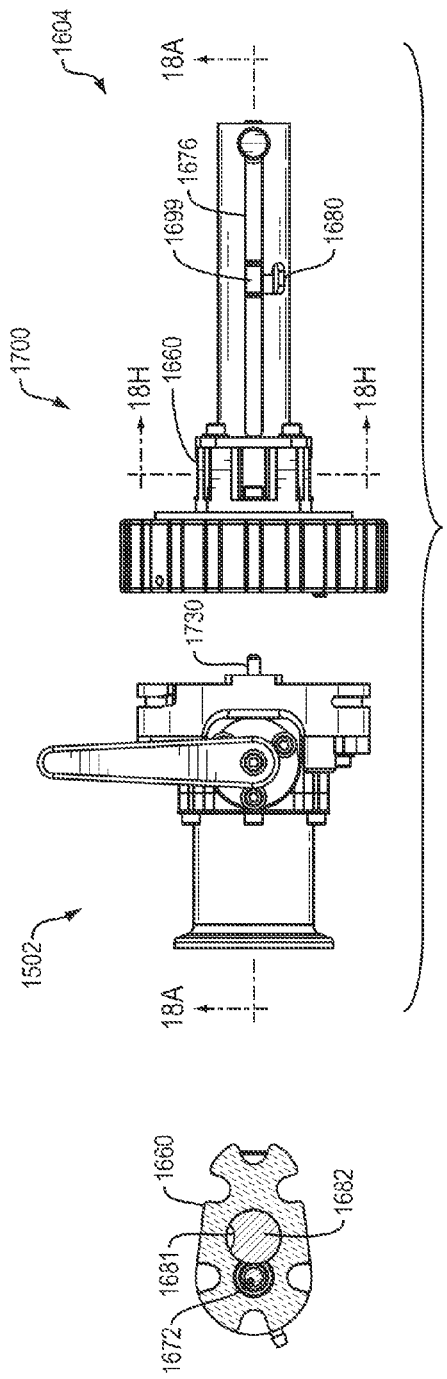
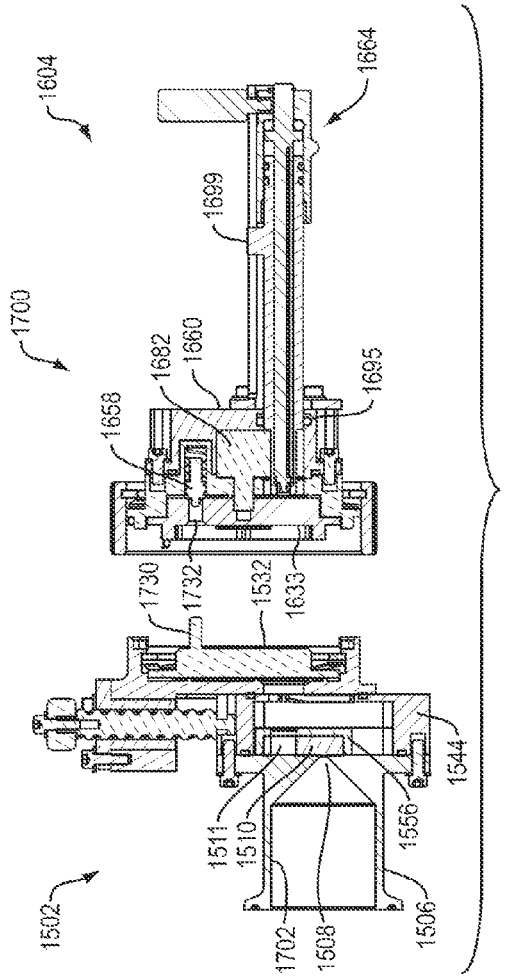

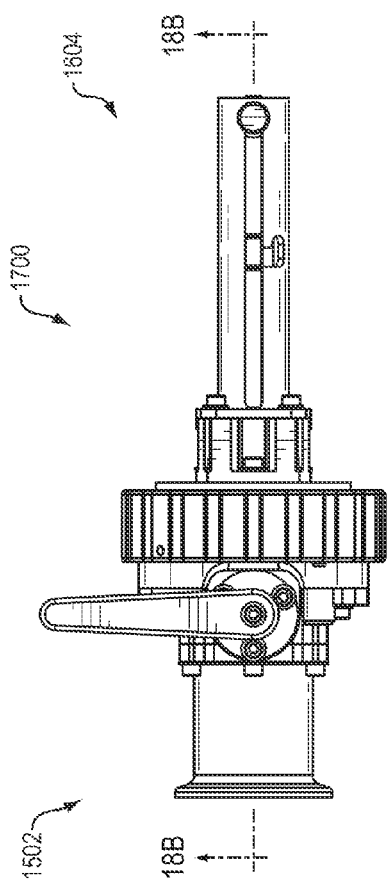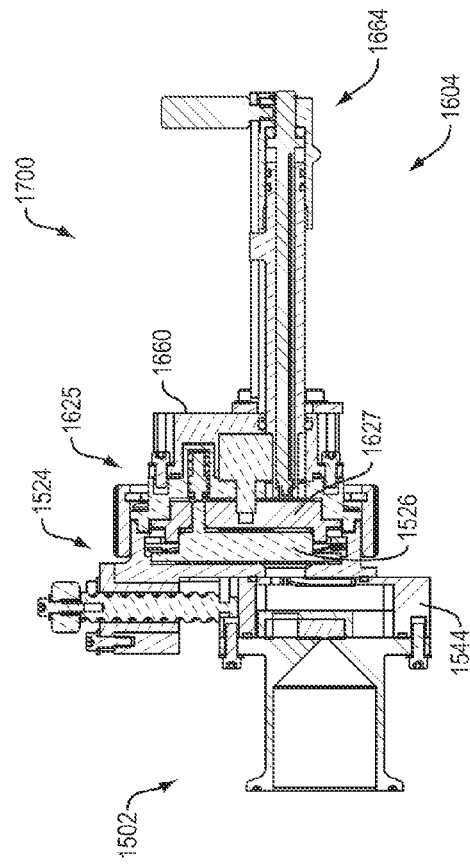

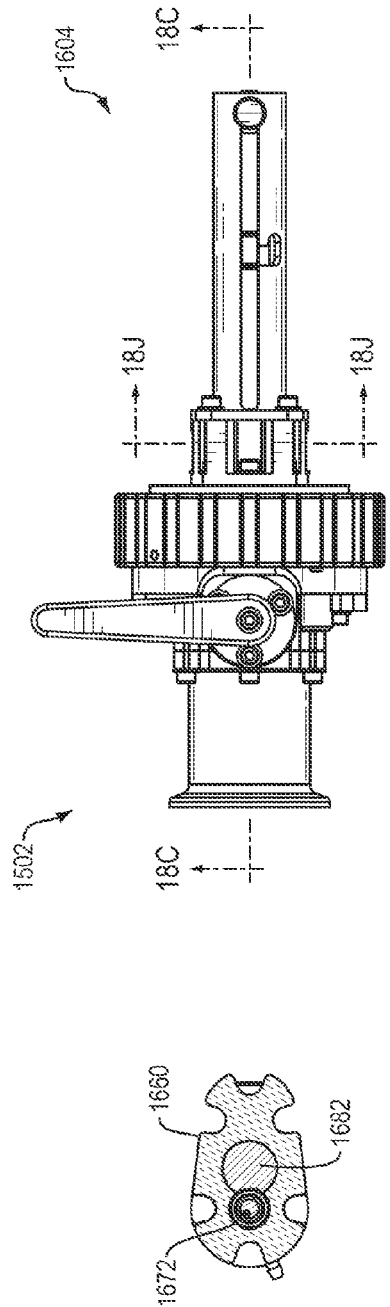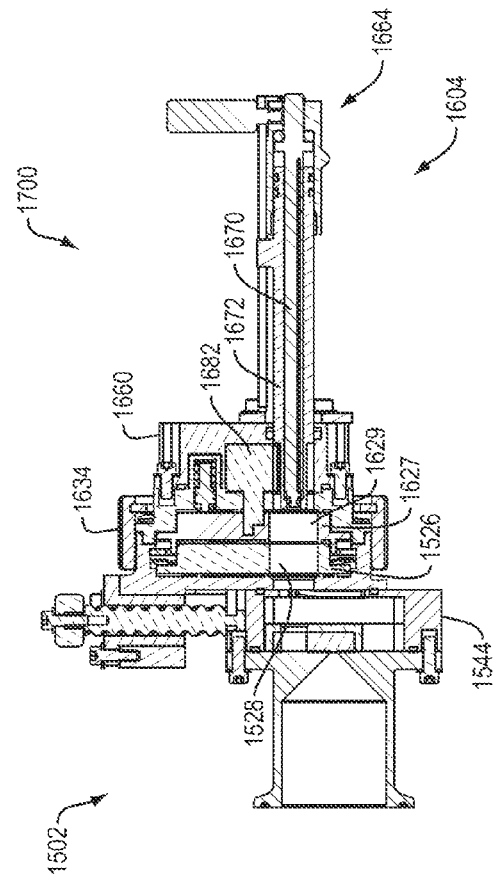

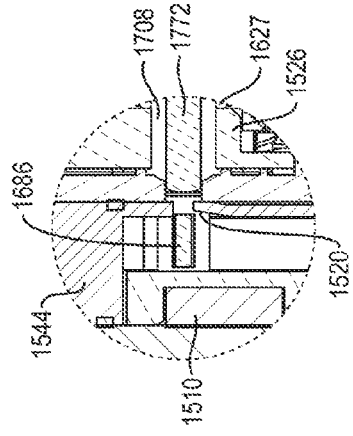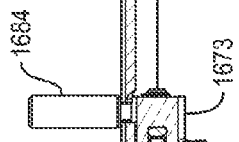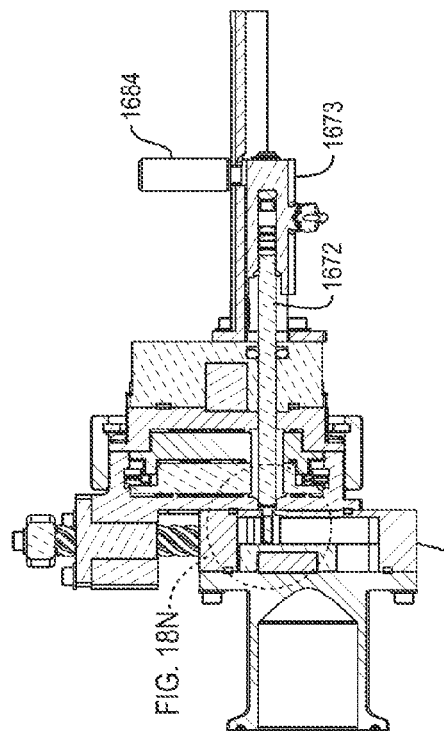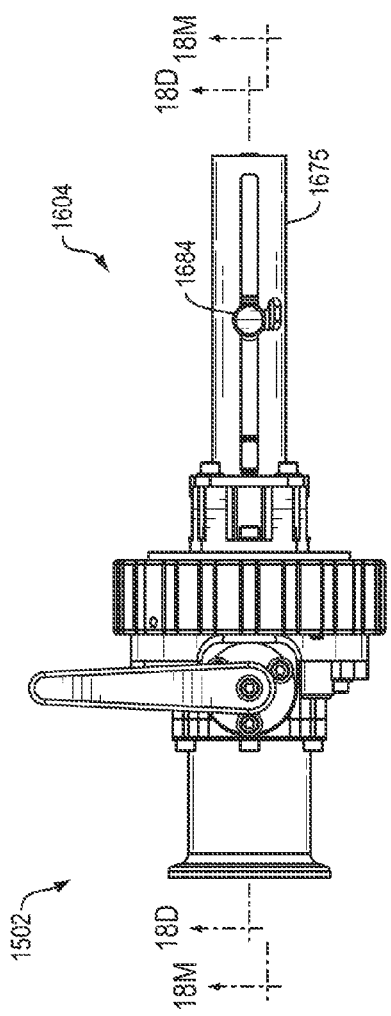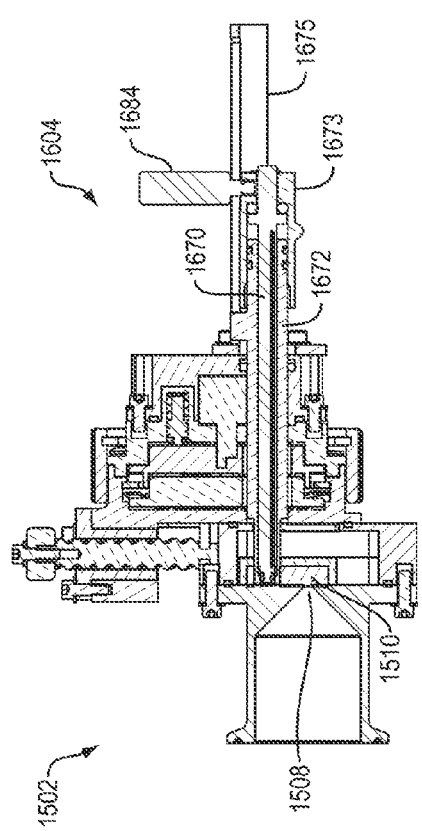

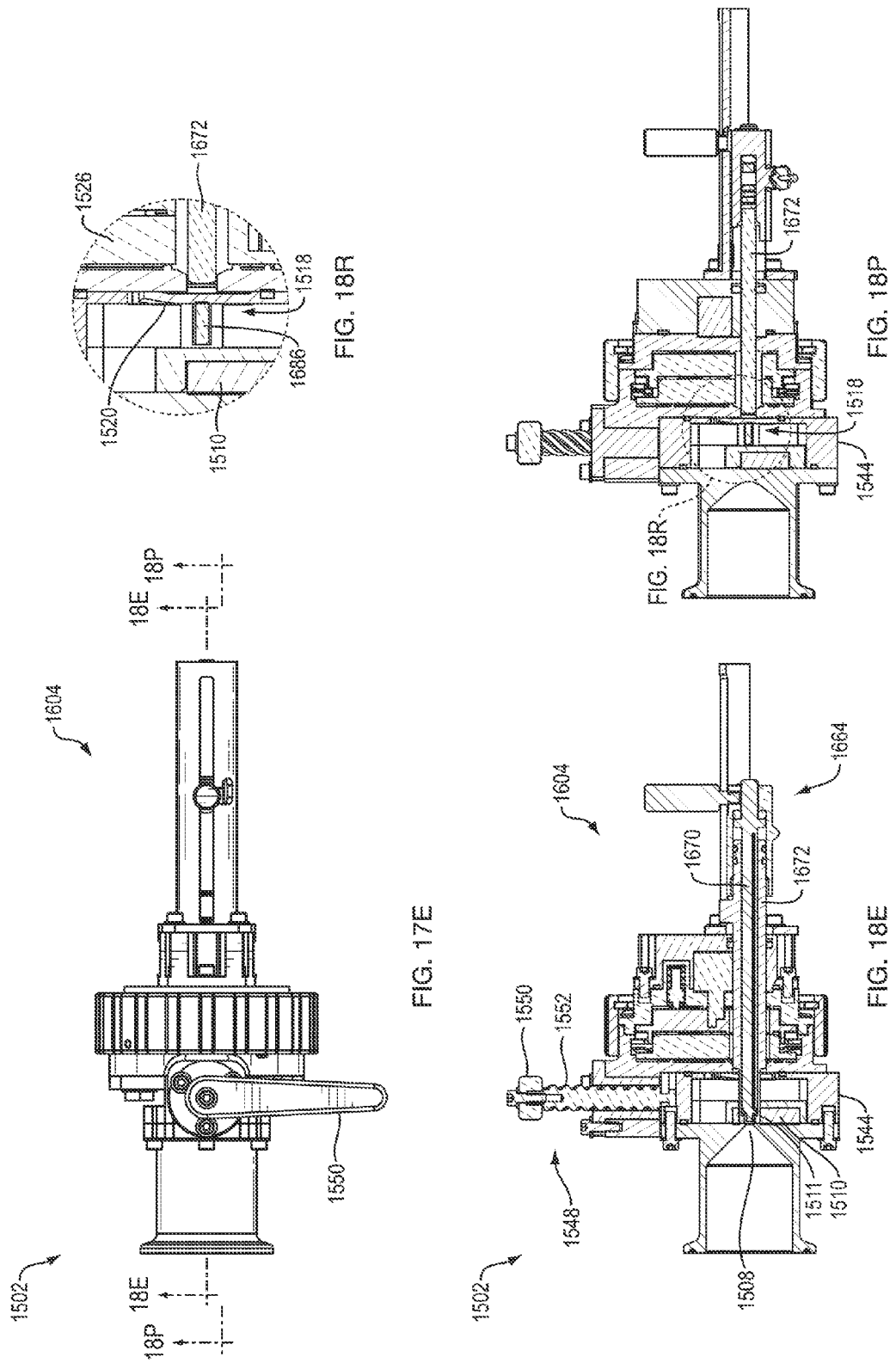

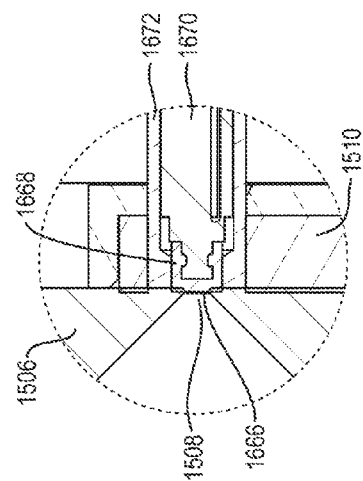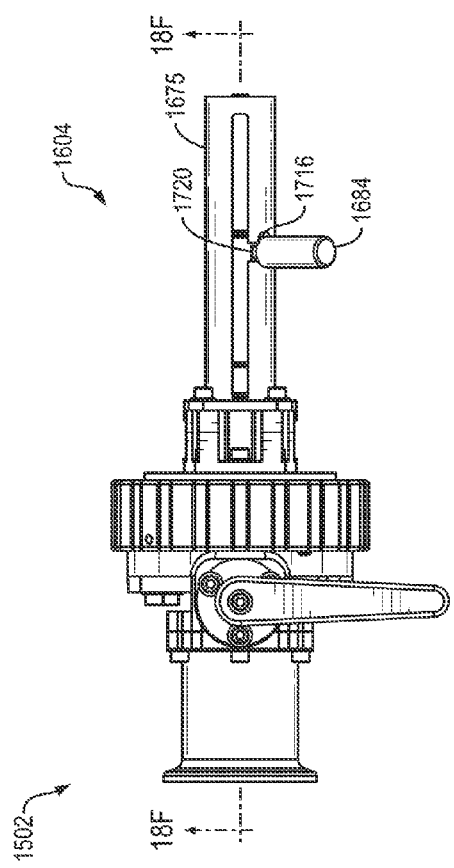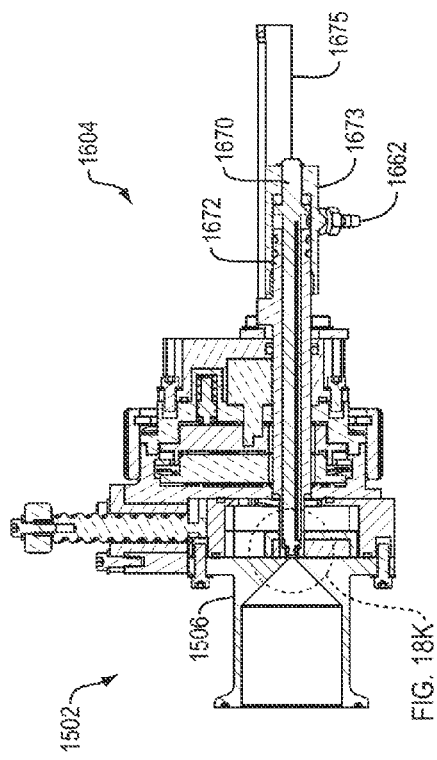

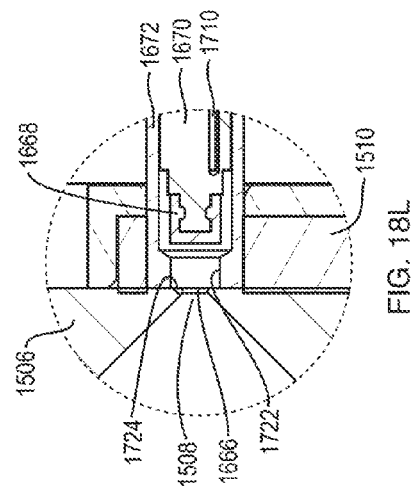
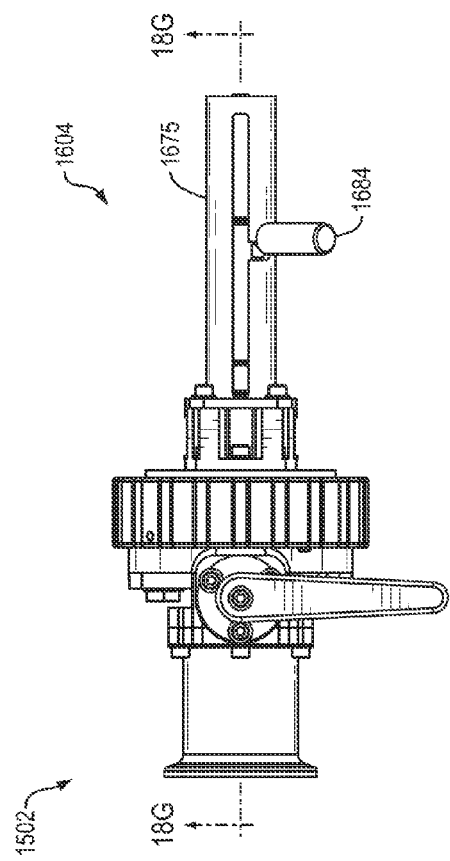
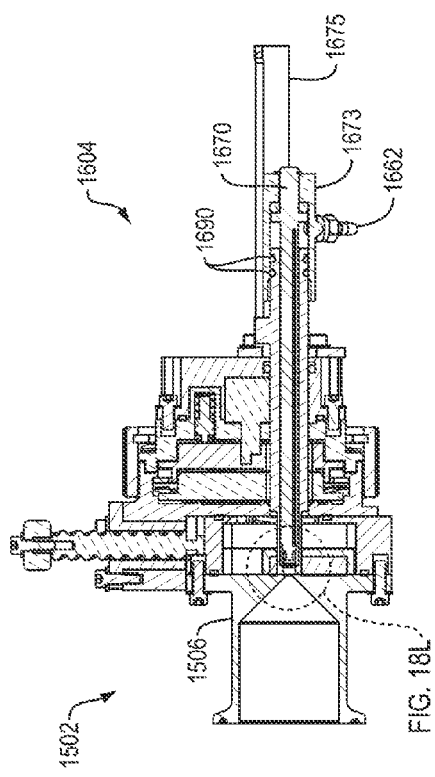

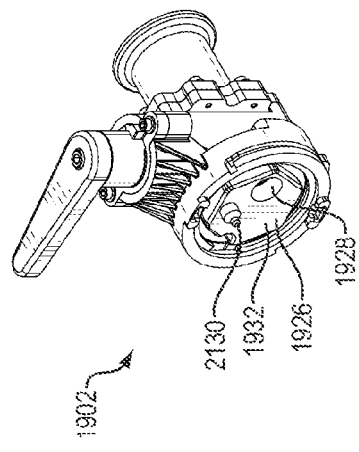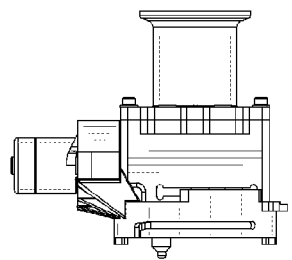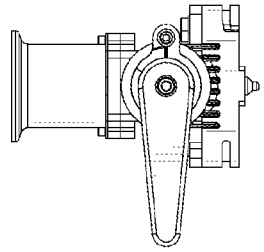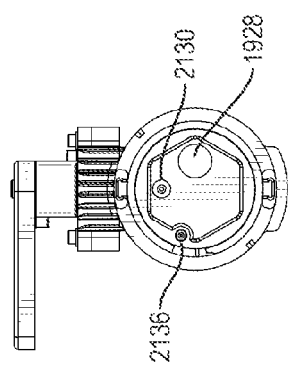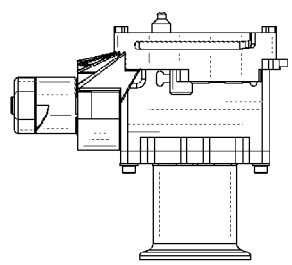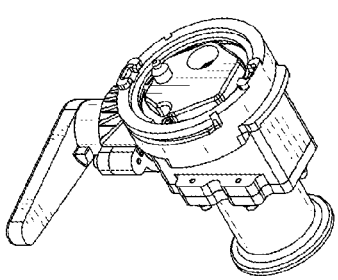

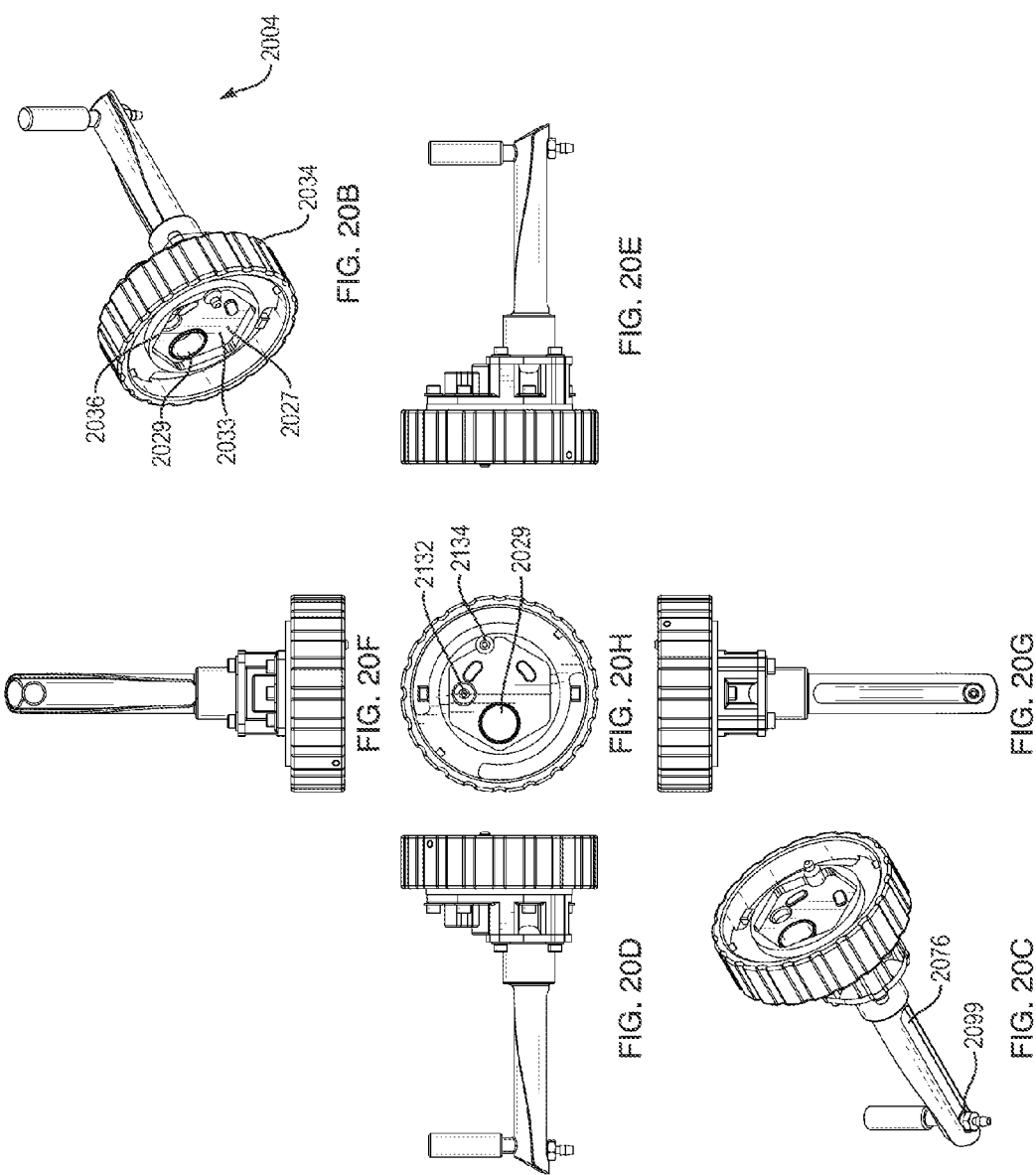

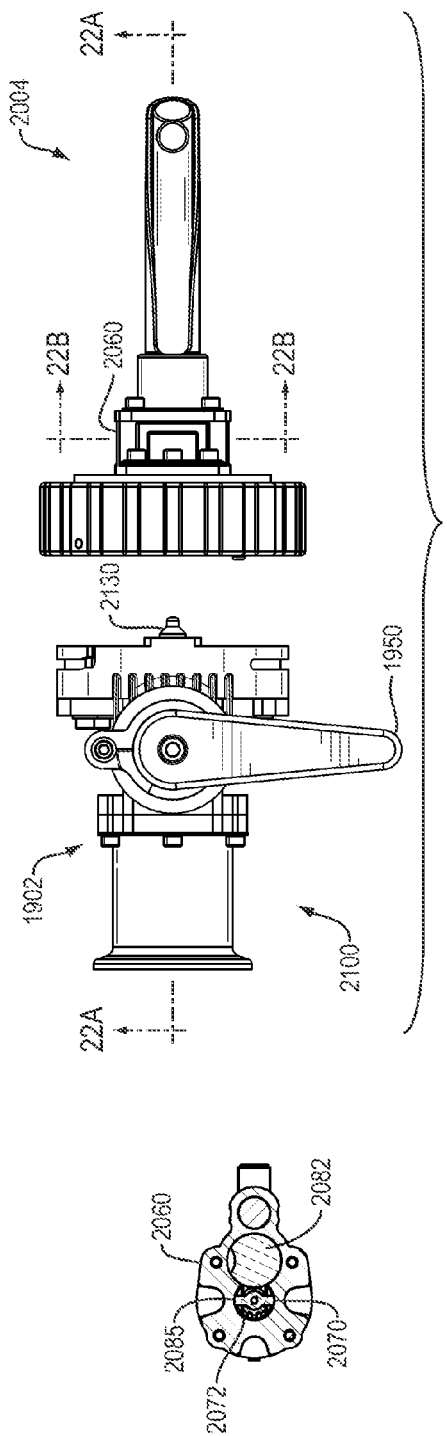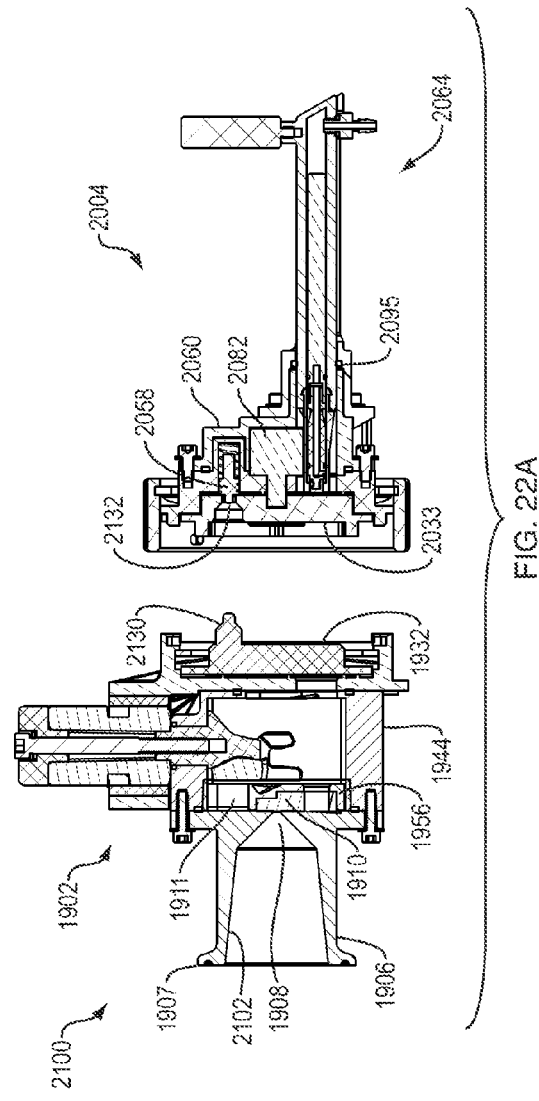

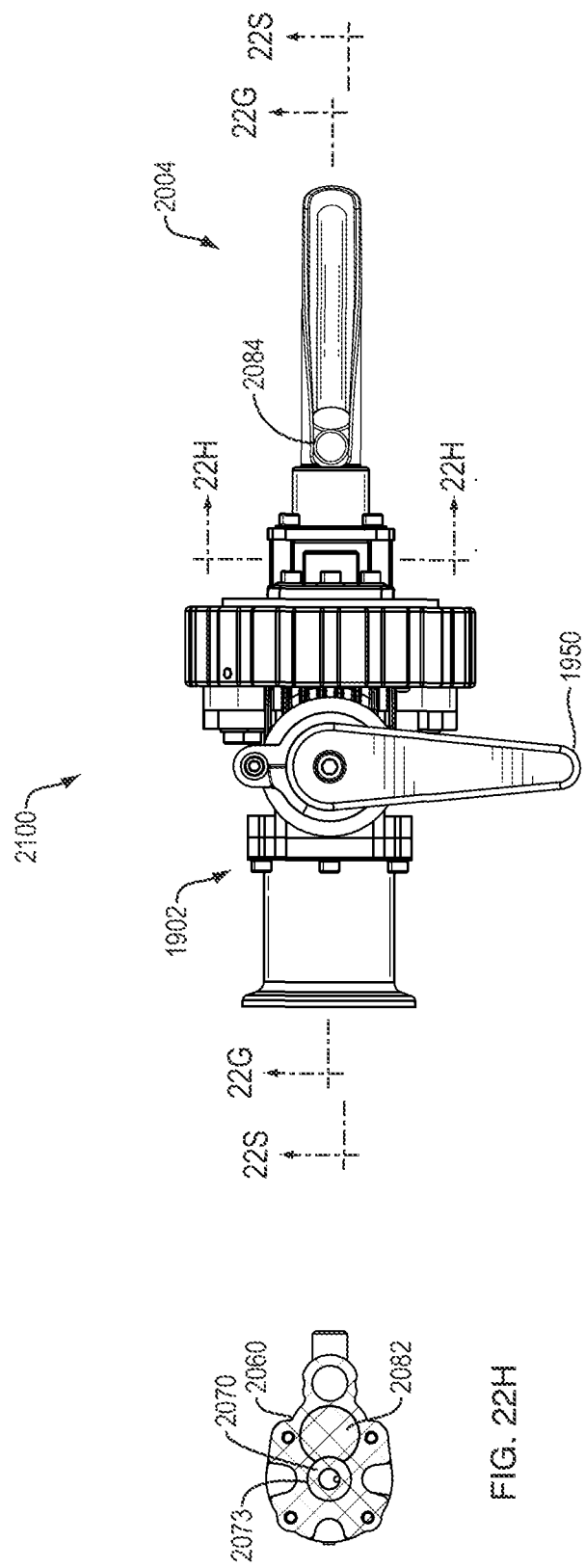

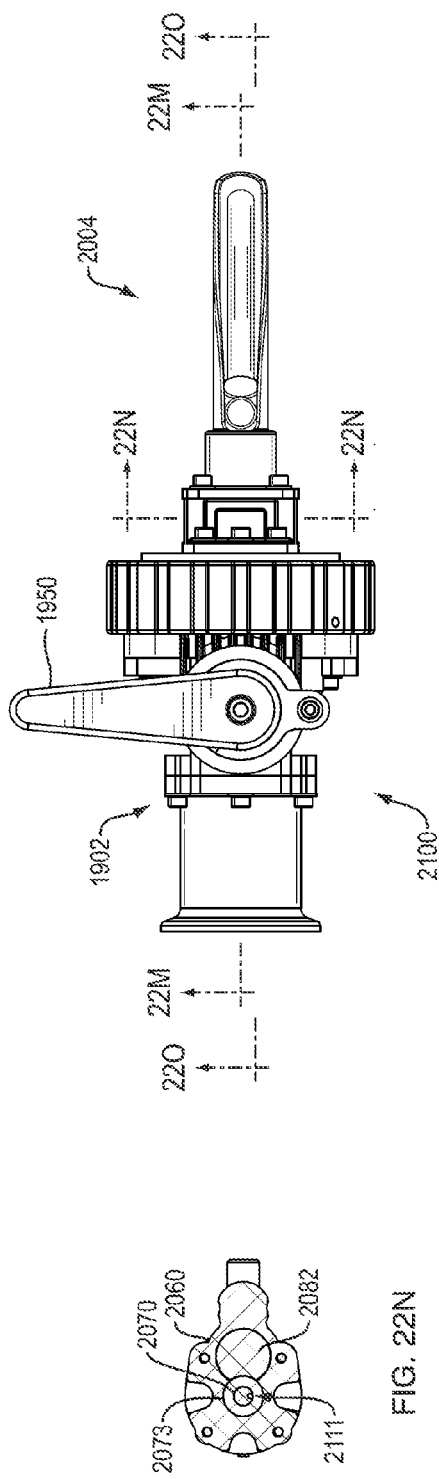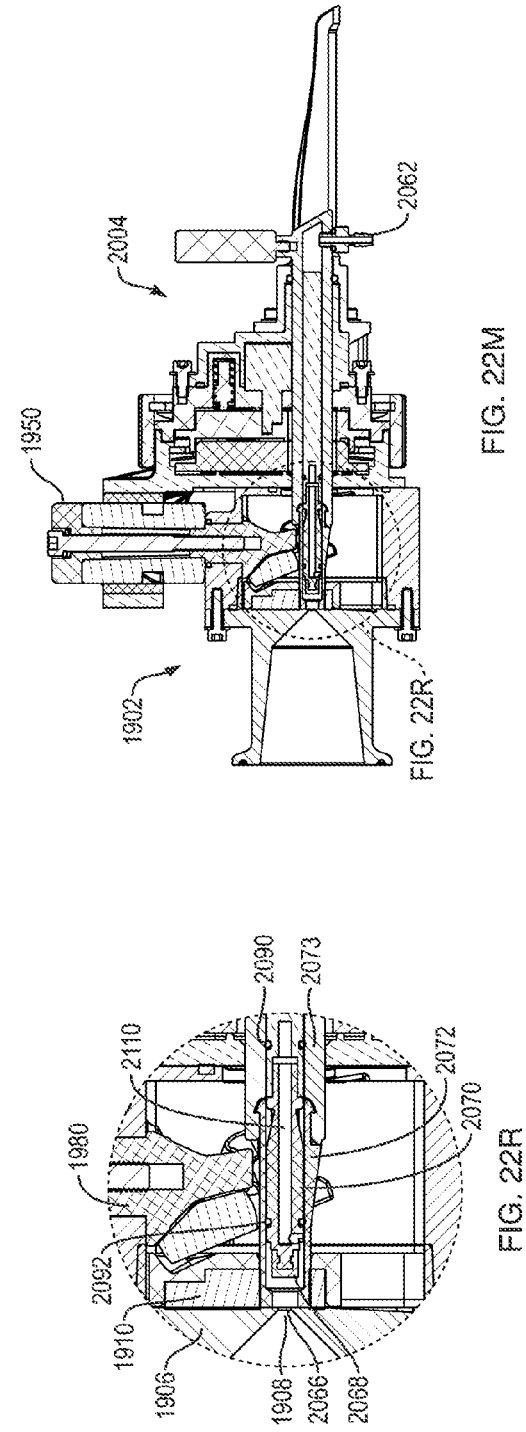

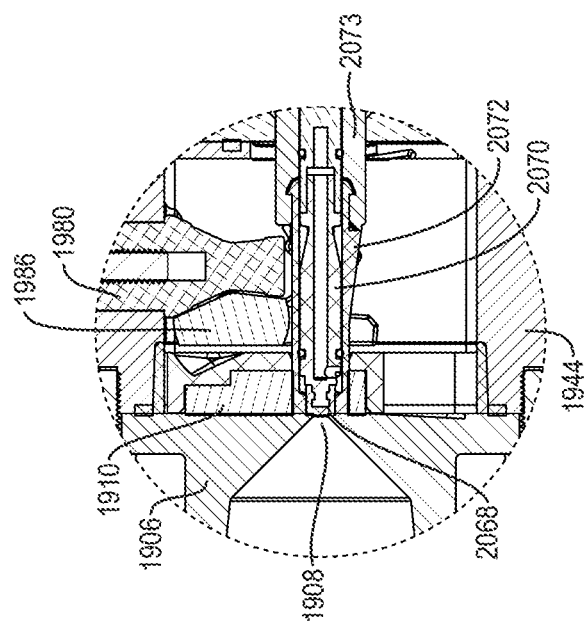
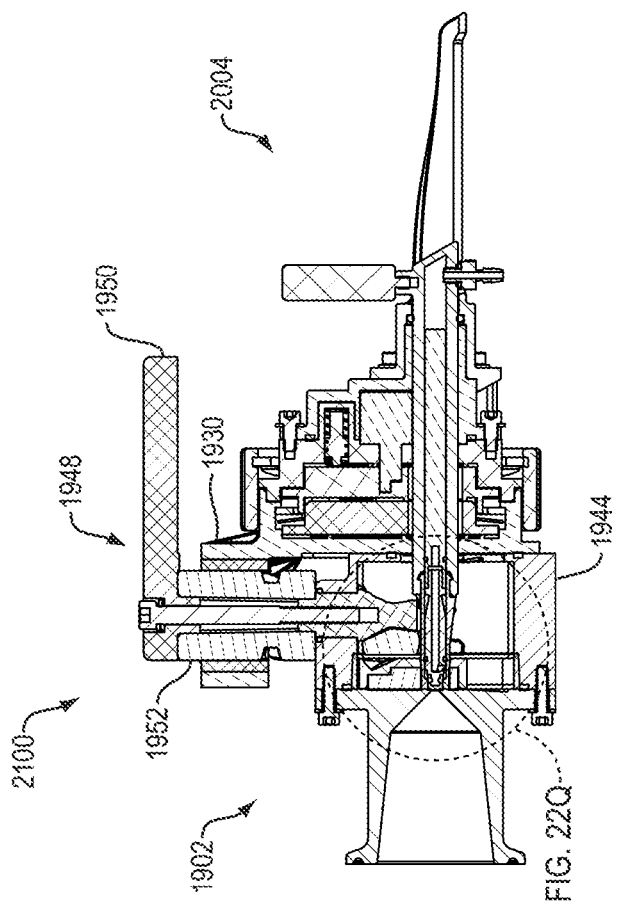

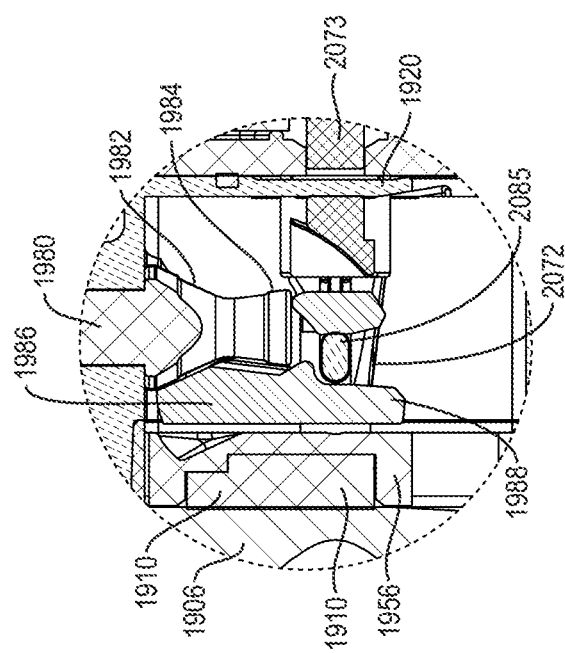
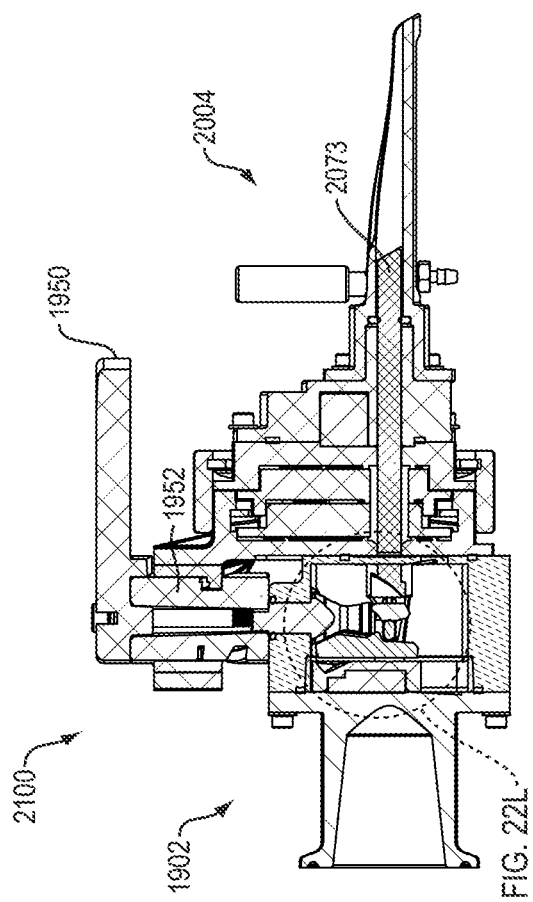
FIG. 22L
FIG. 22K

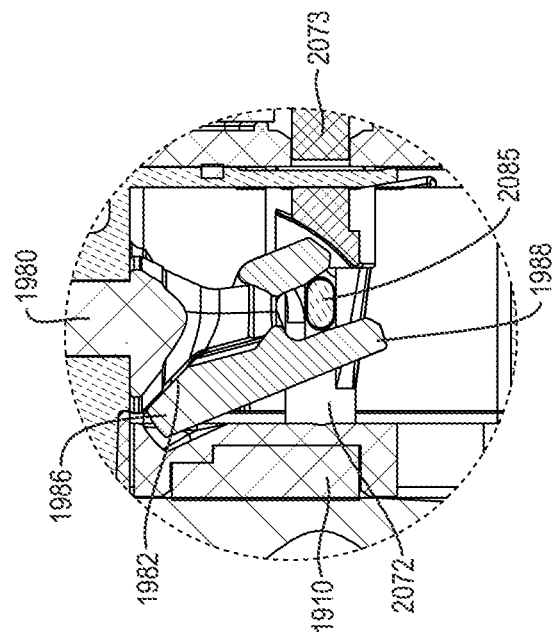
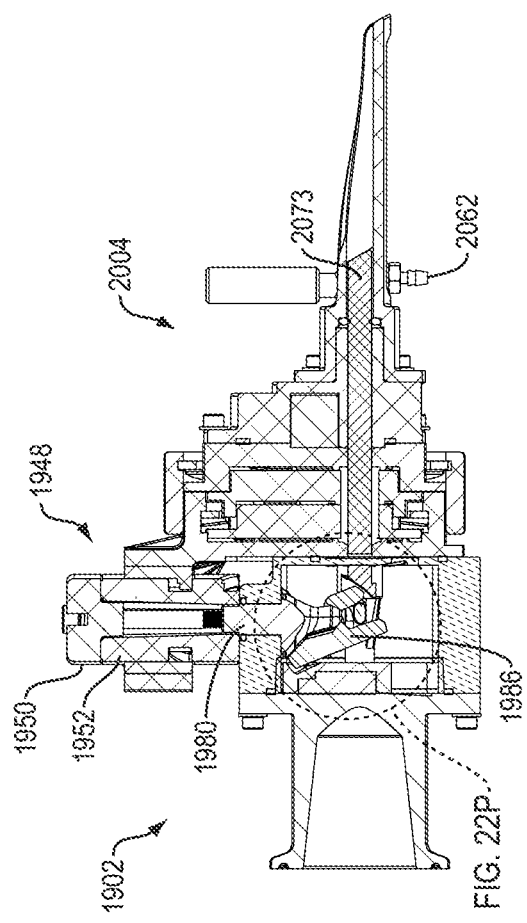

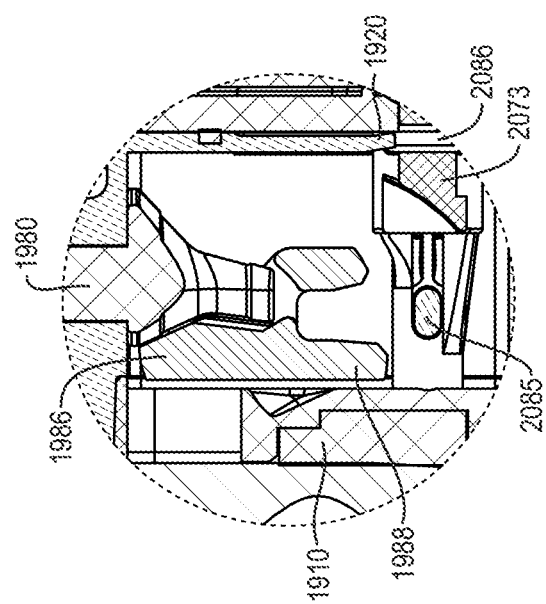
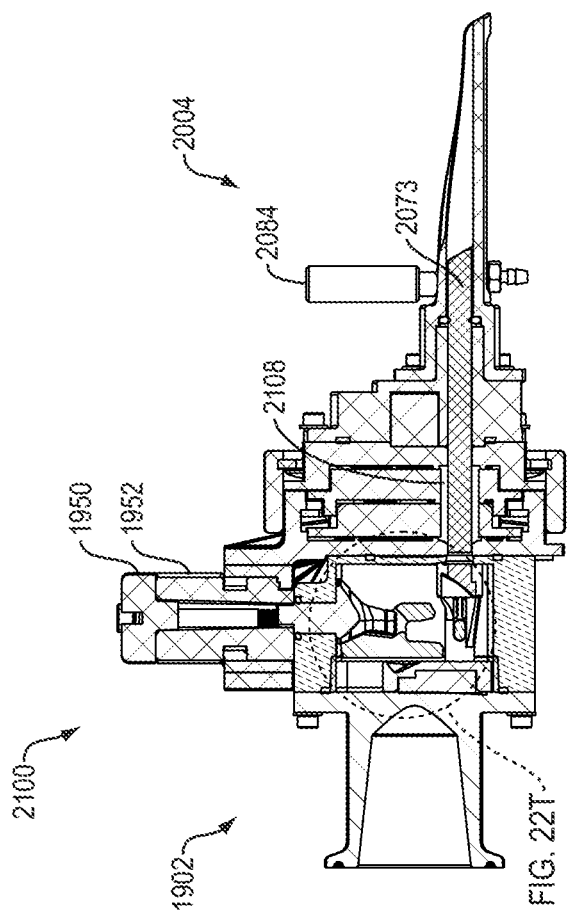

INTERFACE AND FLUID-TRANSFER SYSTEM

RELATED APPLICATION

This application is the U.S. National Stage of International Application No. PCT/US2013/075460, filed on Dec. 16, 2013, which designates the U.S., published in English, and claims the benefit of U.S. Provisional Application No. 61/738,265 filed on Dec. 17, 2012. The entire teachings of the above applications are incorporated herein by reference.

BACKGROUND OF THE INVENTION

There are many aseptic and sterile sampling systems on the market today. Often, the sampling systems connect to a vessel via a sanitary connection (typically, a standard port of 0.75", 1.5" or 2" in diameter). Some systems are actuated by a valve mechanism while others employ a needle to pierce a septum. In general, the number of samples that can be taken may be limited by any of the following aspects: size of the septum (piercing multiple times at one site is generally not accepted in the industry), size and number of the containers (bags, bottles, etc.) that can be attached to the vessel, and size (diameter) of the tubing attached to the sanitary connection. When higher numbers of samples (e.g., more than 10 samples) for a particular process are required, the sampling systems can be attached via manifolds. Attaching via manifolds, however, creates a hold-up volume (also referred to as deadleg), which is undesirable, and requires a flushing step, which can add cost and complexity to the given process.

A drawback of many current sampling systems is that they require excessive handling, as all single-use sampling containers must be pre-attached at once and prior to the start of a process.

SUMMARY OF THE INVENTION

The present invention relates to a system and corresponding method for transfer of fluids, be they liquids or gases. The present invention provides an interface device and a transfer device that can be used in a processing system, such as a traditional steel system, e.g., a tank or piping, or a disposable system, e.g., a bioreactor bag. The interface device may provide both a means for steam sterilizing in place, also referred to as 'steam in place' (SIP), or cleaning in place (CIP), e.g., with chemical agents, the mating point of the interface device to the processing system and means for forming a sterile connection to the transfer device. The transfer device is selectively coupled to the interface device and may provide a pre-sterilized downstream area or component that can be disposed of after use and not be cleaned. When coupled or decoupled, the interface device and transfer device are each closed to the external environment.

Example embodiments of the invention are capable of handling fluids in a sterile manner, such as may be required for pharmaceutical, biotechnology and food, beverage and cosmetics industries. Sterile fluid transfer is designed to prevent unwanted, often dangerous organisms, such as bacteria, as well as environmental contaminants, such as dust, dirt and the like, from entering into a fluid reservoir, e.g., piping in a process stream or a tank holding an end product. Embodiments of the invention can be used to withdraw samples from the reservoir to check for microbial contamination, e.g., for quality control or process control, to transfer materials to or from the reservoir in order to add components of a product, such as media or buffers to a bioreactor, and, more generally, to provide a means of access to the contents of reservoir, such as to introduce a probe or a sensor.

A fluid transfer system according to an example embodiment of the present invention includes an interface device to be fixed to a reservoir and a transfer device to be selectively coupled to the interface device. The transfer device includes a fluid transfer member and a transfer coupling member to align the fluid transfer member with the interface device. The interface device includes a reservoir port, a fluid transfer member receptacle, an interface coupling member, and a reservoir valve. The interface coupling member is configured to close the fluid transfer member receptacle and to couple to the transfer coupling member and open the fluid transfer member receptacle to receive the fluid transfer member. The reservoir valve is configured to close the reservoir port from the fluid transfer member receptacle and to open the reservoir port to the fluid transfer member only when the fluid transfer member is positioned in the fluid transfer member receptacle.

The fluid transfer system can include a transfer member locking element to retain the transfer member in position in the fluid transfer member receptacle when the reservoir port is open.

In an embodiment, the fluid transfer member includes a plunger assembly configured to open and close the reservoir port of the interface device. The reservoir valve of the interface device can include a sliding seal, for example, a sliding seal that slides linearly. Also included can be a seal locking element to retain the sliding seal in position to close the reservoir port until released by the plunger assembly.

The coupling members can include respective sliding elements having respective openings to receive the fluid transfer member. The sliding elements can be discs and can be configured for rotation to bring the openings into alignment with the fluid transfer member. The discs can include respective mating faces configured to rotationally couple the discs. Also included may be a collar to rotate the discs into alignment with the fluid transfer member and to lock the coupling members together with rotation of the collar. In an embodiment, the plunger assembly comprises an intermediate plunger slidably disposed in an outer plunger, the outer plunger configured to extend through the openings of the sliding elements, e.g., discs, to prevent contact of the intermediate plunger with the coupling members. The plunger assembly may further include an inner plunger slidably disposed in the intermediate plunger. The inner, outer, and intermediate plungers cooperate to provide a fluid path from the reservoir port to a transfer port.

The transfer device can include an interlock configured for rotation with the disc of the transfer coupling member, the interlock preventing the transfer member from extending toward the transfer coupling member until the opening in the disc is aligned with the bore of the body of the transfer device. The transfer member can be configured to maintain a gap between the transfer member and the disc of the coupling member when the transfer member extends through the coupling member.

The interface device may include a reservoir port and a sliding seal having a hole therethrough, the hole initially being out of alignment with the reservoir port to close the reservoir port. Further, the device may include a seal locking element retaining the sliding seal in position to close the reservoir port. The transfer device may have a plunger therein that extends through the sliding seal, e.g., to release a seal locking element. The sliding seal is thereafter slidable to align the hole and plunger with the reservoir port. The plunger is configured to seal the reservoir port or to open the reservoir port to provide a fluid path from the reservoir port to a transfer port. The plunger may be configured to move the sliding seal to open or close the reservoir port.

The interface device can include an actuating mechanism to move the reservoir valve, e.g., the sliding seal. In an embodiment, the actuating mechanism includes an axial cam to cause vertical movement of the reservoir valve with a first rotary motion of the actuating mechanism. The first rotary motion causes movement of the reservoir valve only when the transfer member, e.g., the plunger, is positioned in the transfer member receptacle. The actuating mechanism can further include a rotary cam to cause horizontal movement with a second rotary motion of the actuating mechanism. The horizontal movement causes movement of a valve of the transfer member to control flow of fluid, e.g., from the reservoir port to the transfer port.

A method of transferring fluid according to an example embodiment of the present invention includes providing an interface device including a reservoir port, a reservoir valve, and a fluid transfer member receptacle. The method further includes aligning a fluid transfer member of a transfer device with the interface device, opening the fluid transfer member receptacle to receive the fluid transfer member, and, with the fluid transfer member positioned in the fluid transfer member receptacle, actuating the reservoir valve to open the reservoir port to the fluid transfer member.

The method of transferring fluid may include actuating the reservoir valve to close the reservoir port from the fluid transfer receptacle, and may further include withdrawing the fluid transfer member from the fluid transfer member receptacle and closing the fluid transfer member receptacle. The reservoir valve can comprise a sliding seal, and actuating the valve can include sliding the sliding seal linearly. The method may further include with a seal locking element, retaining the sliding seal in position to close the reservoir port until the seal locking element is released. For example, the sliding seal may have a hole therethrough, and the method may include extending the fluid transfer member through the hole to release the seal locking element. In an embodiment, actuating the reservoir valve includes sliding the sliding seal to align the hole and transfer member with the reservoir port. Actuating the reservoir valve can include actuating the reservoir valve with movement of the fluid transfer member.

Further, the method of transferring fluid can include coupling a transfer coupling member of the transfer device to an interface coupling member of the interface device. The coupling members can include respective discs having respective openings to receive the transfer member. Opening the fluid transfer member receptacle can include causing rotation of the discs to bring the openings into alignment with the fluid transfer member. The method may further include rotationally coupling the discs.

In an embodiment, the method further includes, with a transfer member locking element, retaining the transfer member in position in the fluid transfer member receptacle when the reservoir port is open.

A method of transferring fluid according to an example embodiment of the present invention includes providing an interface device that includes a reservoir port and a sliding seal having a hole therethrough. The hole is initially out of alignment with the reservoir port to close the reservoir port. A seal locking element may be retaining the sliding seal in position to close the reservoir port. The method further includes, extending a plunger of a transfer device through the hole in the sliding seal, for example, to release the seal locking element, sliding the sliding seal to align the hole and plunger with the reservoir port, and opening the reservoir port with the plunger to provide a fluid path from the reservoir port to a transfer port.

In an embodiment, the method further includes sealing the reservoir port with the plunger.

A system for transfer of fluid according to an example embodiment of the present invention includes an interface device including a mounting plate to mount the interface device to a reservoir, and a sealing element. The mounting plate includes a reservoir port. The sealing element is movable between an open position and a closed position. When the sealing element is in the closed position, the sealing element closes the reservoir port, thereby preventing the flow of fluid through the reservoir port. The system further includes a transfer device including a transfer body having a bore therethrough and a plunger assembly slidably disposed in the bore of the transfer body. The plunger assembly has a front plunger port and is operable to provide a fluid path between the front plunger port and a transfer port. The plunger assembly cooperates with the sealing element to allow transfer of fluid into or out of the reservoir through the fluid path when the sealing element is in the open position. The transfer device is configured to maintain a sterile environment or path for the fluid being transferred.

In an embodiment, the sealing element is a sliding valve. The sealing element and the mounting plate can define a steam cleanable surface exposed to an inside of the reservoir when the sealing element is in the closed position. Further, the sealing element can have a hole to receive the plunger assembly.

In an embodiment, the plunger assembly includes a valve movable between an open position and a closed position to control flow of the fluid through the front plunger port. The plunger assembly may include an inner plunger operable to move the valve between the open and closed positions. The valve may include a seal at the inner plunger, e.g., as a plug seal or a radial seal, configured to seal the front plunger port when the valve is in the closed position. Further, the plunger assembly may include an intermediate plunger having a bore therethrough, and the inner plunger may be slidably disposed in the bore of the intermediate plunger. In some embodiments, the intermediate plunger includes the front plunger port. The plunger assembly may further include an outer plunger slidably disposed in the bore of the transfer body, the outer plunger having a bore therethrough, and the intermediate plunger may be slidably disposed in the bore of the outer plunger. Each of the intermediate and outer plungers may include a fluid port. The plunger assembly may be operable to align the fluid ports with the transfer port to provide the fluid path between the front plunger port and the transfer port. In an embodiment, the transfer device includes one ore more guides, such as pins traveling in slots, to limit movement of the intermediate and outer plungers relative to each other and to the transfer port.

The transfer port may be coupled to a container to allow the transfer of fluid between the reservoir and the container. In an embodiment, the body of the transfer device includes the transfer port. Alternatively, the plunger assembly can include the transfer port.

In an embodiment, the interface device is operable to move the front plunger port with movement of the sealing element to align the front plunger port with the reservoir port. Alternatively, the interface device may be operable to move the sealing element with movement of the front plunger port to align the sealing element and the front plunger port with the reservoir port. The interface device can further include a seal locking element configured to retain the sealing element in the closed position. The sealing element can be configured to cooperate with the transfer device to release the seal locking element, the sealing element thereafter being movable to the open position. For example, the seal locking element can include a pin configured to engage the sealing element and prevent movement of the sealing element until the pin is displaced by the plunger assembly. The interface device can further include a plunger assembly locking element configured to prevent movement of the front plunger port away from the reservoir port when the sealing element is in the open position. The plunger assembly locking element may include a pin configured to engage a groove in the plunger assembly.

As described above, the transfer device can include a transfer coupling member or element to align the transfer device with the interface device. The coupling element can be configured to close the body and to couple to the interface device and open the body to the interface device. The interface device can include an interface coupling member or element configured to couple to the transfer coupling element and open the transfer device. The interface coupling element may be movable with the sealing element. The plunger assembly of the transfer device may be configured to extend through the coupling elements and cooperate with the interface device to allow transfer of fluid through the fluid path.

In an embodiment, the coupling elements cooperate to open or close a passage through the coupling elements, and the open passage is configured to receive the plunger assembly. Each of the coupling elements may include a disc having an opening therethrough. The coupling elements may be configured to open and close the passage with rotation of the discs. Also included may be a collar to cause the discs to rotate with rotation of the collar. For example, the collar can include a flange to engage one of the discs and rotationally couple the collar and the discs. Furthermore, the discs can include respective mating faces which are configured to rotationally couple the discs.

The interface device can include a seal plate coupled to the mounting plate, the seal plate configured to position the sealing element proximate the reservoir port. The interface device can further include an actuating mechanism to move the sealing element relative to the mounting plate, and may also include a seal, e.g., a wiper seal, between the seal plate and the mounting plate, the seal encircling the sealing element. In an embodiment, the seal plate is movably coupled to the mounting plate and the actuating mechanism may be configured to move the seal plate relative to the mounting plate, thereby moving the sealing element relative to the mounting plate.

A method for transfer of fluid according to an example embodiment of the present invention includes providing an interface device including a reservoir port in a mounting plate, and a sealing element movable between open and closed positions, and connecting the mounting plate to a reservoir. The method further includes coupling a transfer device that includes a plunger assembly to the interface device, moving the sealing element to the open position to open the reservoir port, operating the plunger assembly to provide a fluid path between a front plunger port and a transfer port, and allowing flow of fluid into or out of the reservoir through the fluid path.

In an embodiment, the sealing element and the mounting plate define a steam cleanable surface exposed to an inside of the reservoir when the sealing element is in the closed position, and the method can include sterilizing the inside of the reservoir and the surface.

In an embodiment, the plunger assembly includes a valve to open or close the front plunger port. Allowing flow of the fluid through the fluid path includes opening the front plunger port with the valve. The interface device and the transfer device may further include respective coupling elements, and coupling the transfer device to the interface device can include aligning the coupling elements. For example, coupling the transfer device to the interface device can include rotating a collar to engage the coupling elements and lock the coupling elements together. Coupling the transfer device to the interface device may further include opening a passage through the coupling elements with rotation of the collar.

The plunger assembly can include an outer plunger. Operating the plunger assembly can include pushing the plunger assembly, or a part thereof, e.g., the outer plunger, toward the interface device through the open passage. Further, pushing the outer plunger toward the interface device can include twisting the outer plunger to unlock or lock the outer plunger. The plunger assembly may further include an intermediate plunger slidably disposed in the outer plunger, and operating the plunger assembly can include pushing the intermediate plunger toward the interface device to unlock the sealing element. Further, moving the sealing element to the open position can include moving the sealing element after being unlocked by the intermediate plunger. The plunger assembly may further include an inner plunger slidably disposed in the intermediate plunger, and opening the front plunger port with the valve includes moving the inner plunger relative to the intermediate plunger, for example, by pulling the inner plunger away from the reservoir port. The front plunger port may be closed with the valve to disallow transfer of fluid into or out of the reservoir through the fluid path.

The method can include connecting a container to the transfer port to allow the transfer of fluid between the reservoir and the container. Further, the method can include moving the sealing element to the closed position and decoupling the transfer device from the interface device.

Systems, methods, and devices for transfer of fluid described herein can include one or more seals configured to provide a sterile barrier between the fluid path and the environment. The systems, methods, and devices can maintain a sterile path or environment for the fluid being transferred.

Embodiments of the present invention have many advantages. Using a fluid transfer system including the interface device and transfer device(s) as described herein for sterile sampling of fluid from a reservoir can eliminate many steps in traditional sampling and post-sample handling processes. Sampling container types and sizes can be determined after the start of the process from which the samples are to be taken, allowing for increased flexibility. The system does not require tubes or manifolds, which can provide a more organized and efficient workspace. The sliding valve of the interface device does not contain any hold-up volume, which can reduce or eliminate product waste during the sampling process, thereby making embodiments of the present invention suitable for high value sampling applications. In addition, the sliding valve can be opened and closed repeatedly without trapping fluid in the valve. Advantageously, a large number of samples (e.g., 50 samples) can be taken from the process without the need to have the sample containers pre-attached to the interface device. The interface device provides an enclosed chamber, which is a previously sterilized, clean environment. The interface device enables the 'clean' environment to be isolated from a 'dirty,' external environment. The mating, rotating coupling elements help preserve sterility and process integrity as does the outer plunger. The plunger assembly allows for easy actuation of the sample with controlled volume measurements, which is another benefit for high value sampling applications. Another advantage of a fluid transfer system according the present invention is the absence of piercing needles, which increases process and operator safety.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2A-E are top views of the system of FIG. 1D illustrating the process of operating the system;

FIGS. 3A-E are cross-sectional views of the system of FIG. 1D corresponding to the top views of FIGS. 2A-E;

FIG. 14 shows the present invention in another contemplated use;

FIGS. 15B-15H are respective top perspective, bottom perspective, left side, right side, front, top, and bottom views of the embodiment of FIG. 15A;

FIGS. 16B-16H are respective top perspective, bottom perspective, left side, right side, front, top, and bottom views of the embodiment of FIG. 16A;

FIGS. 17A-G are top views of a system including the interface device of FIG. 15A and the transfer device of FIG. 16A illustrating the process of operating the system;

FIGS. 18A-G are sectional views of the devices of FIG. 15A and FIG. 16A corresponding to the top views of FIGS. 17A-17G;

FIG. 18H is a sectional view of the transfer device of the system of FIG. 17A;

FIG. 18J is a sectional view of the transfer device of the system of FIG. 17C;

FIG. 18K is an expanded view of the reservoir port and front plunger port of the system of FIG. 18F;

FIG. 18L is an expanded view of the reservoir port and front plunger port of the system of FIG. 18G;

FIG. 18M is a sectional view of the system of FIG. 17D;

FIG. 18N an expanded view of the front plunger port of the system of FIG. 18M;

FIG. 18P is a sectional view of the system of FIG. 17E;

FIG. 18R is an expanded view of the front plunger port of the system of FIG. 18P;

FIGS. 19B-19H are respective top perspective, bottom perspective, left side, right side, front, top, and bottom views of the embodiment of FIG. 19A.

FIGS. 20B-20H are respective top perspective, bottom perspective, left side, right side, front, top, and bottom views of the embodiment of FIG. 20A.

FIGS. 21A-21F are top views of a system including the interface device of FIG. 19A and the transfer device of FIG. 20A illustrating the process of operating the system;

FIG. 22A is sectional view of the system of FIG. 21A;

FIG. 22B is a sectional view of the transfer device of the system of FIG. 21A;

FIGS. 22G and 22S are sectional views of the system of FIG. 21D;

FIG. 22H is a sectional view of the transfer device of the system of FIG. 21D;

FIG. 22T is an expanded view of the of the system of FIG. 22S;

FIGS. 22I, 22J and 22K are sectional views of the system of FIG. 21E;

FIG. 22L is an expanded view of the of the system of FIG. 22K;

FIG. 22Q is an expanded view of the reservoir port and front plunger port of the system of FIG. 22I;

FIGS. 22M, 22N and 22O are sectional views of the system of FIG. 21F;

FIG. 22P is an expanded view of the of the system of FIG. 22O;

FIG. 22R is an expanded view of the reservoir port and front plunger port of the system of FIG. 22M.

DETAILED DESCRIPTION OF THE INVENTION

A description of example embodiments of the invention follows.

Figure 1A:
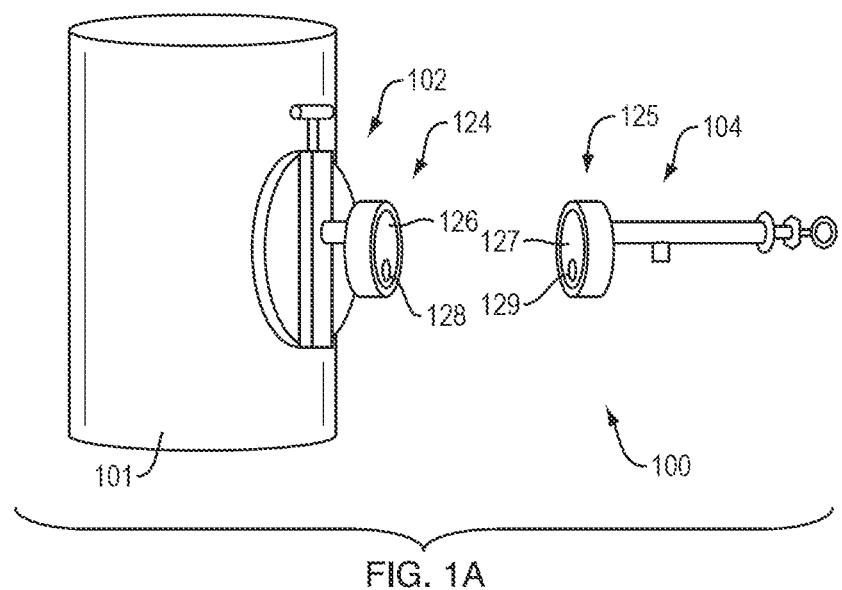
FIG. 1A is a schematic illustration of an example fluid transfer system according to an embodiment of the present invention.

FIG. 1A is a schematic illustration of an example fluid transfer system 100 according to an embodiment of the present invention. The fluid transfer system 100 includes an interface device 102 to be mounted to a reservoir 101 and a transfer device 104 to be selectively coupled to the interface device 102. The interface device 102 includes a coupling member 124 that includes a sliding element 126 having an opening 128. The transfer device 104 includes a coupling element or member 125 that includes a sliding element 127 having an opening 129. In FIG. 1A, the interface and transfer devices 102 and 104 are shown uncoupled. The coupling members 124 and 125 are in respective closed positions, the opening 128 being out of alignment with the interface device 102 and the opening 129 being out of alignment with the transfer device 104. The transfer coupling member 125 is configured to couple to the interface coupling member 124. The interface coupling member 124 and transfer coupling member 125 cooperate to open or close a passage through the coupling members. In the example shown, the coupling members are configured to open and close the passage with rotation of the sliding elements 125 and 127.

Figure 1B:
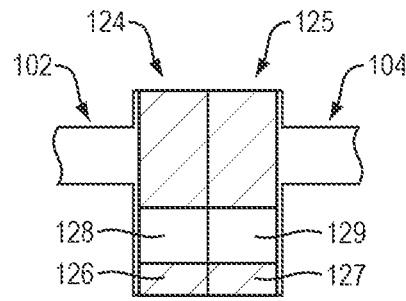
FIG. 1B is a cross-sectional view illustrating the coupling members of the system of FIG. 1A coupled and in closed positions.

FIG. 1B illustrates the coupling members 124 and 125 of the system 100 of FIG. 1A coupled and in closed positions. As shown, the openings 128 and 129 are not aligned with the interface and transfer devices 102 and 104. FIG. 1B corresponds to FIGS. 3A and 5B, which illustrate additional details of the coupling members that are described below in reference to FIGS. 3A and 5B.

Figure 1C:
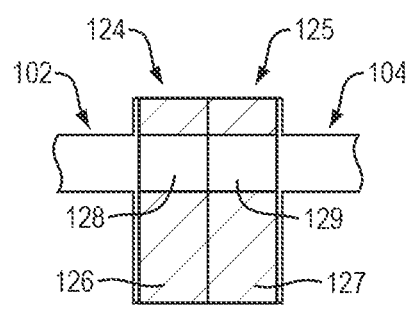
FIG. 1C is a cross-sectional view illustrating the coupling members of the system of FIG. 1A coupled and in open positions.

FIG. 1C illustrates the coupling members of the system of FIG. 1A coupled and in open positions. The sliding elements 126 and 127 have been rotated such that the openings 128 and 129 are aligned with the interface and transfer devices 102 and 104. When the openings are aligned, the coupling members 124 and 125 are locked together and cannot be de-coupled until unlocked. As described in more detail below, the open passage through the coupling members 124 and 125 can, for example, receive a transfer member of the transfer device 104. The transfer member can extend through the passage and cooperate with the interface device 102 to allow transfer of fluid into or out of the reservoir 101. As will be described below, the interface device may include a sliding seal 110 (FIG. 1D) which cooperates with the transfer member to open and close a reservoir port 108 (FIG. 1D) of the interface device 102. The fluid transfer system 100 can be used, for example, to sample fluid from the reservoir 101 into a sampling container connected to the transfer device 104. This and other contemplated uses for a fluid transfer system such as system 100 are described in reference to FIGS. 12-14.

The coupling members and the transfer member of the fluid transfer system described are configured to allow a user to successively connect sterile transfer or sample devices to the interface device while keeping the interface device 'clean' or uncontaminated. A cover (not shown) may be placed over the interface device when not in use to keep the interface device clean, e.g., to shield the interface device from dust and dirt that may be present in the external environment of the interface device.

The coupling members of the interface and transfer devices 102 and 104 could also include linear sliding coupling elements, for example. Preferably, fluid transfer system is configured such that the coupling members slide along one axis and other elements of the system, such as the sliding seal of the interface device, slide along different, e.g., orthogonal, axes. Alternatively, one sliding motion may be linear and the other sliding motion may be rotary. In the example described below in reference to FIG. 1D, the interface device includes a linear sliding valve and the coupling members include rotary sliding elements, e.g., discs.

Figure 1D:
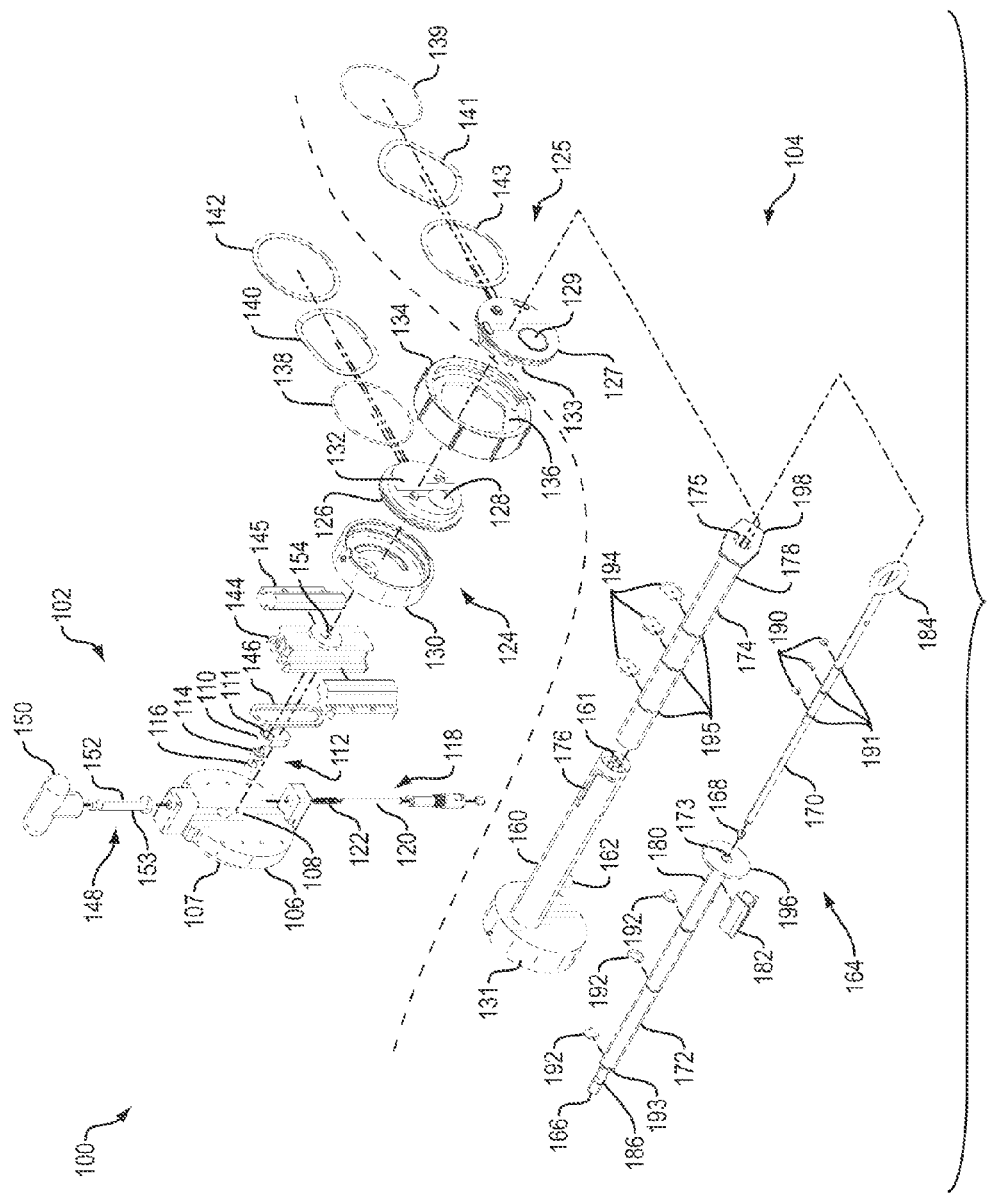
FIG. 1D shows an embodiment of the present invention in exploded view.

FIG. 1D shows an example system 100 for transfer of fluid including an interface device 102 and a transfer device 104. The figure shows the elements of the interface device 102 and the transfer device 104 in exploded view. A dashed line indicates the separation between the elements of the interface device 102 and those of the transfer device 104.

As shown in FIG. 1D, the interface device 102 includes a mounting plate 106 to mount the interface device 102 to a reservoir, e.g., a bioreactor or stainless steel tank (not shown). The mounting plate 106 includes the reservoir port 108. As shown, the reservoir port 108 is a circular opening that extends through the mounting plate 106. The mounting plate 106 includes a flange 107 for mounting to an existing port of the reservoir. The flange 107 can have standard dimensions to fit a standard port, such as a TC port or an INGOLD® port.

The interface device 102 includes a sealing element 110 that is movable between an open position and a closed position. The sealing element 110 closes the reservoir port 108 when the sealing element is in the closed position. As shown, the sealing element is a linearly sliding valve that includes a hole 111. Sliding the sealing element 110 to bring the hole 111 into alignment with the reservoir port 108 opens the reservoir port (see also FIGS. 3A-D). Conversely, sliding the sealing element 110 to bring the hole 111 out of alignment with the reservoir port 108 closes the reservoir port. The sealing element could also be a rotary sliding valve, for example.

As shown in FIG. 1D, the interface device 102 includes a seal locking element 112 to retain the sealing element 110 in the closed position. As shown, the seal locking element 112 includes a pin 114 and a resilient member, e.g., a spring, 116. The pin 114 is configured to extend into the hole 111 of the sealing element 110 and prevent movement of the sealing element until the pin 114 is displaced by a transfer member of the transfer device 104, e.g., plunger assembly 164 (see FIGS. 3A-3C). The spring element 116 biases the pin 114 into engagement with the sealing element 110. When the plunger assembly 164 of the transfer device 104 extends through hole 111 of the sealing element 110 it displaces the pin 114, thereby releasing the seal locking element 112. Once the seal looking element 112 is released, the sealing element 110 can be moved to the open position as described in reference to FIGS. 3C-3E.

The interface device 102 includes a transfer member locking element, e.g., plunger assembly locking element 118 mounted to the bottom of the plate 106, to prevent movement of a front plunger port 166 of the transfer device away from the reservoir port 108 when the sealing element is in the open position. The plunger assembly locking element 118 includes a pin 120 to engage groove 186 of the plunger assembly 164. A spring 122 forces the pin 120 into the groove 186 when the front plunger port 166 is aligned with the reservoir port 108.

The interface device 102 also includes a seal plate 144 that is movably coupled to the mounting plate 106 through use of brackets 145. As shown, each bracket 145 includes a side rail that engages the seal plate 144. The seal plate is configured to position the sealing element 110 proximate the reservoir port 108. A wiper seal 146 is positioned between the seal plate 144 and the mounting plate 106 and is set in and carried by the seal plate 144 (see FIG. 3A). The wiper seal 146 encircles the sealing element 110.

The interface device 102 further includes an actuating mechanism 148 mounted to the top of the plate 106 to move the seal plate 144 relative to the mounting plate 106. As shown, the actuating mechanism 148 includes a handle 150 coupled to a screw 152 that is coupled to the seal plate 144. The screw 152 includes a thread 153 to engage a corresponding thread in mounting plate 106. Preferably, the thread 153 is a half-turn thread. An operator can use the handle 150 to slide the seal plate 144 up or down relative to the mounting plate 106, thereby moving the sealing element 110 between the open and closed positions. While a manual actuating mechanism 148 is illustrated in FIG. 1D, it should be understood that automatic actuation is within the scope of the present invention. Furthermore, any mechanical, pneumatic, hydraulic, magnetic, electromagnetic or other suitable mechanism may be used to move the seal plate 144 relative to the mounting plate 106.

As shown in FIG. 1D, the interface device 102 includes an interface coupling element or member 124 to couple to a transfer coupling element or member 125 of the transfer device 104. The interface coupling element is movable with the sealing element 110. As shown, the interface coupling element 128 is coupled to the seal plate 144 via a housing 130. The housing 130 and the seal plate 144 may be formed as a unitary piece. Alternatively, the housing 130 may be joined, attached or fastened to the seal plate 144 by suitable means. The housing 130 and the seal plate 144 cooperate to form a transfer member receptacle configured to receive a transfer member of a transfer device, e.g., the plunger assembly 164 of the transfer device 104. As shown, seal plate 144 includes a channel 154 that is configured to receive the plunger assembly 164.

The interface coupling element 124 and transfer coupling element 125 cooperate to open or close a passage through the coupling elements. The open passage is configured to receive the plunger assembly 164. As shown, the coupling elements 124 and 125 include respective discs 126 and 127. As will be described in more detail below, discs 126 and 127 include respective openings 128 and 129, and the coupling elements are configured to open and close the passage with rotation of the discs. The discs 126 and 127 include respective mating faces 132 and 133 to rotationally couple the discs. A collar 134 includes a flange 136 to engage one of the discs 126, 127 and to rotationally couple the collar 134 to the discs, such that rotation of the collar 134 causes rotation of the discs. As shown, the flange 136 includes a hexagonal opening that is configured to engage a corresponding hexagonal portion of the disc 127.

As shown in FIG. 1D, the transfer device 104 includes a body 160 having a bore 161 which extends through the length of the body 160. The body 160 is connected to housing 131 that is configured to receive the disc 127. Alternatively, the body 160 and the housing 131 may be formed in one piece. A transfer port 162 is provided on the body 160. Slidably disposed in the bore 161 is the transfer member or plunger assembly 164. As shown, the plunger assembly 164 includes an inner plunger 170, an intermediate plunger 172, and an outer plunger 174. The plunger assembly 164 is operable to provide a fluid path between the front plunger port 166 and the transfer port 162. The plunger assembly 164 cooperates with the sealing element 110 of the interface device 102 to allow transfer of fluid into or out of a reservoir through the fluid path when the sealing element 110 is in the open position. The interface device 102 is operable to move the front plunger port 166 of the plunger assembly 164 with movement of the sealing element 110 to align the front plunger port 166 with the reservoir port 108.

The plunger assembly 164 includes a valve member 168 that is movable between an open position and a closed position to control flow of fluid through the front plunger port 166. The inner plunger 170 is slidably disposed in bore 173 of the intermediate plunger 172. The inner plunger includes a handle 184 and is operable to move the valve member 168 between the open and closed positions. As shown, the front plunger port 166 is provided at the front of the intermediate plunger 172. The intermediate plunger 172 is slidably disposed in bore 175 of the outer plunger 174. The outer plunger 174, in turn, is slidably disposed in the bore 161 of the body 160 of the transfer device 104. The outer plunger 174 is configured to extend through the coupling members 124 and 125 and into the interface device 102 to minimize exposure of the intermediate and inner plungers to non-sterile or 'dirty' surfaces, e.g., the mating faces 132 and 133 of the coupling elements 124 and 125. The intermediate plunger 172 is configured to provide a fluid path for the transfer of fluid. The inner plunger is configured to provide valving.

The transfer device 104 can maintain a sterile path for the fluid being transferred. To that end, the transfer device 104 includes one or more seals configured to provide a sterile barrier between the fluid path and the environment. As shown in FIG. 1D, the transfer device 104 includes seals 190, 192 and 194, which, in this embodiment, are O-rings. The inner plunger 170, intermediate plunger 172, and outer plunger 174 each include respective grooves or channels 191, 193, and 195 to seat the respective seals 190, 192, and 194. Additional seals may be provided as described herein.

Figure 2C:
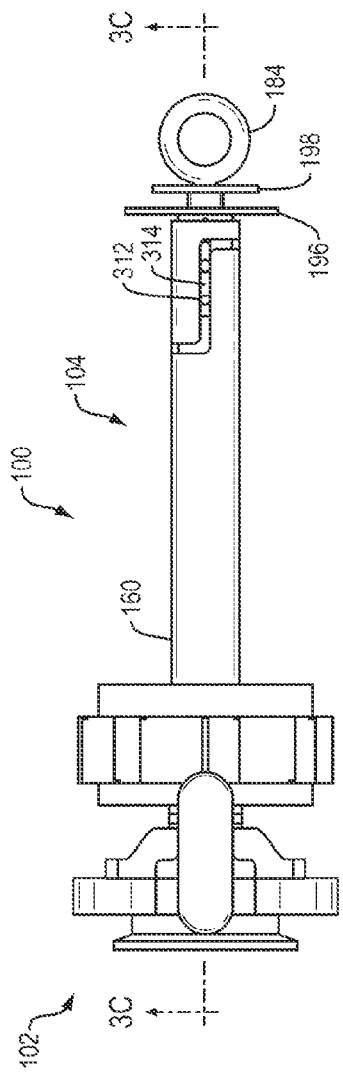
Figure 3C:
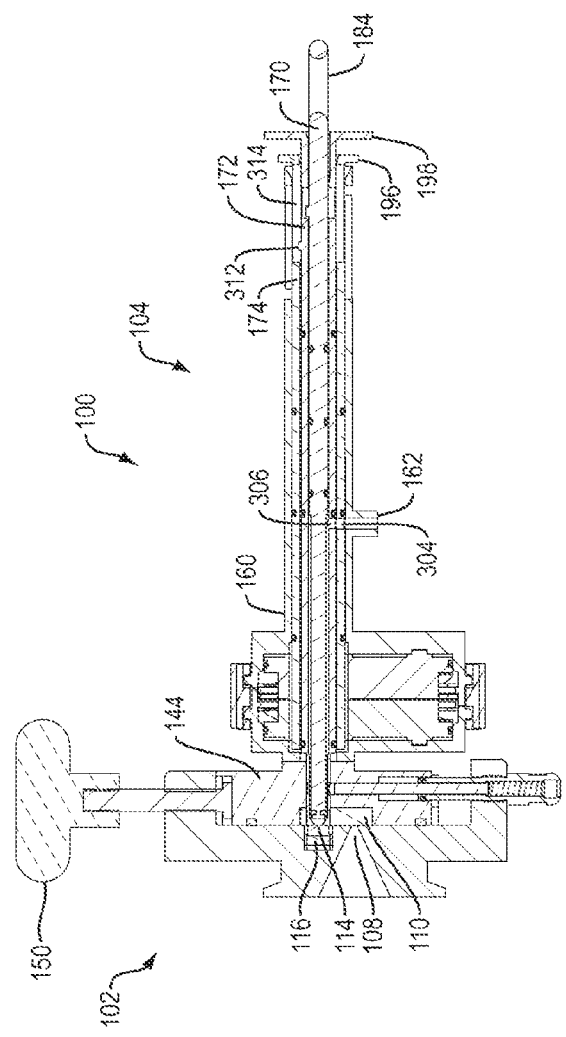

FIGS. 2A-2E and 3A-3E are respective top and cross-sectional views of the system 100 of FIG. 1D illustrating the process of operating the system 100 for transferring fluid. In FIGS. 2A and 3A, the system 100 is shown in a closed position. The reservoir valve or sliding seal 110 is in the closed position sealing the reservoir port 108. As shown, the hole 111 of the sliding seal 110 is out of alignment with the reservoir port 108 to close the reservoir port. Pin 114 of the seal locking element 112 retains the sliding seal 110 in position to close the reservoir port 108 until the seal locking element is released. The sealing element 110 and the mounting plate 106 can define a steam cleanable surface 302 that is exposed to the inside of the reservoir when the sealing element is in the closed position.

As shown in FIGS. 2A and 3A, the fluid transfer member of the transfer device 104, i.e. the plunger assembly 164, has been aligned with the interface device 102. The transfer coupling member 125 of the transfer device 104 is coupled to the interface coupling member 124 of the interface device 102. The mating faces 132 and 133 of the discs 126 and 127 butt against each other and the discs are rotationally coupled. The discs, however, have not been rotated and their openings 128, 129 (FIG. 1D) are not aligned with the transfer device 104 or the interface device 102. Thus, there is no passage through the coupling members 124 and 125 to receive the transfer member, i.e., the plunger assembly 164. The fluid transfer member receptacle of the interface device 102, i.e. the seal plate 144, is closed, as is the body 160 of the transfer device 104.

In FIGS. 2B and 3B, the openings in the discs 126 and 127 are aligned with the transfer member, i.e., plunger assembly 164, and the transfer member is extended through the openings. The discs 126 and 127, which are rotationally coupled, are rotated using collar 134 to bring the respective openings 128 and 129 into alignment with the fluid transfer member receptacle and the fluid transfer member, thereby creating a passage through which the fluid transfer member can be extended. Further details regarding the discs of the coupling members are provided below in reference to FIGS. 4A-C and 5A-C. The outer plunger 174 is configured to extend through the openings 128 and 129 to prevent contact of the intermediate plunger 172 with the coupling members 124 and 125, whose mating surfaces 132 and 133 were exposed to the environment prior to coupling the devices. The outer plunger 174 acts as sleeve to shield the intermediate plunger 172, including the front plunger port 166. Preferably, the system 100 is configured to provide an air gap 308 when the outer plunger 174 is extended through the opening 126 and 127, the air gap separating the front of the outer plunger 174 from coupling members 124 and 125 and the interface device 102. The purpose of the air gap is to avoid contact with potentially contaminated surfaces.

As show in FIG. 3B, the intermediate plunger 172 includes a fluid port 306 and outer plunger 174 includes a fluid port 304. The plunger assembly 164 may be operable to align the fluid ports 304 and 306 with the transfer port 162 to provide the fluid path between the front plunger port 166 (FIG. 1D) and the transfer port 162. As shown, the combination of extending the outer plunger 174 through the openings 128 and 129 and rotating or twisting the outer plunger within the transfer body 160 has resulted in the fluid port 304 being aligned with the transfer port 162. The fluid port 306, however, is not yet aligned. The transfer device includes guides 176 and 178 to limit movement of the intermediate and outer plungers 172 and 174 relative to each other and to the transfer port 162. A guide 180 limits movement of the inner plunger relative to the intermediate plunger. In the embodiment shown, the guides comprise pins and slots that cooperate to limit length of travel and to limit or prevent rotation, e.g., to align the ports 304, 306, and 162. For example, guide 178 comprises a pin 312 on intermediate plunger 172 and as slot 314 on outer plunger 174. The slot 314 of the plunger 174 limits travel and prevents rotation of the pin 312 in the slot, thereby limiting travel and preventing rotation of the intermediate plunger 172 relative to the outer plunger 174. As shown, the guide 176 includes a slot 316 in the transfer body 160 that cooperates with a pin (not shown) on the outer plunger 174. The slot 316 includes two turns (see FIG. 2B), which can be used to lock the outer plunger 174 in two positions. To extend the outer plunger 174 through the coupling members 124 and 125, an operator must first twist the outer plunger 174 relative to the transfer body 160 to unlock the plunger. The operator can then push the outer plunger 174 toward the interface device with the pin traveling through the axial slot 316 to extend the outer plunger through the coupling members. The operator can then lock the outer plunger in the extended position with another twisting motion.

A plunger lock 182 prevents the operator from advancing the intermediate plunger 172 relative to the outer plunger 174 while pushing the outer plunger 174 toward the interface device. As shown in FIGS. 2B and 3B, the plunger lock 182 can be a removable clip that extends between a handle 318 of the outer plunger 174 and a handle 320 of the intermediate plunger 172 (see also FIG. 1D).

In FIGS. 2C and 3C, the inner and intermediate plungers 170 and 172 have been advanced into the interface device 102. In order to advance the plungers, the plunger lock 182 (FIGS. 2B and 3B) was removed. As shown, the inner and intermediate plungers 170 and 172 extend through the hole 111 of the sliding seal 110. The pin 114 has been pushed from the hole 111, thereby compressing spring 116 and releasing the seal locking element 112. The fluid port 306 of the intermediate plunger 172 is now aligned with the fluid port 304 of the outer plunger 174 and transfer port 162.

In FIGS. 2D and 3D, the reservoir valve, i.e. sliding seal, 110 is actuated. With the inner and intermediate plungers 170 and 172 positioned in the fluid transfer member receptacle 144, the reservoir valve 110 is actuated to open the reservoir port 108 to the fluid transfer member receptacle 144. In this embodiment, the valve is actuated by sliding the sliding seal 110 linearly using actuating mechanism 148. An operator can turn the handle 150 to slide the seal plate 144 down. This moves the sliding seal 110 down to align the hole 111 and the inner and intermediate plungers 170, 172 with the reservoir port 108. Although the hole 111 is now aligned with the reservoir port 108, the plug seal 168 of the plunger assembly 164 seals the reservoir port 108. As shown, the plug seal 168 is positioned at the front end of inner plunger 170 and within the intermediate plunger 172. A transfer member locking element 118 retains the intermediate plunger 172 in position.

In FIGS. 2E and 3E, the inner plunger 170 is moved away from the reservoir port 108 and the reservoir port is opened. For example, an operator can pull on handle 184 to move the inner plunger 170 away from the reservoir port 108, thereby moving the seal plug 168 away from the reservoir port, which opens the reservoir port. Guide 180 limits movement of the inner plunger 170. As shown, the guide 180 comprises a slot 318 in the intermediate plunger 172 that cooperates with a pin 320 on the inner plunger 170. Opening the reservoir port 108 with the inner plunger 170 provides a fluid path from the reservoir port 108 to the transfer port 162 as described below in reference to FIG. 3F.

Figure 3F:
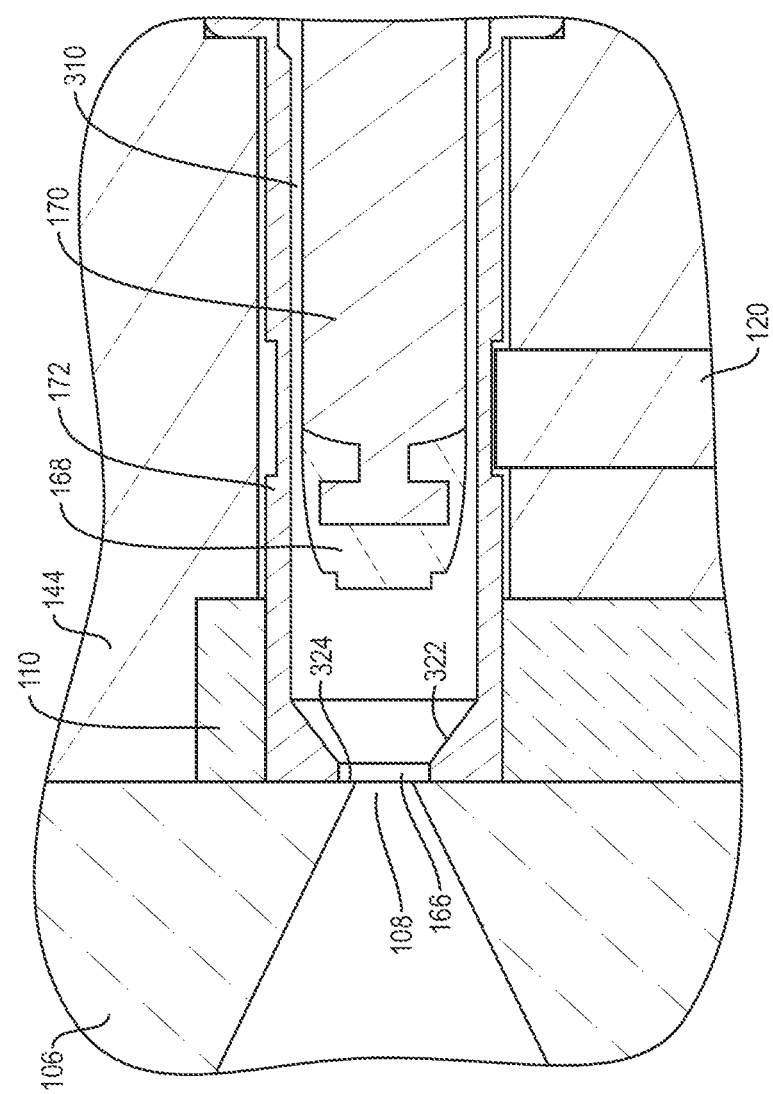
FIG. 3F is an expanded view of the reservoir port and front plunger port of FIG. 3E.

FIG. 3F is an expanded view of the reservoir port and front plunger port of FIG. 3E. The plug seal 168 is a valve member that cooperates with valve seat 324 of the mounting plate 106 of the interface device to open and close the reservoir port 108. In addition, the seal 168 and the intermediate plunger 172 also form a valve to open and close the front plunger port 166 of the plunger assembly 164. As shown, the plug seal 168 is also a valve member that cooperates with valve seat 322 of the intermediate plunger 172. Moving the seal plug 168 away from the reservoir port 108 (and the valve seat 322) opens the front plunger port 166, thereby allowing flow of fluid through the fluid path. Fluid can now flow from the reservoir port 108 to the transfer port 162 (FIG. 3E), or vice versa, through a channel 310, defined by the inner and intermediate plungers 170 and 172, and through the aligned fluid ports 304 and 306. As shown, the channel 310 comprises a space between the inner plunger 170 and an inside of the intermediate plunger 172.

When the reservoir port 108 is open, the pin 120 of the transfer member locking element 118 retains the intermediate plunger 172 in position in the fluid transfer member receptacle, i.e., seal plate 144, of the interface device. This feature prevents accidental withdrawal of the intermediate plunger 172, e.g., through operator error, and contributes to maintaining integrity of the fluid path during the transfer of fluid.

Returning to FIG. 3E, the seals or O-rings 190 of the inner plunger 170 are spaced apart far enough to prevent over-wipe when the inner plunger moves within the intermediate plunger 172. The same applies to the seals or O-rings 192 and 194 of the intermediate and outer plungers 172 and 174, respectively. Preventing over-wipe contributes to the maintenance of a sterile fluid path.

Once the transfer of fluid is complete, the inner plunger 170 can be pushed back towards the reservoir port 108 to seal the reservoir port with seal plug 168. The reservoir valve 110 can then be actuated to close the reservoir port from the fluid transfer receptacle 144 by moving the sliding seal 110 up using actuating mechanism 148. The plunger assembly 164 can be withdrawn from the fluid transfer member receptacle and the interface device 102. Once the plunger assembly 164 is withdrawn, the discs 126 and 127 can be rotated back to close the fluid transfer member receptacle and the body 160.

FIGS. 4A-4C and 5A-5C are respective top and cross-sectional views of the coupling members or elements of the system 100 illustrating the process of coupling the transfer device 104 to the interface device 102. The figures show the coupling member 124 positioned in the housing 130 of the interface device 102 and the coupling member 125 positioned in housing 131 of the transfer device.

Figure 4A:
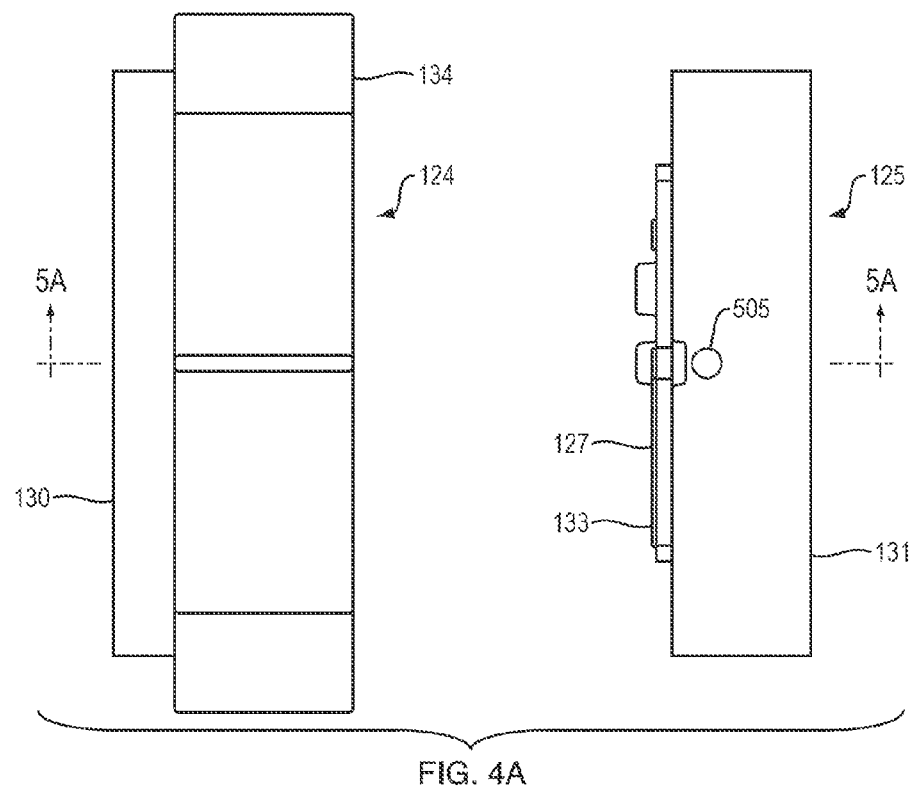
FIGS. 4A-4C are top views of the coupling members of the system of FIG. 1D illustrating the process of coupling two devices.
Figure 5A:
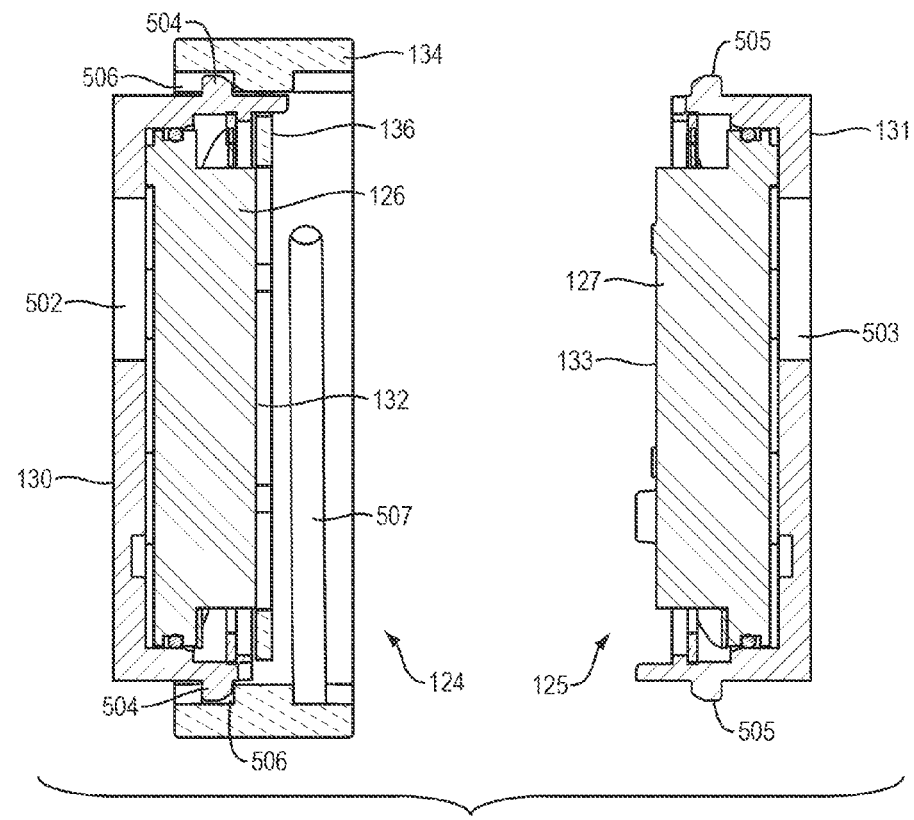
FIGS. 5A-5C are cross-sectional views of the coupling members of FIG. 1D corresponding to the top views of FIGS. 4A-4C.

In FIGS. 4A and 5A, the coupling members 124 and 125 are shown in the closed position. The opening 502 in the housing 130 of the interface device 102 is closed by disc 126, which is positioned in the housing 130 such that the opening 128 is out of alignment with the opening 502. The opening 503 in the housing 131 of the transfer device 104 is closed by the disc 127, which is positioned in the housing 131 such that the opening 129 of disc 127 is out of alignment with the opening 503. The collar 134 is shown coupled to the housing 130. The collar includes channels 506 for receiving nubs 504 of the housing 130 and channels 507 (see also FIGS. 8B-C) for receiving nubs 505 of the housing 131. Also shown are the flange 136 of the collar 134 and the mating faces 132 and 133 of the disc 126 and 127.

Figure 4B:
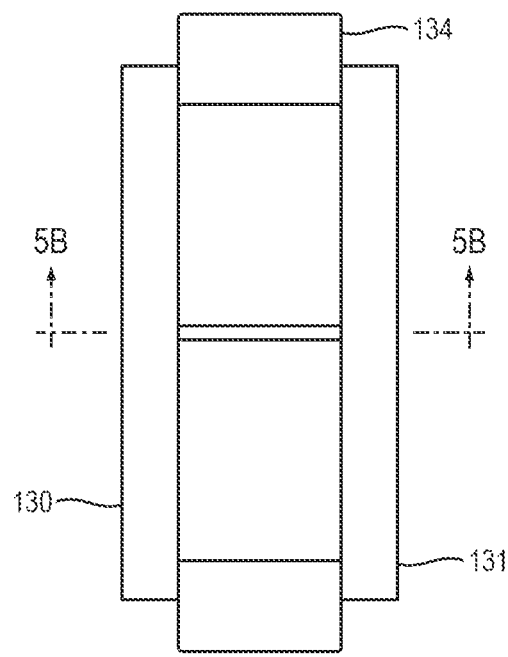
Figure 5B:
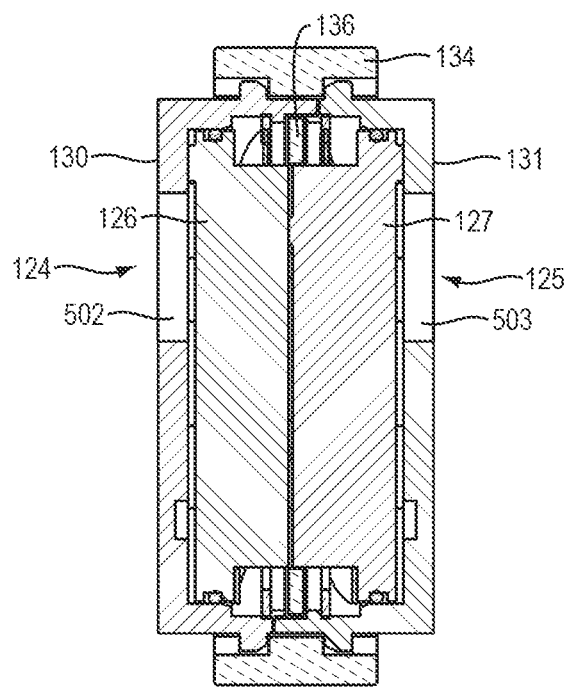

In FIGS. 4B and 5B, the transfer coupling member 125 of the transfer device 104 is coupled to the interface coupling member 124 of the interface device 102. The coupling members are not yet locked, as the collar 134 has not been rotated to engage the nobs 505 of the interface device. The openings 502 and 503 are still closed. The mating faces 132 and 133 of discs 126 and 127, respectively, butt against each other and the discs are rotationally coupled. The discs 126 and 127 are rotationally coupled via mating features of the mating faces 132 and 133, as is described below in reference to FIGS. 6 and 9.

Figure 4C:
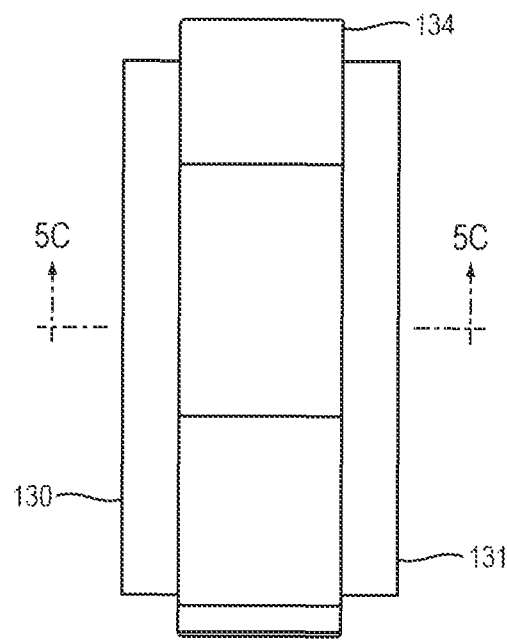
Figure 5C:
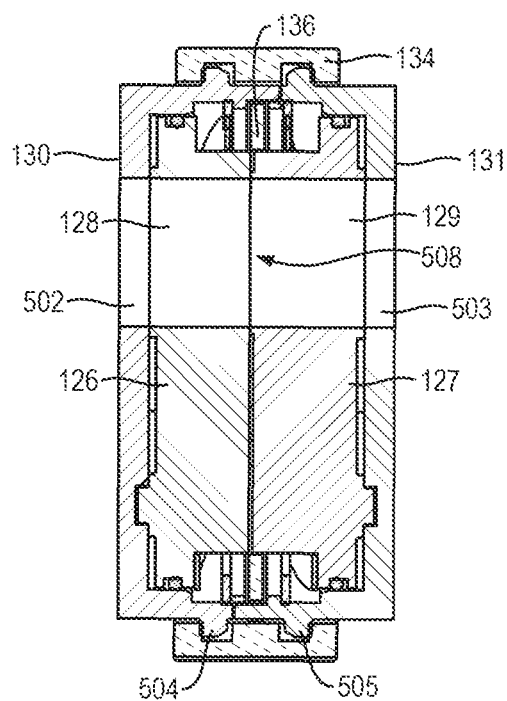

In FIG. 5C, the discs 126 and 127 are moved, i.e., rotated, relative to the housings 130 and 131, such that the openings 128 and 129 of discs 126 and 127 are aligned with the opening 502 of the interface device and the opening 503 of the transfer device. The aligned holes form a passage 508 through the coupling members 124 and 125 to receive the transfer member (not shown), e.g., the plunger assembly 164 (FIG. 1D). As shown in FIGS. 4C and 5C, the collar 134 is rotated relative to the housings 130 and 132. With rotation of the collar 134, the channels 506 and 507 of the collar 134 engage the nubs 504 and 505 and lock the housings 130 and 131 together, thereby locking the discs 126 and 127 together. In addition, the flange 136 of the collar 134 engages the disc 127, such that disc 127 is rotated with rotation of the collar 134. Because the disc 127 is rotationally coupled to disc 126, the disc 126 is rotated at the same time the disc 127 is rotated. Thus, rotation of collar 134 causes coupling and locking of the transfer device 104 to the interface device 102, and opening of the passage 508 through the coupling elements. Therefore, when the passage 508 is open, the transfer device 104 and interface device 102 are locked together through housings 130 and 131 and cannot be de-coupled until unlocked.

Figure 6:
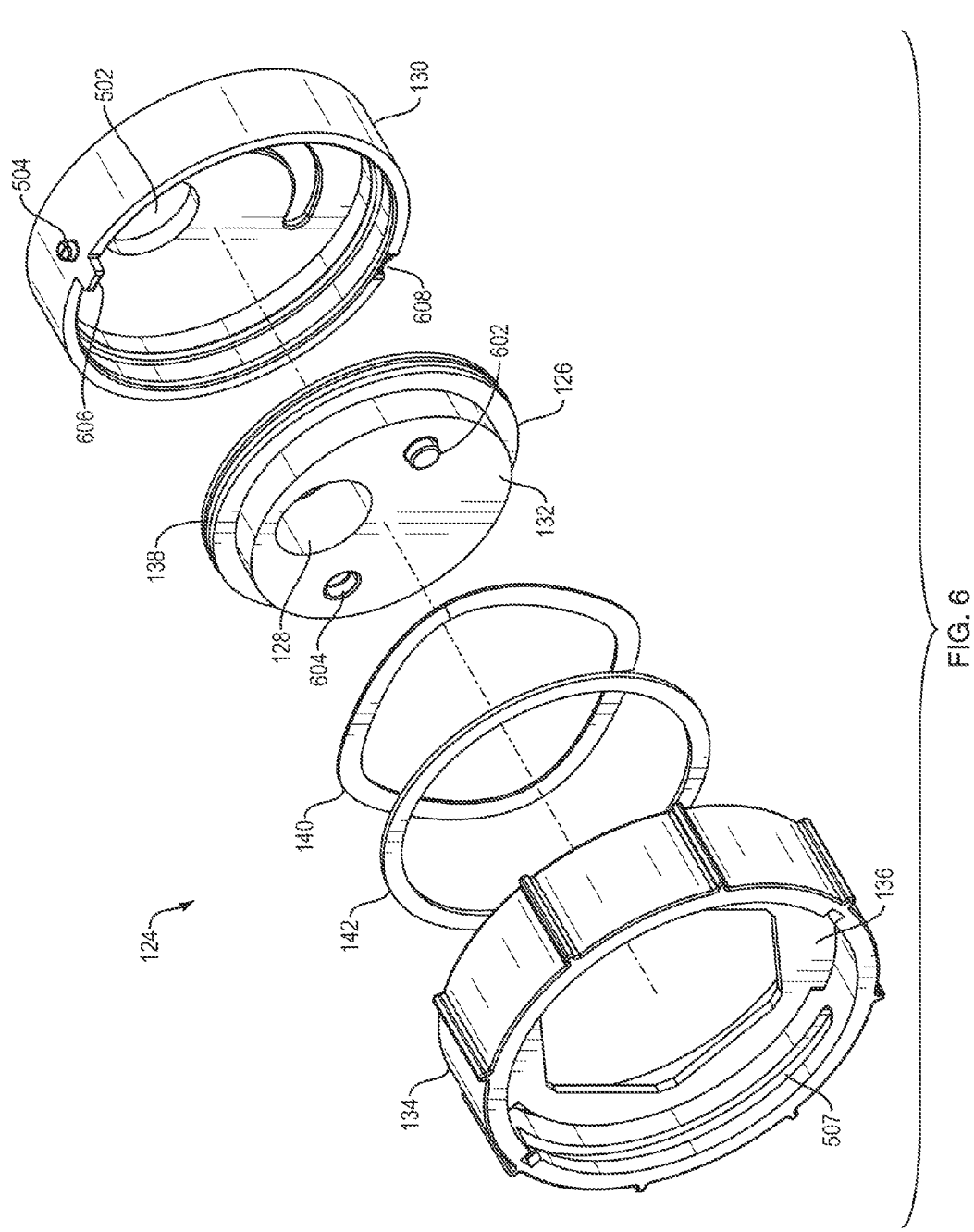
FIG. 6 shows the interface coupling member including the collar and the housing of the interface device of FIG. 1D in exploded perspective view.

FIG. 6 shows the coupling member 124 and the housing 130 of the interface device 102 of FIG. 1D. The coupling member 124 includes the disc 126, the seal 138, the spring 140, and the snap ring 142. In this embodiment, the housing 130 is a cylinder having a front and a back, the front being open to receive the disc 126 and the back being closed, except for the opening 502. As shown, the seal 138 is an O-ring that is seated in a groove in the perimeter of the disc 126. When the disc 126 is positioned in the housing 130, the seal 138 provides a perimeter seal between the disc 126 and the housing 130 (see FIGS. 8A-C).

Figure 9:
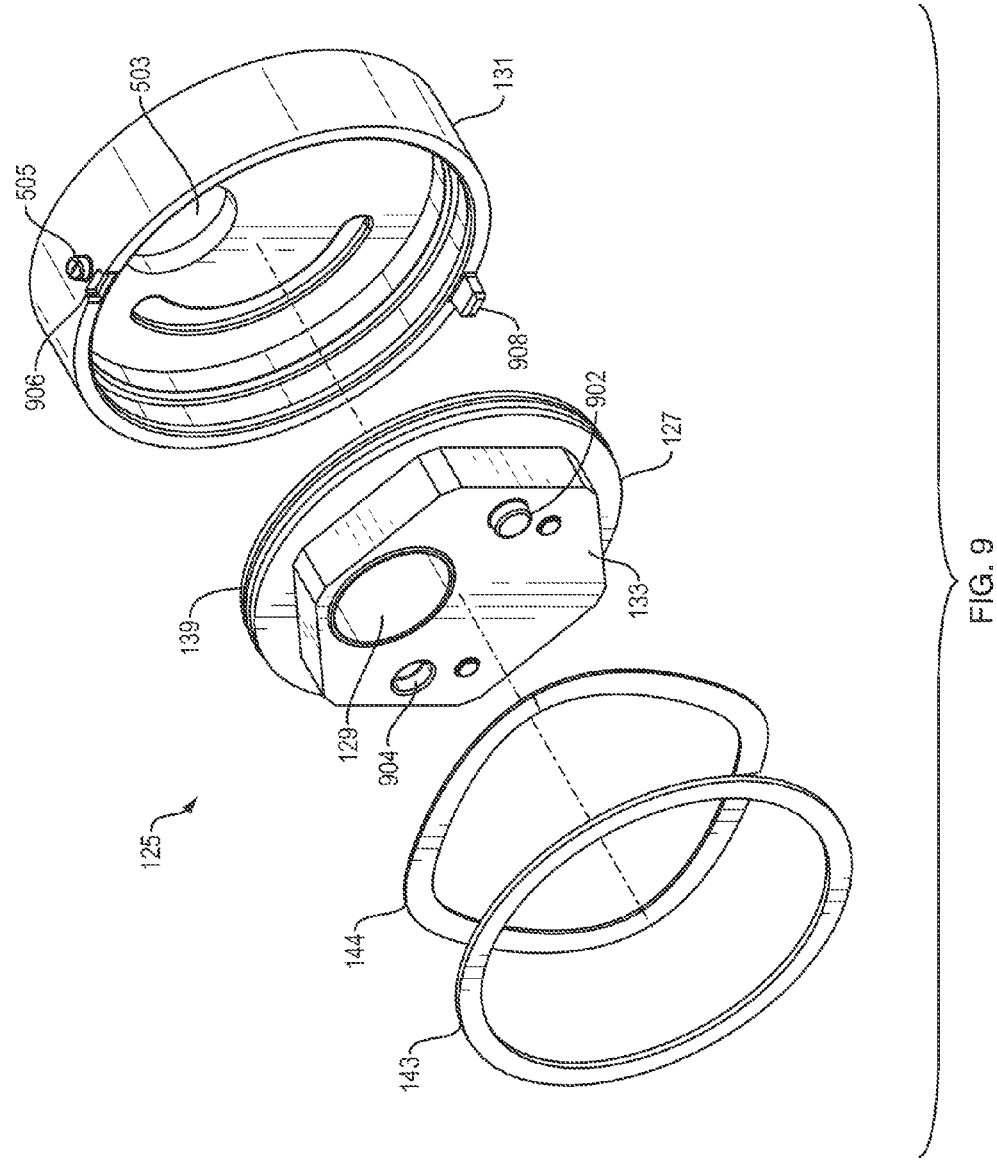
FIG. 9 shows the transfer coupling member including the housing of the transfer device of FIG. 1D in exploded perspective view.

As shown in FIG. 6, the disc 126 of the transfer coupling member 124 includes a boss or key 602 that is configured to fit into a corresponding hole or keyway 904 (FIG. 9) of the disc 127 of interface coupling member 125. As shown, the disc also includes a hole or keyway 604 to receive a corresponding boss or key 902 of the disc 127 of the interface coupling member 125. The housing 130 includes alignment elements 606 and 608 to align the housing 130 with a corresponding housing of the transfer device, e.g., housing 131 (FIG. 9). As shown, element 606 is a tab or key that fits into the slot or keyway 906 (FIG. 9) of the housing 131, and element 608 is a slot or keyway to receive tab or key 908 (FIG. 9) of the housing 131.

Figure 8A:
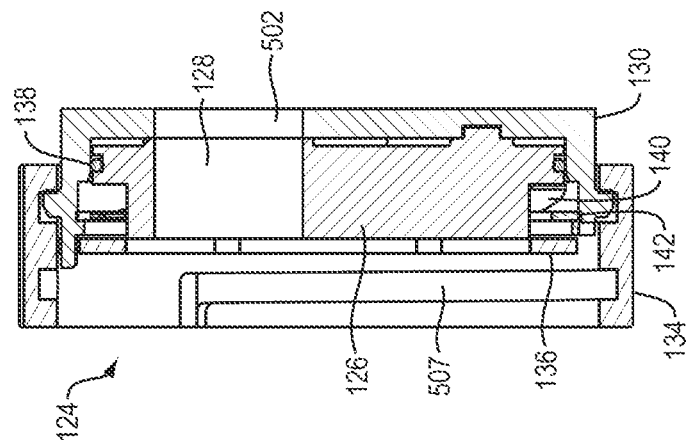
FIG. 8A is a cross-sectional view along line 8A-8A of FIG. 7A.
Figure 7A:
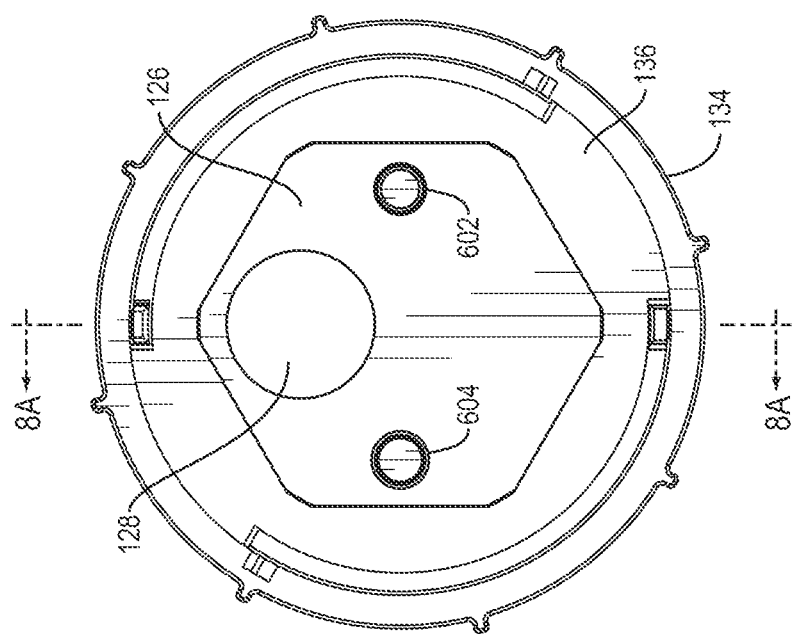
FIGS. 7A-7B are front views of the coupling member including the collar and the housing of FIG. 6 in coupled and uncoupled positions, respectively.

FIGS. 7A-7B and 8A-8C are respective front and cross-sectional views of the coupling member 124 positioned in the housing 130. In FIGS. 7A and 8A, the coupling member 124 is shown positioned in the housing 130 in the open position (see also FIG. 5C). The opening 128 of the disc 126 is aligned with the opening 502 of the housing 130. The snap ring 142 is configured to retain the disc in the housing 130, with the spring positioned between the snap ring 142 and a front surface of the disc 126. The snap ring 142 is configured to fit into a groove in the housing 130 as shown. The spring 140 pushes the disc 126 against the back of the housing 130. The configuration of snap ring 142, spring 140, and O-ring 138 allows the disc 126 to be rotatable in housing 130 while maintaining a seal between the disc and the housing.

Figure 8C:
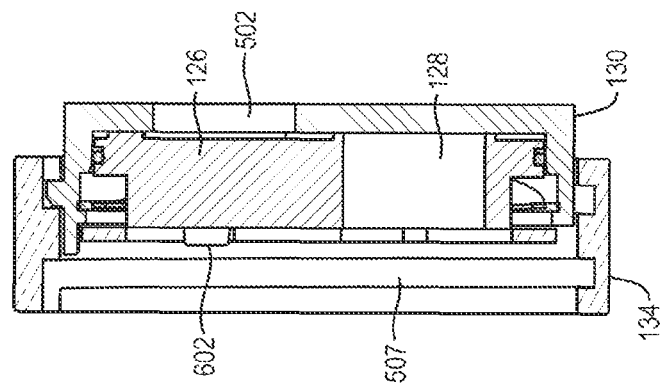
FIG. 8C is a cross-sectional view along line 8C-8C of FIG. 7B.
Figure 8B:
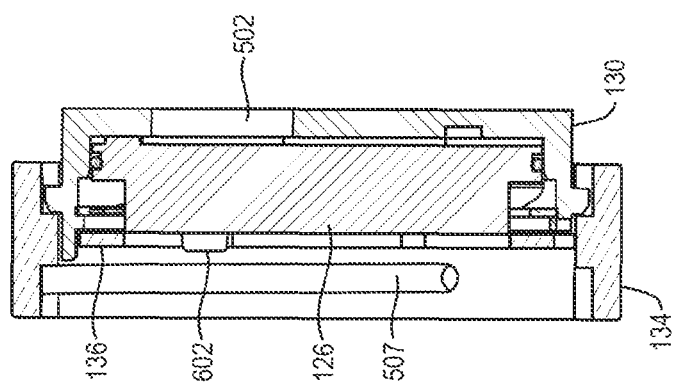
FIG. 8B is a cross-sectional view along line 8B-8B of FIG. 7B.
Figure 7B:
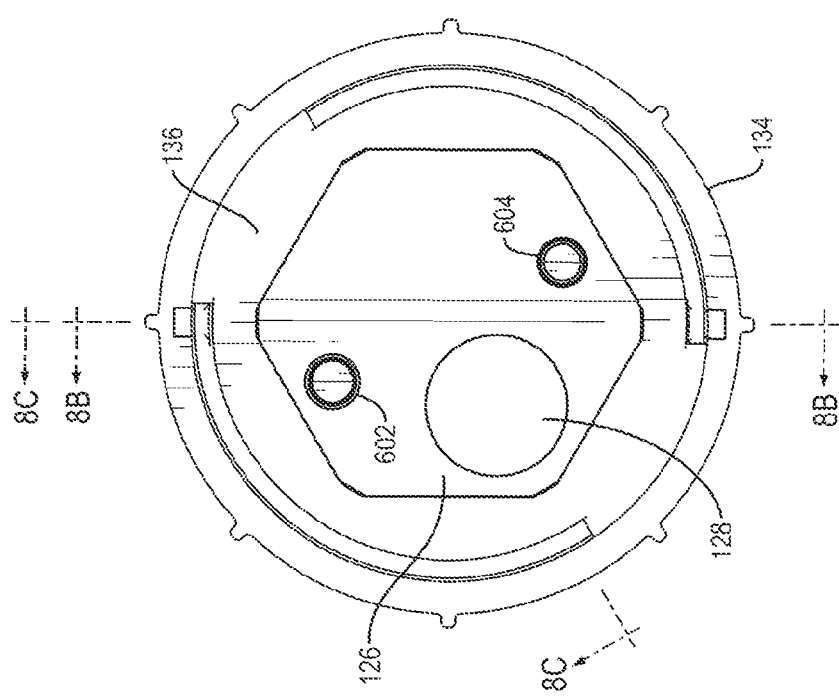

In FIGS. 7B and 8B-C, the coupling element 124 is shown positioned in the housing 130 in the closed position. The disc 126 is rotated such that the opening 128 is out of alignment with the opening 502 (FIG. 8C), the disc 126 thereby closing off access to the opening 502 from the front of the housing 130 (FIGS. 8B-C). As shown in FIG. 7B, the disc 126 is rotated counterclockwise by 135 degrees as compared to the open position shown in FIG. 7A. Collar 134, including flange 136, are also rotated by 135 degrees. It should be noted, however, that in this embodiment, rotation of the collar 134 as shown would not cause rotation of the disc 126, unless the disc was coupled to the disc 127 of the transfer device. This is so, because the flange 136 of the collar 134 does not engage disc 126, as can be seen, for example, in FIG. 8B. The closed position of the interface coupling member 124 shown in FIG. 7B corresponds to the closed position shown in FIG. 5A.

FIG. 9 shows the coupling member 125 and the housing 131 of the transfer device 104 of FIG. 1. The coupling member 125 includes the disc 127, the seal 139, the spring 141, and the snap ring 143. In this embodiment, the housing 131 is a cylinder having a front and a back, the front being open to receive the disc 127 and the back being closed, except for the opening 503. As shown, the seal 139 is an O-ring that is seated in a groove in the perimeter of the disc 127. When the disc 127 is positioned in the housing 131, the seal 139 provides a perimeter seal between the disc 127 and the housing 131 (see FIGS. 10A-C). Also shown is the boss or key 902 and the hole or keyway 904 to rotationally couple the disc 127 to the disc 126 of the interface coupling member 124.

Similar to the housing 130, the housing 131 includes alignment elements to facilitate alignment of the transfer device to the interface device and to prevent incorrect coupling of the devices. As shown in FIG. 9, the housing 131 includes alignment elements 906 and 908 to align the housing 131 with a corresponding housing of the transfer device, e.g., housing 130. As shown, element 906 is a tab or key that fits into the slot or keyway 606 (FIG. 6) of the housing 130, and element 908 is a slot or keyway to receive tab or key 608 (FIG. 6) of the housing 130.

Figure 11A:
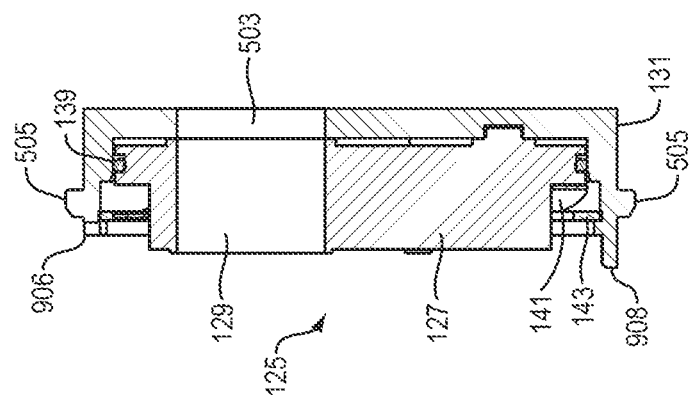
FIG. 11A is a cross-sectional view along line 11A-11A of FIG. 10A.
Figure 10A:
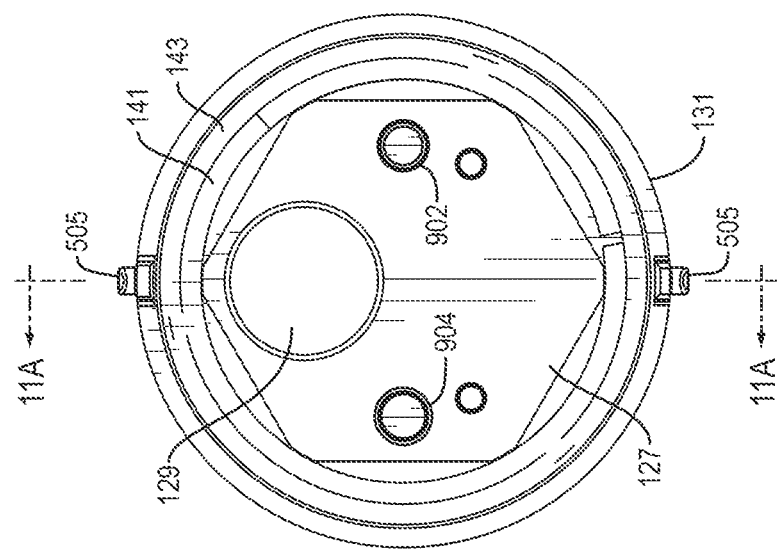
FIGS. 10A-10B are front views of the coupling member and housing of FIG. 9 in coupled and uncoupled positions, respectively.

FIGS. 10A-10B and 11A-11C are respective front and cross-sectional views of the coupling member 125 positioned in the housing 131. In FIGS. 10A and 11A, the coupling member 125 is shown positioned in the housing 131 in the open position (see also FIG. 5C). The opening 129 of disc 127 is aligned with the opening 503 of the housing 131. The snap ring 143 is configured to retain the disc 127 in the housing 131. As shown, the snap ring 143 fits into a groove of the housing 131. The spring 141 is positioned between the snap ring 143 and a front surface of the disc 127 to push the disc 127 against the back of the housing 131. The configuration of snap ring 143, spring 141, and O-ring 139 allows the disc 127 to be rotatable in housing 131 while maintaining a seal between the disc and the housing. This configuration is the same as that described above in reference to the disc 126 of FIG. 6.

Figure 11C:
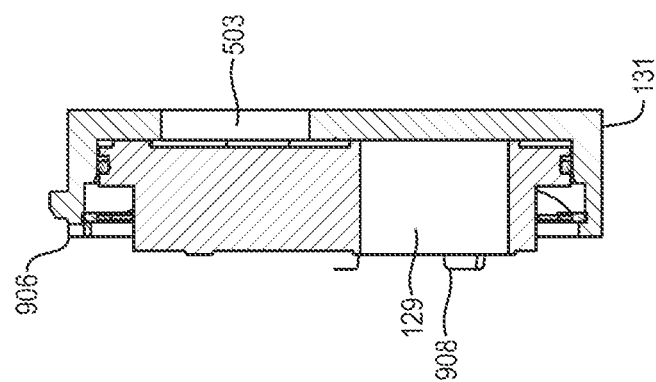
FIG. 11C is a cross-sectional view along line 11C-11C of FIG. 10B.
Figure 11B:
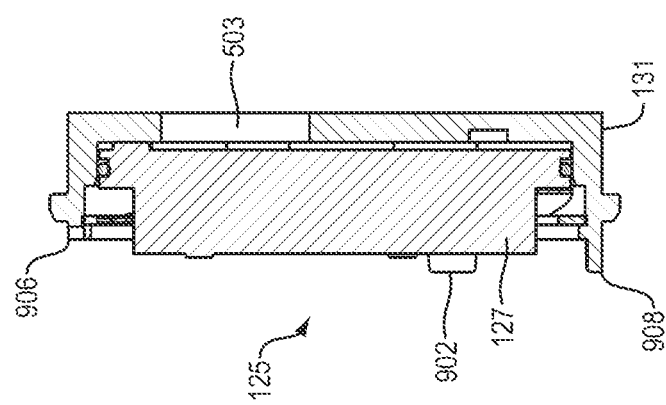
FIG. 11B is a cross-sectional view along line 11B-11B of FIG. 10B.
Figure 10B:
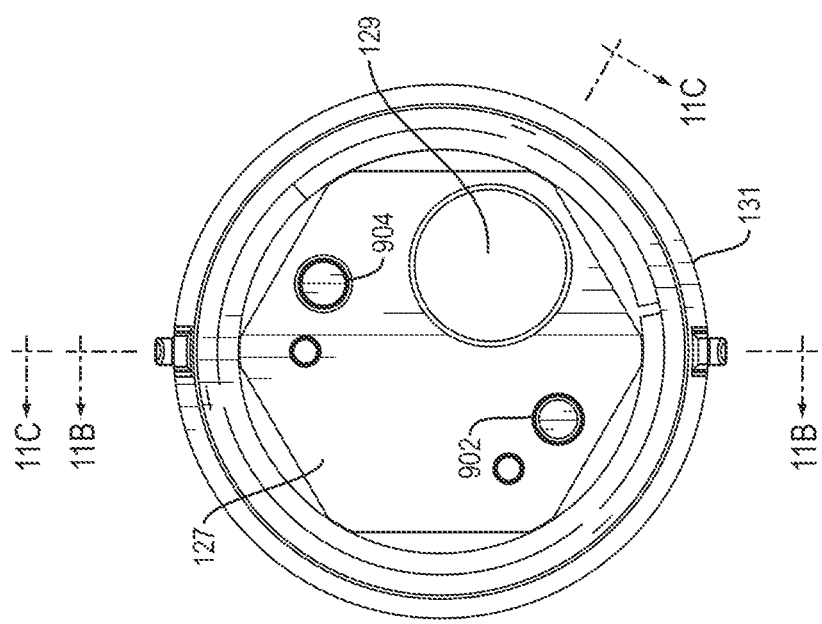

In FIGS. 10B and 11B-C, the coupling element 125 is shown positioned in the housing 131 in the closed position. The disc 127 is rotated such that the opening 129 is out of alignment with the opening 503 of the housing 131 (FIG. 11C), the disc 127 thereby closing off access to the opening 503 from the front of the housing 131 (FIGS. 11B-C). As shown in FIG. 10B, the disc 127 is rotated clockwise by 135 degrees as compared to the open position shown in FIG. 10A. The closed position of the transfer coupling member 125 shown in FIG. 11B corresponds to the closed position shown in FIG. 5A.

Figure 12:
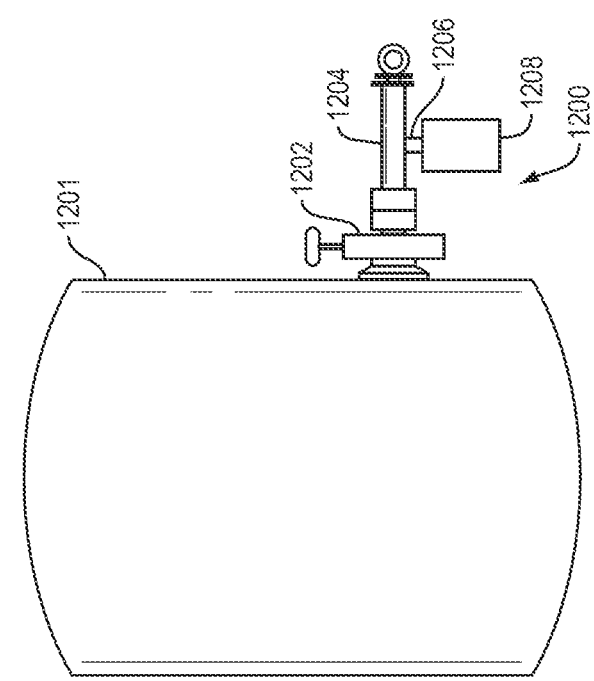
FIG. 12 shows an embodiment of the present invention in a contemplated use.

FIG. 12 shows an example system 1200 of the present invention in a contemplated use. An interface device 1202 of the system 1200 is mounted to a tank or bioreactor 1201. A transfer device 1204 of the system 1200 is coupled to the interface device 1202. The system 1200 can be operated as described herein for system 100 to transfer fluid between the tank or bioreactor 1201 and a container 1208 connected to the transfer port 1206 of the transfer device 1204. For example, one ore more samples may be collected from bioreactor 1201 into container 1208, which may be a collection bag. Furthermore, a first sample may be collected in the sample container 1208, which is then disconnected and replaced with a second sample container (not shown). A second sample is then collected into the second sample container.

Figure 13:
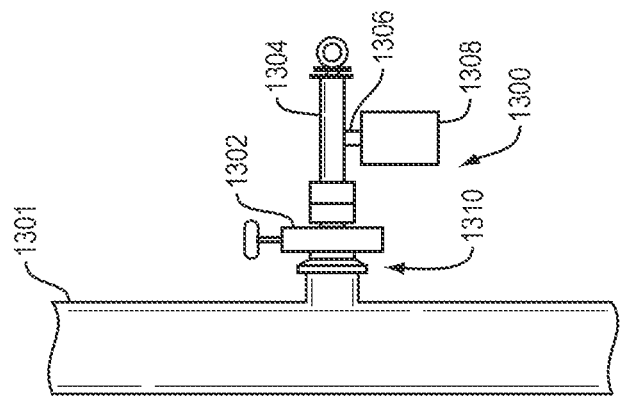
FIG. 13 shows an embodiment of the present invention in another contemplated use.

FIG. 13 shows an example system 1300 of the present invention in another contemplated use in which the reservoir is a pipe. An interface device 1302 of the system 1300 is mounted to a process stream 1301 via a pipe connection 1310. A transfer device 1304 of the system 1300 is coupled to the interface device 1302. A container 1308 is connected to the transfer port 1306 of the transfer device 1304. The system 1300 can be operated, as described herein for system 100, to transfer fluid between the process stream 1301 and the container 1308. For example, a fluid can be introduced into the process stream 1301 from the container 1308. Alternatively, fluid may be removed, e.g., sampled, from the process stream 1301 and collected in the container 1308.

FIG. 14 shows an example system 1400 of the present invention in a contemplated use. An interface device 1402 is mounted to a bioreactor 1401 in a manufacturing process. Any one of a plurality of devices 1404A, 1404B and 1410 may be coupled to the interface device 1402 of the system 1400 at a time during the process. For example, fluid transfer devices 1404A and 1404B can be coupled sequentially to the interface device 1402 to take sequential samples from the bioreactor 1401 into sample containers 1408A and 1408B. As in the example shown in FIG. 12, the sample containers 1408A and 1408B are connected to the respective transfer ports 1406A and 1406 of the transfer devices 1404A and 1404B. The interface device 1402 can also be used to couple the device 1410 to the bioreactor 1401, not to transfer fluid, but to provide the device 1410 with access to the process or product in the bioreactor. For example, the device 1410 may include a probe or sensor, such as a temperature probe or a pH sensor, which require access to the process or product in the bioreactor 1401.

FIGS. 15A-15H illustrate an interface device 1502 and FIGS. 16A-16H illustrate a transfer device 1604 of a fluid transfer system 1700 (FIGS. 17A-17G) according to another embodiment of the present invention. The system 1700 is in many aspects similar to the system 100 described above, in that the system includes coupling members having rotating discs and that the transfer device includes a transfer member that extends through the coupling members to cooperate with a sliding seal of the interface device. The system 1700, however, differs from system 100 in that the transfer member, for example, only includes two plungers that extend through the coupling members. In addition, system 1700 includes a rotating plunger interlock that prevents the plungers from being pushed forward until the discs of the coupling members are fully rotated into position. Another difference is that the system 1700 employs an outer tube or mount to selectively move one or both of the plungers. Other differences will become apparent from the description below.

Figure 15A:
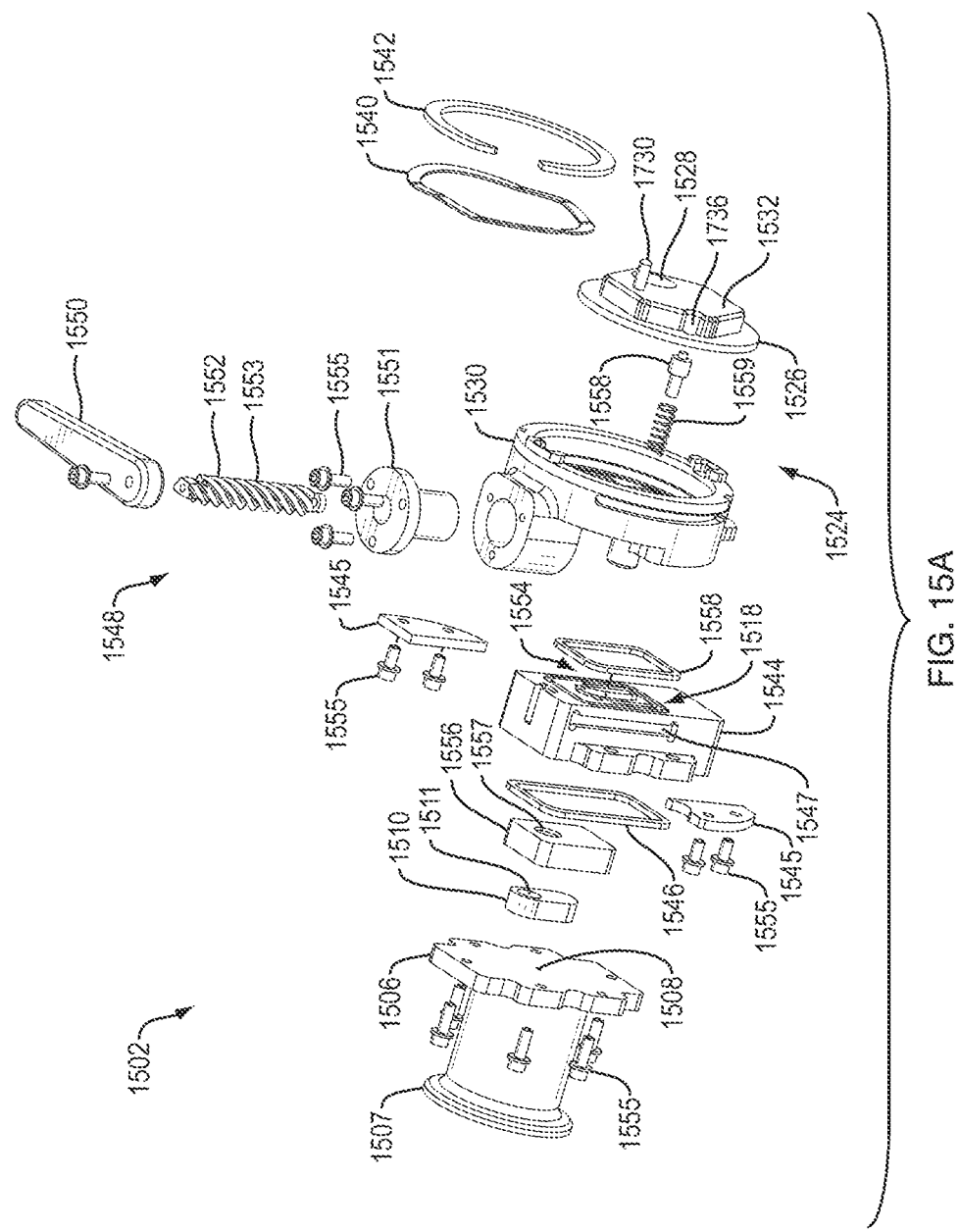
FIG. 15A shows an interface device according to another embodiment of the present invention in exploded view.

As shown in FIG. 15A, the interface device 1502 includes a mounting plate 1506 to mount the interface device 1502 to a reservoir, e.g., a bioreactor or stainless steel tank (not shown). The mounting plate 1506 includes the reservoir port 1508. As shown, the reservoir port 1508 is a circular opening that extends through the mounting plate 1506. The mounting plate 1506 includes a flange 1507 for mounting to an existing port of the reservoir. The flange 1507 can have standard dimensions to fit a standard port, such as a TC port, as shown, or an INGOLD® port.

The interface device 1502 includes a sealing element 1510 that is movable between an open position and a closed position. The sealing element 1510 closes the reservoir port 1508 when the sealing element is in the closed position. As shown, the sealing element is a linearly sliding valve that includes a hole 1511. Sliding the sealing element 1510 to bring the hole 1511 into alignment with the reservoir port 1508 opens the reservoir port (see also FIGS. 18A-G). Conversely, sliding the sealing element 1510 to bring the hole 1511 out of alignment with the reservoir port 1508 closes the reservoir port. The sealing element could also be a rotary sliding valve, for example.

As shown in FIG. 15A, the sealing element 1510 is positioned in a carrier or housing 1556 having a hole 1557 that is aligned with the hole 1511 of the sealing element. The interface device 1502 also includes a seal plate 1544 that is coupled to the mounting plate 1506 through use of screws 1555. The seal plate is configured to position the carrier 1556, and hence the sealing element 1510, proximate the reservoir port 1508. The carrier 1556 is slidably disposed in the seal plate 1544 (see FIG. 18A). A seal 1546 encircles the sealing element 1510 and carrier 1556 and is positioned between the seal plate 1544 and the mounting plate 1506. The seal 1546 is set in and carried by the seal plate 1544 (see FIG. 18A).

The interface device 1502 further includes an actuating mechanism 1548 mounted to the top of the housing 1530 to move the housing 1530 relative to the seal plate 1544 and the mounting plate 1506. As shown, the actuating mechanism 1548 includes a handle 1550 coupled to an actuation screw 1552 that is coupled to the seal plate 1544. The actuation screw 1552 includes a thread 1553 to engage a corresponding thread in nut 1551 which is mounted to housing 1530, e.g., via screws 1555. Preferably, the thread 1553 is a half-turn thread. An operator can use the handle 1550 to move the housing 1530 up or down relative to the seal plate 1544 and mounting plate 1506, to thereby move the sealing element 1510 between the open and closed positions. However, the sealing element 1510 will not move when the housing 1530 is moved up or down unless the transfer member is positioned in the hole 1511 of the sealing element to drive the sealing element up or down. While a manual actuating mechanism 1548 is illustrated in FIG. 15A, it should be understood that automatic actuation is within the scope of the present invention. Furthermore, any mechanical, pneumatic, hydraulic, magnetic, electromagnetic or other suitable mechanism may be used to move the housing 1530 relative to the mounting plate 1506.

Figure 16A:
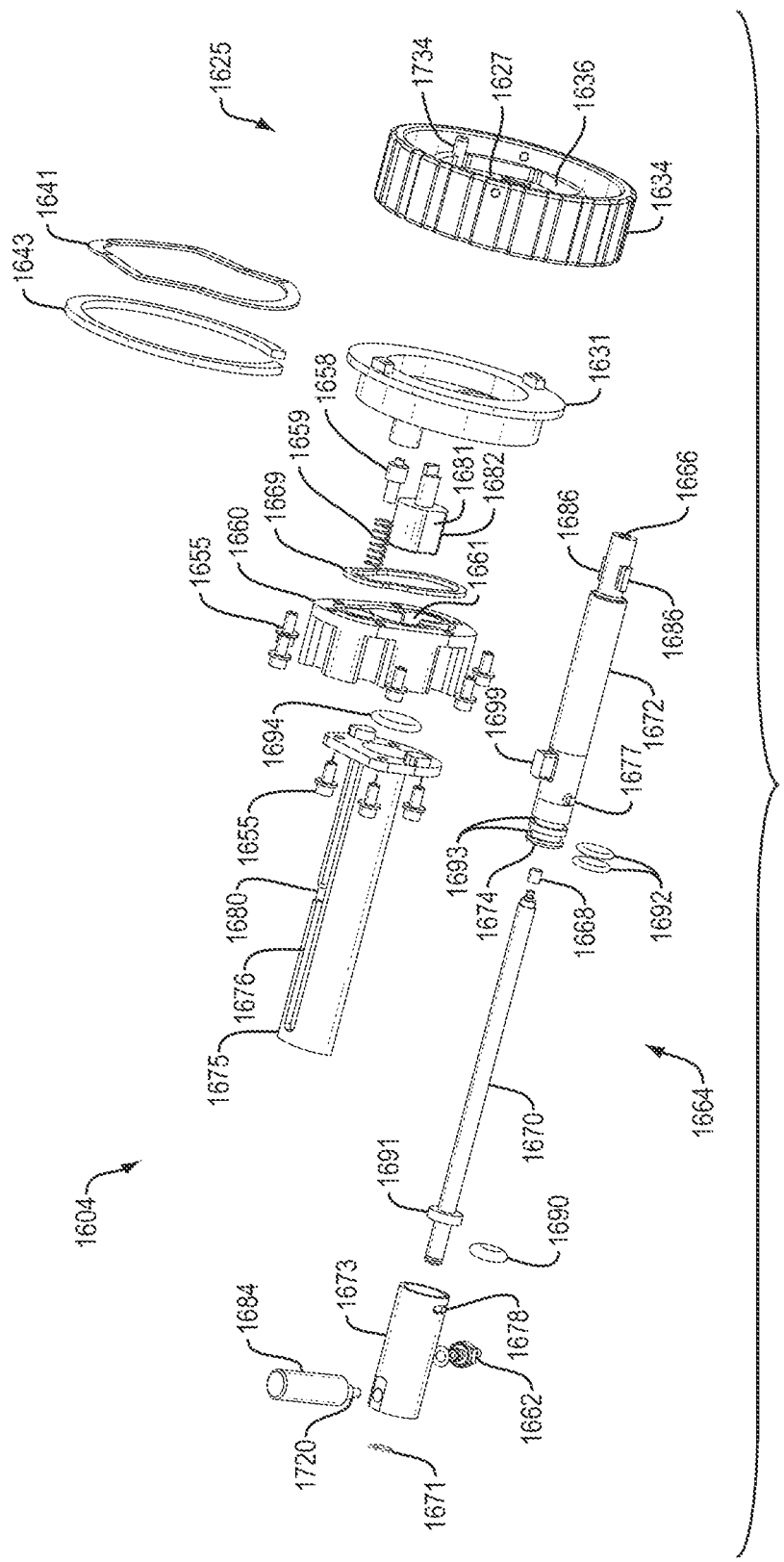
FIG. 16A shows a transfer device according to an embodiment of the present invention in exploded view.

As shown in FIG. 15A, the interface device 1502 includes an interface coupling element or member 1524 to couple to a transfer coupling element or member 1625 (FIG. 16A) of the transfer device 1604 (FIG. 16A). The interface coupling element is movable with the sealing element 1510. The interface coupling element 1524 is coupled to the housing 1530 which, in turn, is slidably coupled to the seal plate 1544 via brackets 1545. The brackets 1545 can be fastened to the housing 1530 via screws or bolts 1555, as shown. Each bracket 1545 engages a respective slot 1547 in seal plate 1544. However, the housing 1530 may be movably coupled to the seal plate 1544 by other suitable means. The housing 1530 and the seal plate 1544 cooperate to form a transfer member receptacle configured to receive a transfer member of a transfer device, e.g., the plunger assembly 1664 (FIG. 16A) of the transfer device 1604. As shown, seal plate 1544 includes a channel or opening 1554 that is configured to receive the plunger assembly 1664. A seal 1558, e.g., a wiper seal, is positioned between the seal plate 1544 and the housing 1530 and is set in and carried by the seal plate 1544 (see FIG. 18A). The seal 1558 encircles the opening 1554 of the seal plate.

Similar to the coupling elements 124 and 125 described in reference to FIGS. 1A-1D and 4A-5C, the interface coupling element 1524 and transfer coupling element 1625 cooperate to open or close a passage through the coupling elements. The open passage is configured to receive the transfer member, e.g., plunger assembly 1664.

As shown in FIGS. 15A-15B and FIGS. 16A-16B, the coupling elements 1524 and 1625 include respective discs 1526 and 1627, wave springs 1540 and 1641, and snap rings 1542 and 1643. The snap ring 1542 is configured to retain the disc 1526 in the housing 1530, with the spring 1540 positioned between the snap ring and a front surface of the disc 1526. The snap ring 1643 is configured to retain the disc 1627 in housing 1631. Similar to the discs 126 and 127 described in reference to FIGS. 1A-1D, the discs 1526 and 1627 include respective openings 1528 and 1629, and the coupling elements are configured to open and close a passage through the coupling elements with rotation of the discs. The discs 1526 and 1627 include respective mating faces 1532 and 1633 to rotationally couple the disc. A collar 1634 (FIGS. 16A-16B) coupled to disc 1627 includes a flange 1636 to engage the disc 1526 and to rotationally couple the collar 1634 to the discs, such that rotation of the collar 1634 causes rotation of the discs. In this embodiment, the collar 1634 and the disc 1627 can be formed in one piece. As shown, the flange 1636 includes a hexagonal opening that is configured to engage a corresponding hexagonal portion of the disc 1526.

As shown in FIG. 16A, the transfer device 1604 includes a body 1660 having a bore 1661 which extends through the length of the body 1660. The body 1660 is connected at one end to a guide element 1675 and at the other end to housing 1631 that is configured to receive the disc 1627. As shown, the body 1660 is connected to the housing 1631 and guide element 1675 via screws 1655, but may be connected or attached to the housing or the guide element by other suitable means. Alternatively, the body 1660 and the housing 1631, the body and the guide element 1675, or all of them together may be formed in one piece. A seal 1669 is positioned between the body 1660 and the housing 1631 and is set in and carried by the body 1660. Slidably disposed in the bore 1661 of body 1660 is the transfer member or plunger assembly 1664 (see FIG. 18A). As shown, the plunger assembly 1664 includes an inner plunger 1670, an outer plunger 1672, and an outer tube or handle mount 1673. The back end of the inner plunger 1670 is coupled to the handle mount 1673 via a snap ring 1671. This coupling locks the handle mount and inner plunger in translation but allows for relative rotation of the handle mount with respect to the inner plunger. A transfer port 1662 is provided on the handle mount 1673. The plunger assembly 1664 is operable to provide a fluid path between the front plunger port 1666 and the transfer port 1662.

The plunger assembly 1664 cooperates with the sealing element 1510 (FIG. 15A) of the interface device 1502 to allow transfer of fluid into or out of a reservoir through the fluid path when the sealing element 1510 is in the open position. The interface device 1502 is operable to move the plunger assembly 1664, and hence the front plunger port 1666, with movement of the sealing element 1510 to align the front plunger port 1666 with the reservoir port 1508.

The interface device 1502 includes a transfer member locking element, e.g., plunger assembly locking element 1518 at seal plate 1544, to prevent movement of the front plunger port 1666 (FIG. 16A) of the transfer device away from the reservoir port 1508 when the sealing element is in the open position. The plunger assembly locking element 1518 includes ramps 1520 (FIGS. 18N and 18R) to engage wings 1686 (FIGS. 16A and 18N) of the plunger assembly 1664. Once the plunger assembly 1664 has been inserted into the interface device 1502 and moved down, the ramps 1520 engage the wings 1686 and keep the plunger assembly 1664 from being pulled out of the interface device 1502, as is further described in reference to FIG. 18R.

Returning to FIG. 16A, the plunger assembly 1664 includes a valve member 1668 that is movable between an open position and a closed position to control flow of fluid through the front plunger port 1666. The inner plunger 1670 is slidably disposed in bore 1674 of the outer plunger 1672. The inner plunger, which is coupled to a handle 1684 via the handle mount 1673, is operable to move the valve member 1668 between the open and closed positions. As shown, the front plunger port 1666 is provided at the front of the outer plunger 1672. The outer plunger 1672 is slidably disposed in bore 1661 of the body 1660 of the transfer device 1604. The outer plunger 1672 is configured to extend through the coupling members 1625 and 1524 (FIG. 15A) and into the interface device 1502, as will be described below. The system 1700 is configured to provide an air gap between the outer plunger 1672 and the coupling elements to minimize exposure of the outer and inner plungers to non-sterile or 'dirty' surfaces, e.g., the mating faces 1532 and 1633 of the coupling elements 1524 and 1625. The outer plunger 1672 is configured to cooperate with the inner plunger 1670 to provide a fluid path for the transfer of fluid. The inner plunger 1670 is configured to cooperate with the outer plunger 1672 to provide valving.

As shown in FIG. 16A, the transfer device 1604 includes guides 1676 and 1678 to limit movement of the outer plunger 1672 and outer tube or handle mount 1673 relative to each other and to the guide element 1675. A guide 1680 limits movement of the inner plunger 1670 relative to the outer plunger 1672 when the inner plunger is operated to open and close the front plunger port 1666. In the embodiment shown, the guides comprise slots that cooperate with pins to limit length of travel and to limit or prevent rotation. For example, guide 1678 comprises slot on the outer tube or handle mount 1673 that cooperates with a pin 1677 on outer plunger 1672. As shown, the guide 1676 includes a slot in the guide element 1675 that cooperates with a pin or tab 1699 on the outer plunger 1672. The slot of the guide element 1675 limits travel and prevents rotation of the pin 1699 in the slot, thereby limiting travel and preventing rotation of the outer plunger 1672 relative to the body 1660. Further, pin 1699 is sized so that it can travel in slot 1676 but cannot enter slot 1680 (see FIGS. 16B and 17A).

The transfer device 1604 can maintain a sterile path for the fluid being transferred. To that end, the transfer device 1604 includes one or more seals configured to provide a sterile barrier between the fluid path and the environment. As shown in FIG. 16A, the transfer device 1604 includes seals 1690, 1692 and 1694, which, in this embodiment, are O-rings. The inner plunger 1670 includes a flange 1691 to seat the seal 1690. The outer plunger 1672 and housing 1660 each include respective grooves or channels 1693 and 1695 (FIG. 18A) to seat the respective seals 1692 and 1694. Additional seals may be provided as described herein.

FIGS. 17A-17G are top views of the system 1700 including the interface device 1502 of FIG. 15A and the transfer device 1604 of FIG. 16A illustrating the process of operating the system 1700, e.g., to transfer fluid into or out of a reservoir as described herein. FIGS. 18A-18G are sectional views of the devices of FIG. 15A and FIG. 16A corresponding to the top views of FIGS. 17A-17G.

In FIGS. 17A and 18A, the interface device 1502 and transfer device 1604 of the system 1700 are shown in uncoupled and closed positions. The reservoir valve or sliding seal 1510 is in the closed position sealing the reservoir port 1508. As shown, the hole 1511 of the sliding seal 1510 is out of alignment with the reservoir port 1508 to close the reservoir port. The sealing element 1510 and the mounting plate 1506 can define a steam cleanable surface 1702 that is exposed to the inside of the reservoir when the sealing element is in the closed position.

As shown in FIGS. 17B and 18B, the fluid transfer member of the transfer device 1604, i.e. the plunger assembly 1664, has been aligned with the interface device 1502. The transfer coupling member 1625 of the transfer device 1604 is coupled to the interface coupling member 1524 of the interface device 1502. The mating faces 1532 and 1633 (FIGS. 17A and 18A) of the discs 1526 and 1627 butt against each other and the discs are rotationally coupled. The discs, however, have not been rotated and their openings 1528, 1629 (FIGS. 15A and 16A) are not aligned with the transfer device 1604 or the interface device 1502. Thus, there is no passage through the coupling members 1524 and 1625 to receive the transfer member, i.e., the plunger assembly 1664. The fluid transfer member receptacle of the interface device 1502, i.e. the seal plate 1544, is closed, as is the body 1660 of the transfer device 1604.

The alignment and rotation of the discs 1526 and 1627 of the coupling members 1524 and 1625, respectively, is similar to that of discs 126 and 127 described above in reference to FIGS. 4A-C and 5A-C. However, the coupling members in this embodiment include respective disc locking members to prevent rotation of the discs until the discs are coupled to each other and the disc locking members are released. As shown in FIGS. 16A and 18A, the disc locking member of the transfer device 1604 includes a pin 1658 that is biased by a spring 1659 into a hole 1732 (FIG. 18A) of disc 1627 to prevent rotation of the disc 1627 relative to the housing 1631. The spring-loaded pin 1658 is displaceable by a boss or pin 1730 protruding from the mating face 1532 of the interface coupling member 1526 (see also FIG. 15B). As shown in FIG. 15A, the disc locking member of the interface device 1502 includes a pin 1558 that is biased by a spring 1559 into a hole 1736 (see FIGS. 15A, 15H) of the disc 1526 to prevent rotation of the disc 1526 relative to housing 1530. The spring-loaded pin 1558 is displaceable by a boss 1734 (see FIGS. 16A, 16H) protruding from the mating face 1633 of the transfer coupling member 1627. Thus, when coupled together, the interface coupling member 1524 releases the disc locking member of the transfer device 1604 and the transfer coupling member 1625 releases the disc locking member of the interface device 1502. This safety feature prevents accidental rotation of either of the discs 1526 and 1627, thereby preventing unwanted opening of the transfer device or the interface device.

In FIGS. 17C and 18C, the openings in the discs 1526 and 1627 are aligned with the transfer member, i.e., plunger assembly 1664. The discs 1526 and 1627, which are rotationally coupled, are rotated using collar 1634 to bring the respective openings 1528 and 1629 into alignment with the fluid transfer member receptacle 1544 and the fluid transfer member 1664, thereby creating a passage through which the fluid transfer member can be extended. The outer plunger 1672 is configured to extend through the openings 1528 and 1629, preferably without contacting the respective discs 1526 and 1627 of coupling members 1524 and 1625, whose mating surfaces 1532 and 1633 were exposed to the environment prior to coupling the devices. As shown in FIG.

18N, the system 1700 is configured to maintain an air gap 1708 when the outer plunger 1672 is extended through the openings 1528 and 1629, the air gap separating the outer plunger 1672 from the discs 1526 and 1627 of respective coupling members 1524 and 1625. The purpose of the air gap is to avoid contact with potentially contaminated surfaces.

The transfer device 1604 includes a plunger locking element or interlock 1682. The interlock 1682 prevents the operator from advancing the transfer member, e.g., the outer plunger 1672, relative to the body 1660 and toward the disc 1627 of the transfer coupling element when the transfer device 1604 is not coupled to the interface device and when the disc 1627 has not been rotated to align the opening 1629 with the bore of the transfer device. As shown in FIGS. 16A and 18H-18J, the plunger interlock 1682 is a cylindrical element that has a longitudinal cutout or groove 1681 and that is seated in the body 1660 of the transfer device 1604. The plunger interlock 1682 is rotationally coupled to disc 1627 via a keyed rod. In the locked state (FIGS. 18A and 18H), the cutout 1681 is out of alignment with the outer plunger 1672 and the interlock 1682 partially blocks the bore 1661 of the transfer device. When the disc 1627 is rotated to align the opening 1629 with the transfer member, the interlock 1682 rotates with the disc, thereby aligning the cutout 1681 of interlock 1682 with the outer plunger 1672 and the bore 1661 to allow the outer plunger to pass by the interlock (FIGS. 18C and 18J).

In FIGS. 17D and 18D, the inner and outer plungers 1670 and 1672 have been advanced into the interface device 1502 by pushing the handle 1684 toward the interface device 1502. As shown, the inner and outer plungers 1670 and 1672 extend through the hole 1511 of the sliding seal 1510.

In FIGS. 17E and 18E, the reservoir valve, i.e. sliding seal, 1510 is actuated. With the inner and outer plungers 1670 and 1672 positioned in the fluid transfer member receptacle 1544, the reservoir valve 1510 is actuated to open the reservoir port 1508 to the fluid transfer member receptacle 1544. In this embodiment, the valve is actuated by sliding the sliding seal 1510 linearly using actuating mechanism 1548. An operator can turn the actuation screw 1552 via handle 1550 to move the housing 1530 down relative to the seal plate 1544. Because the housing 1530 has been coupled to the transfer device 1604 via coupling members 1525 and 1626, moving the housing 1530 moves the transfer device 1604 including in the inner and outer plungers 1670 and 1672. The plunger 1672 drives the sliding seal 1510 down to align the hole 1511 and the inner and outer plungers 1670, 1672 with the reservoir port 1508. Although the hole 1511 is now aligned with the reservoir port 1508, the seal 1668 of the plunger assembly 1664 seals the reservoir port 1508. As shown, the seal 1668 is positioned at the front end of inner plunger 1670 and within the outer plunger 1672 (see also FIG. 18K).

When the outer plunger 1672 is driven down by the actuation mechanism 1548, the transfer member locking element 1518 retains the outer plunger 1672 of the transfer member in position, as shown in FIGS. 18P and 18R. As the outer plunger is pushed down, the wings 1686 ride against ramps 1520 of the locking element 1518. The ramps 1520 push the wings 1686, and hence the outer plunger 1672, forward into the sealing element 1510 and against the reservoir port 1508. This preloads the outer plunger 1672 against the sealing element 1510 and the reservoir port 1508 to ensure a tight seal. This also reduces the amount of fluid that could build up in front of the front plunger port 1666 of the plunger assembly. When the reservoir port 1508 is open, the ramps 1520 of the transfer member locking element 1518 retain the outer plunger 1672 in position in the fluid transfer member receptacle, i.e., seal plate 1544, of the interface device 1502. This feature prevents accidental withdrawal of the outer plunger 1672, e.g., through operator error, and contributes to maintaining integrity of the fluid path during the transfer of fluid.

In FIGS. 17F and 18F, the handle 1684 and handle mount 1673 have been rotated relative to the guide element 1675, the inner plunger 1670, and the outer plunger 1672. The pin 1720 of handle 1684 is now positioned in slot 1716. Rotation of the handle mount 1673 has released the pin 1677 (FIG. 16A) of outer plunger 1672 from the guide slot 1678 (FIG. 16A) of the handle mount 1673, releasing the handle mount from outer plunger 1672. The handle mount can now slide back and forth relative to the outer plunger 1672. Because the inner plunger 1670 remains coupled to the handle mount 1673, an operator to use handle 1684 to move the inner plunger 1670 away from the reservoir port, as will be described below. In FIG. 18F, the inner plunger 1670 has not yet been moved away from the reservoir port 1508 and the reservoir port and the front plunger port 1666 are closed, as can be more clearly seen in FIG. 18K, which is an expanded view of the reservoir port 1508 and front plunger port 1666 of FIG. 18F.

In FIGS. 17G and 18G, the inner plunger 1670 is moved away from the reservoir port 1508 and the reservoir port is opened. For example, an operator can pull on handle 1684 to move the inner plunger 1670 away from the reservoir port 1508, thereby moving the seal 1668 away from the reservoir port, which opens the reservoir port. Guide 1680 limits movement of the inner plunger 1670. As shown, the guide 1680 comprises a slot 1718 in guide element 1675 that cooperates with the pin 1720 (FIG. 16A) on the handle 1684. Opening the reservoir port 1508 with the inner plunger 1670 provides a fluid path from the reservoir port 1508 to the transfer port 1662 as described below in reference to FIG. 18L.

FIG. 18L is an expanded view of the reservoir port 1508 and front plunger port 1666 of FIG. 18G showing the opened reservoir port and front plunger port. The seal 1668 is a valve member that cooperates with valve seat 1724 of the mounting plate 1506 of the interface device to open and close the reservoir port 1508. In addition, the seal 1668 and the outer plunger 1672 also form a valve to open and close the front plunger port 1666 of the plunger assembly 1664. As shown, the seal 1668 is also a valve member that cooperates with valve seat 1722 of the outer plunger 1672. The seal 1668 forms a radial, shear seal with the valve seat 1722. The shear seal can avoid particles, e.g., platelets, to get caught in the valve member and the valve seat. Moving the seal 1668 away from the reservoir port 1508 (and out of the valve seat 1722) opens the front plunger port 1666, thereby allowing flow of fluid through the fluid path. Fluid can now flow from the reservoir port 1508 to the transfer port 1662 (FIG. 18G), or vice versa, through a channel 1710, defined by the inner and outer plungers 1670 and 1672. As shown, the channel 1710 comprises a channel or groove along a length of the inner plunger 1670 that provides a space for fluid flow between the inner plunger 1670 and an inside of the outer plunger 1672.

Returning to FIG. 18G, the seals or O-rings 1690 of the outer plunger 1672 are spaced apart far enough to prevent over-wipe when the handle mount 1673 moves with respect the outer plunger 1672. Preventing over-wipe contributes to the maintenance of a sterile fluid path.

Once the transfer of fluid is complete, the inner plunger 1670 can be pushed back towards the reservoir port 1508 to stop the flow of fluid through the front plunger port 1666 and to seal the reservoir port with seal 1668. The reservoir valve 1510 can then be actuated to close the reservoir port from the fluid transfer receptacle 1544 by moving the sliding seal 1510 up using actuating mechanism 1548. The plunger assembly 1664 can be withdrawn from the fluid transfer member receptacle and the interface device 1502. Once the plunger assembly 1664 is withdrawn, the discs 1526 and 1627 can be rotated back to close both the fluid transfer member receptacle 1544 of the interface device and the body 1660 of the transfer device.

FIGS. 19A-19H illustrate an interface device 1902 and FIGS. 20A-20H illustrate a transfer device 2004 of a fluid transfer system 2100 (FIGS. 21A-21F) according to another embodiment of the present invention. The system 2100 is in many aspects similar to the systems 100 and 1700 described above, in that the system includes coupling members having rotating discs and that the transfer device includes a transfer member that extends through the coupling members to cooperate with a sliding seal of the interface device. The system 2100, however, differs from system 100 in that the transfer member, for example, only includes two plungers that extend through the coupling members, similar to the fluid transfer system 1700 described above. Also, as described above in connection with transfer system 1700, system 2100 includes a rotating plunger interlock that prevents the plungers from being pushed forward until the discs of the coupling members are fully rotated into position. System 2100 differs from system 1700 in that system 2100 includes an improved actuating mechanism that includes a cam for vertical motion and another cam for horizontal motion. A user can rotate a single handle of the actuation mechanism of system 2100 to move the sliding valve vertically and to open the flow control valve through horizontal motion of an inner plunger. This simplifies use of the system by an operator and ensures proper timing of the motions of the various valves and seals. Other differences will become apparent from the description below.

Figure 19A:
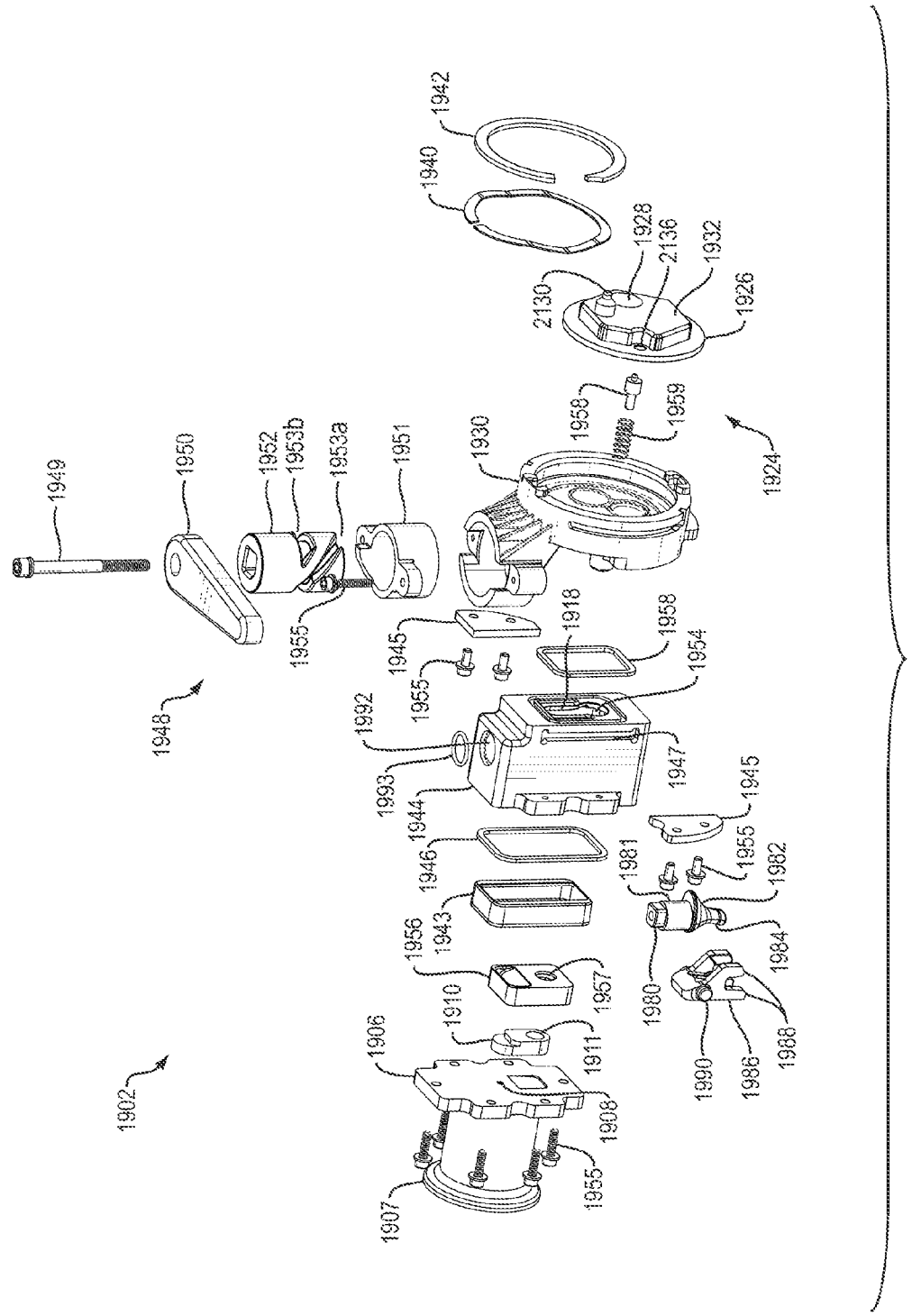
FIG. 19A shows an interface device according to another embodiment of the present invention in exploded view.

As shown in FIG. 19A, interface device 1902 includes a mounting plate 1906 to mount the interface device to a reservoir, e.g., a bioreactor or stainless steel tank (not shown). The mounting plate 1906 includes a reservoir port 1908. As shown, the reservoir port 1908 is a circular opening that extends through the mounting plate 1906. The mounting plate 1906 includes a flange 1907 for mounting to an existing port of the reservoir. The flange 1907 can have standard dimensions to fit a standard port, such as a TC port, as shown, or an INGOLD® port.

The interface device 1902 includes a sealing element 1910 that is movable between an open position and a closed position. The sealing element 1910 closes the reservoir port 1908 when the sealing element is in the closed position. As shown, the sealing element is a linearly sliding valve that includes a hole 1911. Sliding the sealing element 1910 to bring hole 1911 into alignment with the reservoir port 1908 opens the reservoir port (see also FIGS. 22G, 22I, 22Q and 22U). Conversely, sliding the sealing element 1910 to bring the hole 1911 out of alignment with the reservoir port 1908 closes the reservoir port. The sealing element could also be a rotary sliding valve, for example.

As shown in FIG. 19A, the sealing element 1910 is positioned in a carrier or housing 1956 having a hole 1957 that is aligned with the hole 1911 of the sealing element. The interface device 1902 also includes a seal plate 1944 that is coupled to the mounting plate 1906 through use of screws 1955. The seal plate is configured to position the carrier 1956, and hence the sealing element 1910, proximate the reservoir port 1908. The carrier 1956 is slidably disposed in a frame 1943 that fits into the seal plate 1944 (see FIG. 22A). A seal 1946 encircles the sealing element 1910 and carrier 1956 and is positioned between the seal plate 1944 and the mounting plate 1906. The seal 1946 is set in and carried by the seal plate 1944 (see FIGS. 22A and 22U).

The interface device 1902 further includes a housing 1930 and an actuating mechanism 1948 mounted to the top of the housing 1930 to move the housing relative to the seal plate 1944 and mounting plate 1906. As shown, the actuating mechanism 1948 includes a handle 1950 coupled to a cam mechanism (axial cam 1952, radial cam 1980) that is coupled to the seal plate 1944. Radial cam 1980 includes a shaft 1981 that extends through hole 1992 in seal plate 1944 and that is coupled to axial cam 1952 and handle 1950 via screw 1949. Seal plate 1944 carries an O-ring 1993 at opening 1992 to provide a seal. The axial cam 1952 includes a thread 1953a to engage a corresponding cam follower (e.g., tooth) in cam insert 1951 which is mounted to housing 1930, e.g., via screws 1955. Preferably, the thread 1553a is a quarter-turn thread. An operator can use the handle 1550 to move the housing 1930 up or down relative to the seal plate 1944 and mounting plate 1906, to thereby move the sealing element 1910 between the open and closed positions. However, the sealing element 1910 will not move when the housing 1930 is moved up or down unless the transfer member is positioned in the hole 1911 of the sealing element to drive the sealing element up or down. While a manual actuating mechanism 1948 is illustrated in FIG. 19A, it should be understood that automatic actuation is within the scope of the present invention. Furthermore, any mechanical, pneumatic, hydraulic, magnetic, electromagnetic or other suitable mechanism may be used to move the housing 1930 relative to the mounting plate 1906.

Figure 20A:
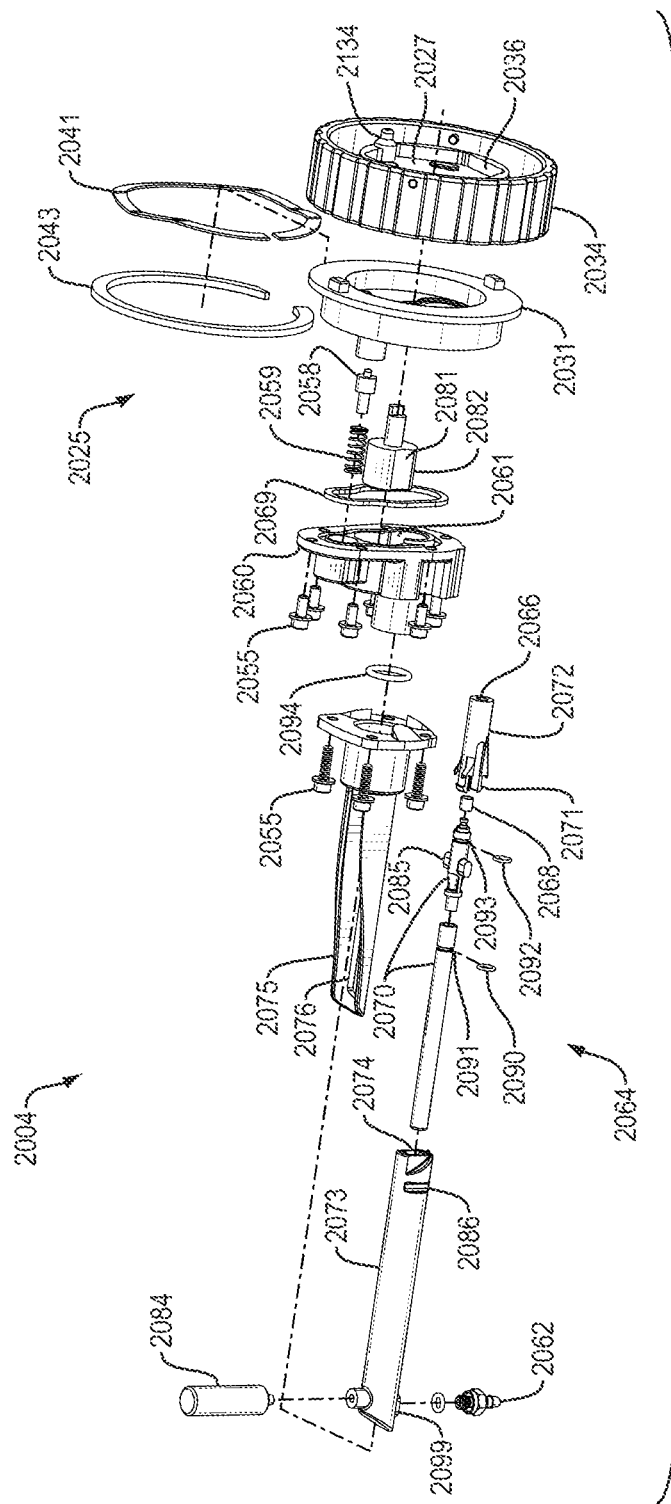
FIG. 20A shows a transfer device according to an embodiment of the present invention in exploded view.

As shown in FIG. 19A, the interface device 1902 includes an interface coupling element or member 1924 to couple to a transfer coupling element or member 2025 (FIG. 20A) of the transfer device 2004 (FIG. 20A). The interface coupling element is movable with the sealing element 1910. The interface coupling element 1924 is coupled to the housing 1930 which, in turn, is slidably coupled to the seal plate 1944 via brackets 1945. The brackets 1945 can be fastened to the housing 1930 via screws or bolts 1955, as shown. Each bracket 1945 engages a respective slot 1947 in seal plate 1944. However, the housing 1930 may be movably coupled to the seal plate 1944 by other suitable means. The housing 1930 and the seal plate 1944 cooperate to form a transfer member receptacle configured to receive a transfer member of a transfer device, e.g., the plunger assembly 2064 (FIG. 20A) of the transfer device 2004. As shown, seal plate 1944 includes a channel or opening 1954 that is configured to receive the plunger assembly 2064. A seal 1958, e.g., a wiper seal, is positioned between the seal plate 1944 and the housing 1930 and is set in and carried by the seal plate 1944 (see FIGS. 22A and 22U). The seal 1958 encircles the opening 1954 of the seal plate.

Similar to the coupling elements 124 and 125 described in reference to FIGS. 1A-1D and 4A-5C and coupling elements 1524 and 1625 of system 1700, the interface coupling element 1924 and transfer coupling element 2025 cooperate to open or close a passage through the coupling elements. The open passage is configured to receive the transfer member, e.g., plunger assembly 2064.

As shown in FIGS. 19A-19B and FIGS. 20A-20B, the coupling elements 1924 and 2025 include respective discs 1926 and 2027, wave springs 1940 and 2041, and snap rings 1942 and 2043. The snap ring 1942 is configured to retain the disc 1926 in the housing 1930, with the spring 1940 positioned between the snap ring and a front surface of the disc 1926. The snap ring 2043 is configured to retain the disc 2027 in housing 2031. Similar to the discs 126 and 127 described in reference to FIGS. 1A-1D, the discs 1926 and 2027 include respective openings 1928 and 2029, and the coupling elements are configured to open and close the passage with rotation of the discs. The discs 1926 and 2027 include respective mating faces 1932 and 1933 to rotationally couple the disc. A collar 2034 (FIGS. 20A-20B) coupled to disc 2027 includes a flange 2036 to engage the disc 1926 and to rotationally couple the collar 2034 to the discs, such that rotation of the collar 2034 causes rotation of the discs. In this embodiment, the collar 2034 and the disc 2027 can be formed in one piece. As shown, the flange 2036 includes a hexagonal opening that is configured to engage a corresponding hexagonal portion of the disc 1926.

As shown in FIG. 20A, the transfer device 2004 includes a body 2060 having a bore 2061 which extends through the length of the body 2060. The body 2060 is connected at one end to a guide element 2075 and at the other end to housing 2031 that is configured to receive the disc 2027. As shown, the body 2060 is connected to the housing 2031 and guide element 2075 via screws 2055, but may be connected or attached to the housing or the guide element by other suitable means. Alternatively, the body 2060 and the housing 2031, the body and the guide element 2075, or all of them together may be formed in one piece. As shown, a seal 2069 is positioned between the body 2060 and the housing 2031 and is set in and carried by the body 2060. Slidably disposed in the bore 2061 of body 2060 is the transfer member (i.e., plunger assembly) 2064 (see FIG. 22A). As shown, the plunger assembly 2064 includes a two-part inner plunger 2070, an outer plunger 2072, and an outer tube or handle mount 2073. The back end of the outer plunger 2072 is coupled to outer tube 2073 via a snap fit 2071. The front end of outer plunger 2072 includes front plunger port 2066. A transfer port 2062 is provided on outer tube 2073 of the plunger assembly. As shown, the transfer port 2062 includes a barb fitting that is attached to the outer tube 2073. An O-ring between the barb fitting the tube 2073 provides a sealing attachment. The plunger assembly 2064 is operable to provide a fluid path between the front plunger port 2066 and the transfer port 2062.

The plunger assembly 2064 cooperates with the sealing element 1910 (FIG. 19A) of the interface device 1902 to allow transfer of fluid into or out of a reservoir through the fluid path when the sealing element 1910 is in the open position. The interface device 1902 is operable to move the plunger assembly 2064, and hence the front plunger port 2066, with movement of the sealing element 1910 to align the front plunger port 2066 with the reservoir port 1908.

The interface device 1902 includes a transfer member locking element, e.g., plunger assembly locking element 1918 at seal plate 1944 (FIG. 19A), to prevent movement of the front plunger port 2066 (FIG. 20A) of the transfer device away from the reservoir port 1908 when the sealing element is in the open position. The plunger assembly locking element 1918 includes ramps 1920 (FIGS. 22L and 22T) to engage slots 2086 (FIGS. 20A and 22T) of the plunger assembly 2064. Once the plunger assembly 2064 has been inserted into the interface device 1902 and moved vertically to align with the reservoir port 1908, the ramps 1920 engage the slots 2086 and keep the plunger assembly 2064 from being pulled out of the interface device 1902, as is further described in reference to FIG. 22L.

Returning to FIG. 20A, the plunger assembly 2064 includes a valve member 2068 that is movable between an open position and a closed position to control flow of fluid through the front plunger port 2066. The inner plunger 2070 is slidably disposed in the outer plunger 2072 and in bore 2074 of outer tube 2073. The inner plunger, which is slidable relative to outer plunger 2072 and outer tube 2073, is operable to move the valve member 2068 between the open and closed positions. As shown, the front plunger port 2066 is provided at the front of the outer plunger 2072. The outer plunger 2072 is slidably disposed in bore 2061 of the body 2060 of the transfer device 2004. The outer plunger 2072 is configured to extend through the coupling members 2025 and 1924 (FIG. 19A) and into the interface device 1902, as will be described below. The system 2100, including interface device 1902 and transfer device 2004, is configured to provide an air gap between the outer plunger 2072 and the coupling elements to minimize exposure of the outer and inner plungers to non-sterile or 'dirty' surfaces, e.g., the mating faces 1932 and 2033 of the coupling elements 1924 and 2025. The outer plunger 2072 (including outer tube 2073) is configured to cooperate with the inner plunger 2070 to provide a fluid path for the transfer of fluid. The inner plunger 2070 is configured to cooperate with the outer plunger 2072 to provide valving.

As shown in FIG. 20A, the transfer device 2004 includes guide 2076 to limit movement of the outer plunger 2072 and outer tube or handle mount 2073 relative to the guide element 2075. In the embodiment shown, the guide comprises a slot that cooperates with a pin to limit length of travel and to limit or prevent rotation. As shown, the guide 2076 includes a slot in the guide element 2075 that cooperates with a tab 2099 on the outer tube 2073. The slot of the guide element 2075 limits travel and prevents rotation of the pin 2099 in the slot, thereby limiting travel and preventing rotation of the outer tube 2073 relative to the body 2060.

The transfer device 2004 can maintain a sterile path for the fluid being transferred. To that end, the transfer device 2004 includes one or more seals configured to provide a sterile barrier between the fluid path and the environment. As shown in FIG. 20A, the transfer device 2004 includes seals 2090, 2092 and 2094, which, in this embodiment, are O-rings. The inner plunger 2070 includes respective grooves (channels) 2091 and 2093 to seat seals 2090 and 2092. The housing 2060 includes a groove (channel) 2095 (FIG. 22A) to the seal 2094. Additional seals may be provided as described herein.

FIGS. 21A-21F are top views of the system 2100 including the interface device 1902 of FIG. 19A and the transfer device 2004 of FIG. 20A illustrating the process of operating the system 2100, e.g., to transfer fluid into or out of a reservoir as described herein. FIGS. 22A-22U are sectional views of the devices of FIG. 19A and FIG. 20A corresponding to the top views of FIGS. 21A-21F.

In FIGS. 21A and 22A, the interface device 1902 and transfer device 2004 of the system 2100 are shown in uncoupled and closed positions. The reservoir valve (i.e., sliding seal) 1910 is in the closed position sealing the reservoir port 1908. As shown, the hole 1911 of the sliding seal 1910 is out of alignment with the reservoir port 1908 to close the reservoir port. The sealing element 1910 and the mounting plate 1906 can define a steam cleanable surface 2102 that is exposed to the inside of the reservoir when the sealing element is in the closed position.

Figure 21B:
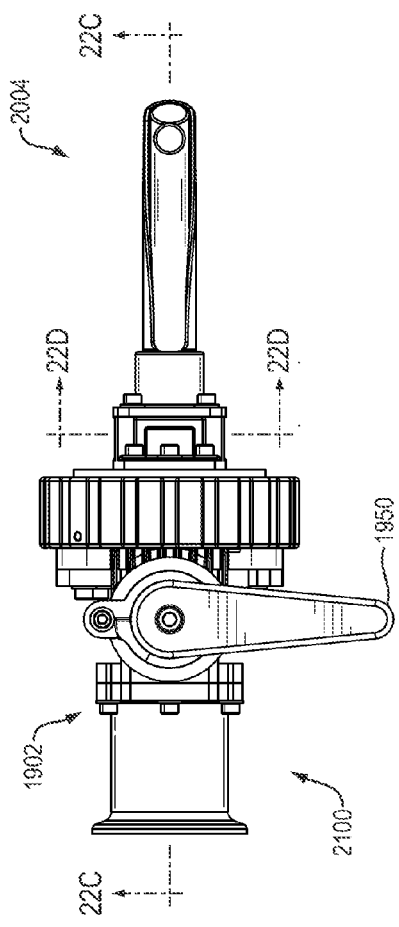
Figure 22C:
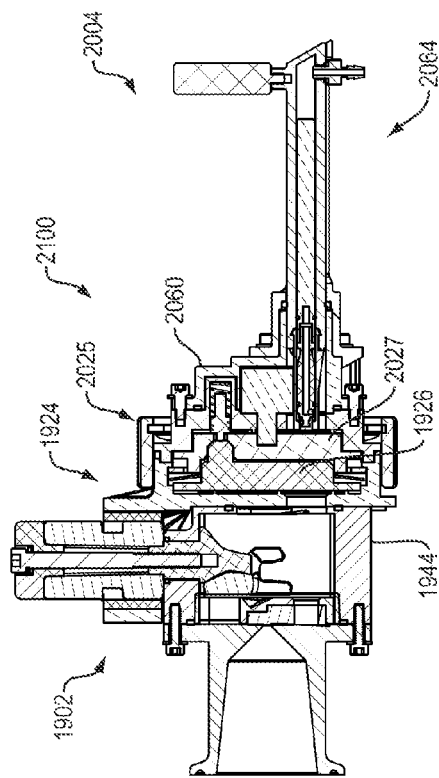
FIG. 22C is sectional view of the system of FIG. 21B.
Figure 22D:
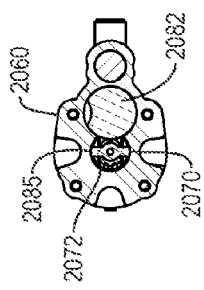
FIG. 22D is a sectional view of the transfer device of the system of FIG. 21B.

As shown in FIGS. 21B and 22C, the fluid transfer member of the transfer device 2004, i.e. the plunger assembly 2064, has been aligned with the interface device 1902. The transfer coupling member 2025 of the transfer device 2004 is coupled to the interface coupling member 1924 of the interface device 1902. The mating faces 1932 and 2033 (FIGS. 21A and 22A) of the discs 1926 and 2027 butt against each other and the discs are rotationally coupled. The discs, however, have not been rotated and their openings 1928, 2029 (FIGS. 19A and 20A) are not aligned with the transfer device 2004 or the interface device 1902. Thus, there is no passage through the coupling members 1924 and 2025 to receive the transfer member, i.e., the plunger assembly 2064. The fluid transfer member receptacle of the interface device 1902, i.e. the seal plate 1944, is closed, as is the body 1660 of the transfer device 1604.

The alignment and rotation of the discs 1926 and 2027 of the coupling members 1924 and 2025, respectively, is similar to that of discs 126 and 127 described above in reference to FIGS. 4A-C and 5A-C. However, the coupling members in this embodiment include respective disc locking members to prevent rotation of the discs until the discs are coupled to each other and the disc locking members are released. As shown in FIGS. 20A and 22A, the disc locking member of the transfer device 2004 includes a pin 2058 that is biased by a spring 2059 into a hole 2132 (FIG. 22A) of disc 2027 to prevent rotation of the disc 2027 relative to the housing 2031. The spring-loaded pin 2058 is displaceable by a boss or pin 2130 protruding from the mating face 1932 of the interface coupling member 1926 (see also FIG. 19B). As shown in FIG. 19A, the disc locking member of the interface device 1902 includes a pin 1958 that is biased by a spring 1959 into a hole 2136 (see FIGS. 19A, 19H) of the disc 1926 to prevent rotation of the disc 1926 relative to housing 1930. The spring-loaded pin 1958 is displaceable by a boss 2134 (see FIGS. 20A, 20H) protruding from the mating face 2033 of the transfer coupling member 2027. Thus, when coupled together, the interface coupling member 1924 releases the disc locking member of the transfer device 2004 and the transfer coupling member 2025 releases the disc locking member of the interface device 1902. This safety feature prevents accidental rotation of either of the discs 1926 and 2027, thereby preventing unwanted opening of the transfer device or the interface device.

Figure 21C:
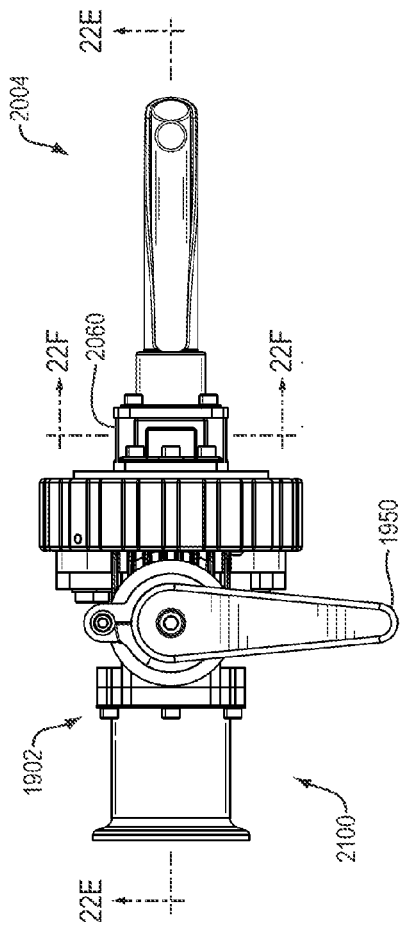
Figure 22E:
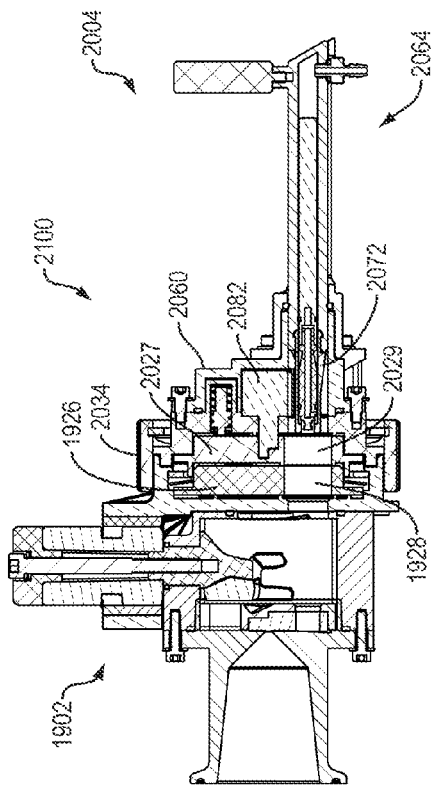
FIG. 22E is sectional view of the system of FIG. 21C.

In FIGS. 21C and 22E, the openings in the discs 1926 and 2027 are aligned with the transfer member, i.e., plunger assembly 2064. The discs 1926 and 2027, which are rotationally coupled, are rotated using collar 2034 to bring the respective openings 1928 and 2029 into alignment with the fluid transfer member receptacle 1944 and the fluid transfer member 2064, thereby creating a passage through which the fluid transfer member can be extended. The outer plunger 2072 (including outer tube 2073) is configured to extend through the openings 1928 and 2029, preferably without contacting the respective discs 1926 and 2027 of coupling members 1924 and 2025, whose mating surfaces 1932 and 2033 were exposed to the environment prior to coupling the devices. As shown in FIG. 22S, the system 2100 is configured to maintain an air gap 2108 when the outer plunger 2072 and outer tube 2073 are extended through the openings 1928 and 2029, the air gap separating the outer plunger 2072 and outer tube 2073 from the discs 1926 and 2027 of respective coupling members 1924 and 2025. The purpose of the air gap is to avoid contact with potentially contaminated surfaces.

Figure 22F:
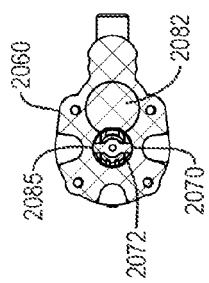
FIG. 22F is a sectional view of the transfer device of the system of FIG. 21C.
Figure 22J:
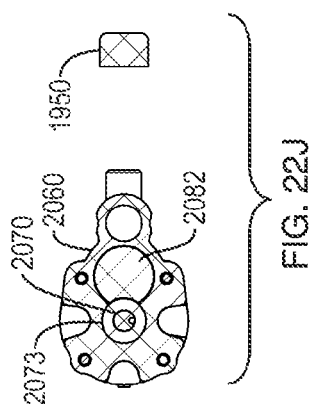
Figure 22U:
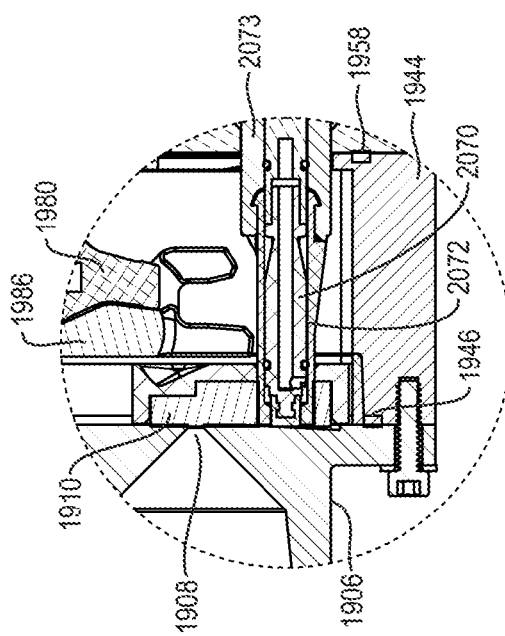
FIG. 22U is an expanded view of the reservoir port and front plunger port of the system of FIG. 22G.

Similar to transfer device 1604 described above, the transfer device 2004 includes a plunger locking element or interlock 2082. The interlock 2082 prevents the operator from advancing the transfer member, e.g., the outer plunger 2072, relative to the body 2060 and toward the disc 2027 of the transfer coupling element when the transfer device 2004 is not coupled to the interface device and when the disc 2027 has not been rotated to align the opening 2029 with the bore of the transfer device. As shown in FIGS. 20A and 22B, the plunger interlock 2081 is a cylindrical element that has a longitudinal cutout or groove 2081 and that is seated in the body 2060 of the transfer device 2004. The plunger interlock 2082 is rotationally coupled to disc 2027 via a keyed rod (see, e.g., FIGS. 20A and 22E). In the locked state (see FIGS. 22A and 22B), the cutout 2081 is out of alignment with the outer plunger 2072 and the interlock 2082 partially blocks the bore 2061 of the transfer device. When the disc 2027 is rotated to align the opening 2029 with the transfer member, the interlock 2082 rotates with the disc, thereby aligning the cutout 2081 of interlock 2082 with the outer plunger 2072 and the bore 2061 to allow the outer plunger to pass by the interlock (FIGS. 22E and 22F).

Figure 22G:
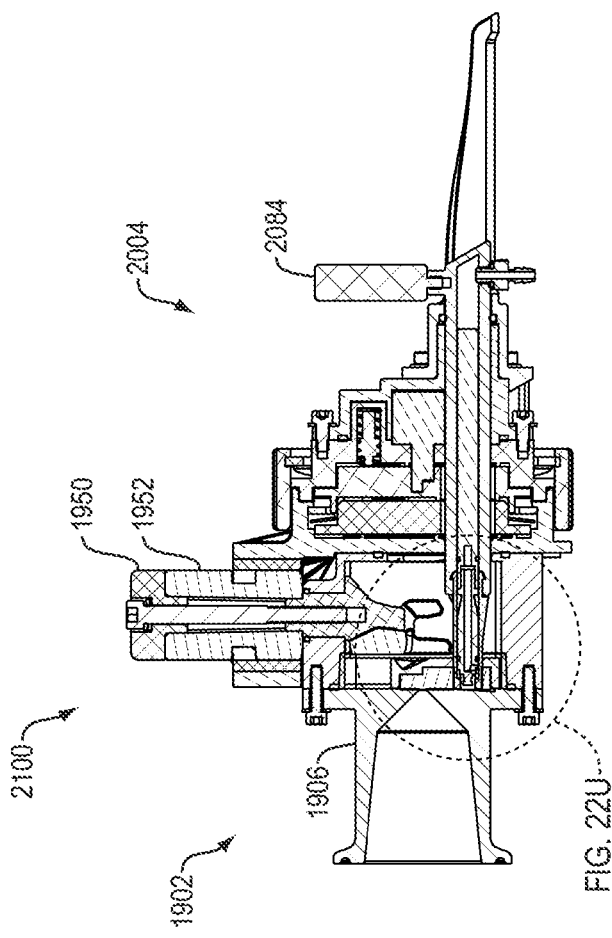

In FIG. 21D and corresponding section views in FIGS. 22G and 22S, the inner and outer plungers 2070 and 2072 have been advanced into the interface device 1902 by pushing the handle 2084 toward the interface device 1902. FIG. 22U is an expanded view of the reservoir port and front plunger port of the system of FIG. 22G. As shown, the inner and outer plungers 2070 and 2072 extend through the hole 1911 of the sliding seal 1910.

Figure 21E:
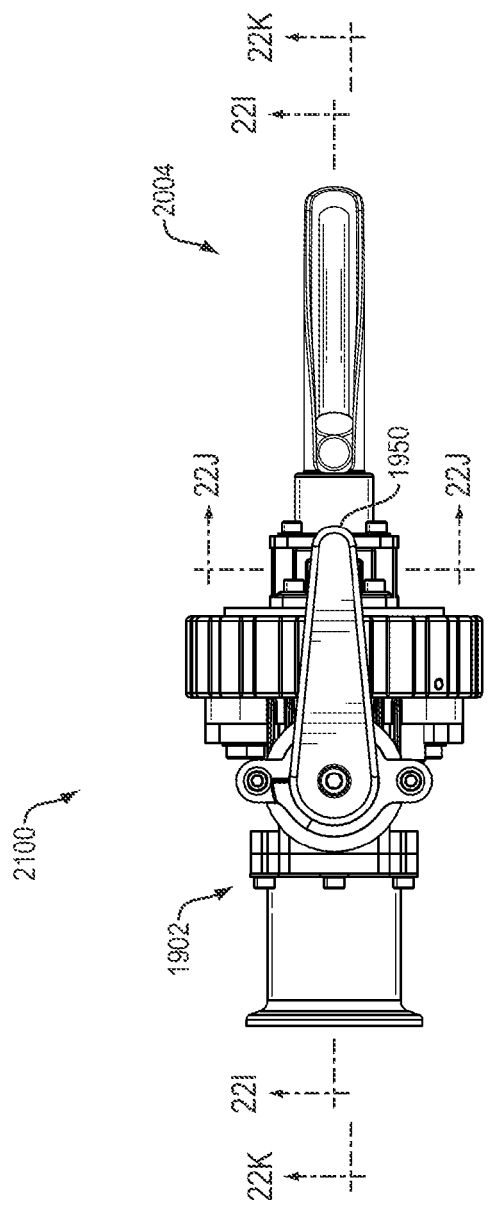

In FIG. 21E and corresponding sectional views in FIGS. 22I and 22K, the reservoir valve, i.e. sliding seal, 1910 is actuated. With the inner and outer plungers 2070 and 2072 positioned in the fluid transfer member receptacle 1944, the reservoir valve 1910 is actuated to open the reservoir port 1908 to the fluid transfer member receptacle 1944. In this embodiment, the valve is actuated by sliding the sliding seal 1910 linearly using actuating mechanism 1948. An operator can turn the axial cam 1952 via handle 1950 to move the housing 1930 up relative to the seal plate 1944. In the example shown, a 90 degree turn in counter-clockwise direction moves the housing up to the appropriate height to align the inner and outer plungers of the transfer device 2004 with the reservoir port 1908. Because the housing 1930 has been coupled to the transfer device 2004 via coupling members 1925 and 2026, moving the housing 1930 moves the transfer device 2004 including in the inner and outer plungers 2070 and 2072. The plunger 2072 drives the sliding seal 1910 up to align hole 1911, and the inner and outer plungers 2070 and 2072 extending therethrough, with the reservoir port 1908. Although hole 1911 is now aligned with the reservoir port 1908, the seal 2068 of the plunger assembly 1664 seals the reservoir port 1908. As shown, the seal 2068 is positioned at the front end of inner plunger 2070 and within the outer plunger 2072 (see also FIG. 22Q).

When the outer plunger 2072 (including outer tube 2073) is driven up by the actuation mechanism 1948, the transfer member locking element 1918 retains the outer plunger 2072 of the transfer member in position, as shown in FIGS. 22K and 22L. As the outer plunger 2072 (including outer tube 2073) is pushed up, the slots 2086 ride against ramps 1920 of the locking element 1918. The ramps 1920 push the slots 2086, and hence the outer plunger 2072, forward into the sealing element 1910 and against the reservoir port 1908. This preloads the outer plunger 2072 against the sealing element 1910 and the reservoir port 1908 to ensure a tight seal. This also reduces the amount of fluid that could build up in front of the front plunger port 2066 of the plunger assembly. When the reservoir port 1908 is open, the ramps 1920 of the transfer member locking element 1918 retain the outer plunger 2072 in position in the fluid transfer member receptacle, i.e., seal plate 1944, of the interface device 1902. This feature prevents accidental withdrawal of the outer plunger 2072, e.g., through operator error, and contributes to maintaining integrity of the fluid path during the transfer of fluid.

As illustrated in FIGS. 22K and 22L, when the outer plunger 2072 (including outer tube 2073) is driven up, the ears 2085 of the inner plunger 2070 engage the yoke 1986. Because the inner plunger 2070 is now movably coupled to the yoke 1986, an operator can use handle 1950 to rotate rotary cam 1980 to drive the yoke 1986 to move the inner plunger 2070 away from the reservoir port, as will be described below. In FIGS. 22K and 22L, the inner plunger 2070 has not yet been moved away from the reservoir port 1908 and the reservoir port and the front plunger port 2066 are closed, as can be more clearly seen in FIG. 22Q, which is an expanded view of the reservoir port 1908 and front plunger port 2066 of FIG. 22K.

The actuating mechanism 1948 includes an actuation handle 1950, an axial cam 1952 for vertical motion, and a rotary cam 1980 for horizontal motion (see FIGS. 19A and 22G). The handle and the cams are fastened together, e.g., with a screw 1949, as shown, or other suitable means, such that rotation of the handle causes rotation of both cams. The axial cam 1952 includes a thread 1953*a*. A tooth (e.g., cam follower) of cam insert 1951 rides in the thread, such that rotation of the axial cam causes the cam insert to move up or down along the cam with rotation of the cam. The cam 1952 also has a horizontal groove 1953*b* at the upper end of the thread 1953*a*. The tooth of the cam insert 1951 stays put when in the horizontal groove 1953*b*. In this way, rotation of the cam when the tooth is in the horizontal groove 1953*b* does not cause the cam insert to move vertically. The rotary cam 1980 includes an upper surface 1982 and a lower surface 1984. The surfaces are configured to interface with corresponding upper and lower surfaces on the yoke 1986 to drive the yoke.

Initially, as for example shown in FIGS. 19A, 21A and 22A, the handle 1950 of the actuating mechanism, and hence the cams, are at 0 degree of rotation. In a first motion, when the handle 1950 and cams 1952 and 1980 are rotated from 0 to 90 degrees, the axial cam 1952 moves the body (housing) 1930 up via action of the cam follower of the cam insert 1951 (see, e.g., FIGS. 21E and 22I). As the body 1930 moves up, so does the plunger assembly, and the ears 2085 of the inner plunger 2070 are moved into position between the legs 1988 of the yoke 1986 (see FIG. 22L). Both upper and lower surfaces of the rotary cam 1980 are shaped and configured to not push on the yoke 1986 as the rotary cam rotates from 0 to 90 degrees. In a second motion, when the handle 1950 and cams 1952 and 1980 are rotated from 90 to 180 degrees (see, e.g., FIGS. 21F and 22M), the horizontal groove 1953*b* (FIG. 19A) at the end of the thread 1953*a* causes the cam follower of insert 1951, and hence body 1930, to stay put. The upper surface 1982 of the rotary cam, however, pushes the yoke 1986 above the pivot 1990 (FIG. 19A) causing the legs 1988 of the yoke to swing away from the reservoir port 1908 (see, e.g., FIGS. 22O and 22P). The legs, which grab ears 2085 of the inner plunger, drive the ears away from the reservoir port 1905, thereby pulling the inner plunger 1970 away from the reservoir port, thereby opening the front plunger port 2066 and the reservoir port 1908.

Thus, during a first rotary motion, e.g., rotation from 0 to 90 degrees in one direction, or 90 to 0 degrees in the opposite direction, the rotary cam 1980 dwells, that is the cam rotates but the surfaces of the rotary cam to not drive the chair-shaped yoke 1986. During a second rotary motion, e.g., rotation between 90 and 180 degrees, the upper cam surface 1982 pushes on the yoke 1986 above the pivot 1990 (FIG. 19A) when the rotation is in one direction (e.g., from 90 to 180 degrees), while the lower cam surface 1984 pushes on the yoke 1986 below the pivot when the rotation is in the opposite direction (e.g., from 180 to 90 degrees). The yoke 1986 is not free to pivot during the second rotary motion of the cam. The rotary cam 1980 of the actuating mechanism is configured to positively drive the yoke 1986, both to move the inner plunger 1970 to open the reservoir port 1908 (and the front plunger port 2066) and to move the inner plunger to close the reservoir port (and the front plunger port).

In FIG. 21F and corresponding sectional views in FIGS. 22M and 22O, the inner plunger 2070 is moved away from the reservoir port 1908 and the reservoir port is opened. As described above, an operator can turn handle 1950 to move the inner plunger 2070 away from the reservoir port 1908, thereby moving the seal 2068 away from the reservoir port, which opens the reservoir port. Opening the reservoir port 1908 with the inner plunger 2070 provides a fluid path from the reservoir port 1908 to the transfer port 2062 as described below in reference to FIG. 22R.

FIG. 22R is an expanded view of the reservoir port 1908 and front plunger port 2066 of FIG. 22M showing the opened reservoir port and front plunger port. The seal 2068 is similar to and functions in the same manner as seal 1668 described above in reference to FIG. 18L. The seal 2068 is a valve member that cooperates with a valve seat of the mounting plate 1906 of the interface device to open and close the reservoir port 1908. In addition, the seal 2068 and the outer plunger 2072 also form a valve to open and close the front plunger port 2066 of the plunger assembly 2064. As shown, the seal 2068 is also a valve member that cooperates with a valve seat of the outer plunger 2072. The seal 2068 forms a radial, shear seal with the valve seat of the outer plunger. The shear seal can avoid particles, e.g., platelets, to get caught in the valve member and the valve seat. Moving the seal 2068 away from the reservoir port 1908 (and out of the valve seat) opens the front plunger port 2068, thereby allowing flow of fluid through the fluid path. Fluid can now flow from the reservoir port 1908 to the transfer port 2062 (FIG. 22M), or vice versa, through a channel (e.g., bore) 2110 in inner plunger 2070 that is in fluid communication with channel 2111 (FIG. 22N) defined by the inner plunger 2070 and outer tube 2073. In this example, channel 2111 comprises a channel or groove along a length of the inner plunger 2070 that provides a space for fluid flow between the inner plunger 2070 and an inside of the outer tube 2073, similar to channel 1710 illustrated in FIG. 18L.

FIG. 22R shows the seals or O-rings 2090 and 2092 of the inner plunger 2070 which contribute to the maintenance of a sterile fluid path. The O-rings can be spaced apart far enough to prevent over-wipe when the inner plunger 2070 moves with respect the outer plunger 2072 and outer tube 2073.

Once the transfer of fluid is complete, the inner plunger 2070 can be pushed back towards the reservoir port 1908 to stop the flow of fluid through the front plunger port 2066 and to seal the reservoir port with seal 2068. This is the reverse operation of opening the front plunger port, and a user simply has to rotate the actuation handle 1950 by 90 degrees in a clockwise direction. The reservoir valve 1910 can then be actuated to close the reservoir port from the fluid transfer receptacle 1944 by moving the sliding seal 1910 down using actuating mechanism 1948. This can be accomplished by a further 90 degrees turn of the actuation handle 1950. The plunger assembly 2064 can be withdrawn from the fluid transfer member receptacle and the interface device 1902. Once the plunger assembly 2064 is withdrawn, the discs 1926 and 2027 can be rotated back to close both the fluid transfer member receptacle 1944 of the interface device and the body 2060 of the transfer device.

The devices described herein, e.g., the interface devices 102, 1502 and 1902, and the transfer devices 104, 1604 and 2004, may be formed of metal or plastic. Preferably, the transfer device is formed of a plastic material and may be formed by machining the respective components and then applying the necessary seals and the like, or by molding the respective components separately and assembling them together with the necessary seals and other components.

The devices described herein may be made of any material capable of some type of sterilization, such as steam, pressurized steam, chemical or radiation. Preferably, the entire device is made of the same material and is capable of withstanding the selected sterilizing conditions. Suitable materials for the devices described herein include, but are not limited to, polyolefins such as polyethylene or polypropylene, polycarbonates, polystyrenes, EVA copolymers, polyvinyl chlorides, PVDF, PTFE, thermoplastic fluoropolymers such as PFA and PTFE, PEI (polyetherimide), PEEK, PEK, polysulphones, polyarlysulphones, polyalkoxysulphones, polyethersulphones, polyphenyleneoxide, polyphenylenesulphide and blends thereof, as well as thermosets such as epoxies, urethanes, cyanurates and the like.

The seals of embodiments of the present invention, which may be in the form of O-rings, gaskets, plug seals, and the like, can be made of a variety of materials typically used for making resilient seals. These materials include, but are not limited to, natural rubber, synthetic rubbers, such as silicone rubbers, including room temperature vulcanizable silicone rubbers, catalyzed (such as by platinum catalysts) silicone rubbers and the like, thermoplastic elastomers such as SANTOPRENE®, elastomers, polyolefins such as polyethylene or polypropylene, especially those containing gas bubbles introduced either by a blowing agent or entrained gas such as carbon dioxide, PTFE resin, thermoplastic perfluoropolymer resins such as PFA and MFA resins (available from Ausimont, USA of Thorofare, N.J. and E.I. DuPont de Nemours of Wilmington, Del.), urethanes, especially closed cell foam urethanes, KYNAR® PVDF resin, VITON® elastomer, EPDM rubber, KALREZ resin and blends of the above. Suitable materials for molded in place seals can be curable rubbers, such as room temperature vulcanizable silicone rubbers, thermoplastic elastomers such as SANTOPRENE® elastomers, polyolefins such as polyethylene or polypropylene, especially those containing gas bubbles introduced either by a blowing agent or entrained gas such as carbon dioxide and elastomeric fluoropolymers Other materials used in the devices are preferably also FDA grade components such as FDA grade rubbers and silicones, PTFE resins and the like.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims. It should also be appreciated that the various technical features of the devices that have been described may be combined in various ways to produce numerous additional embodiments.

What is claimed is:

1. A transfer device comprising:
a body having a bore therethrough;
a coupling member configured to close the body and to couple to an interface device and open the body to the interface device; and
a transfer member slidably disposed in the bore of the body, the transfer member configured to extend through the coupling member and cooperate with the interface device to open a reservoir port of the interface device,
the coupling member comprising a disc, the disc having an opening to receive the transfer member, the disc being configured for rotation to bring the opening into alignment with the bore to permit the transfer member to extend through the opening into the interface device, the axis of rotation of the disc being parallel to the bore of the body.

2. The device of claim 1, wherein the disc is configured to couple to a collar to cause rotation of the disc with rotation of the collar.

3. The device of claim 1, wherein the disc includes a mating face configured to rotationally couple the disc to a corresponding disc of the interface device, such that the discs rotate together.

4. The device of claim 1, wherein the transfer member comprises a plunger assembly.

5. The device of claim 1 further comprising one or more seals configured to provide a sterile barrier between the environment and a fluid path from the reservoir port to a transfer port, the transfer device maintaining a sterile path for fluid being transferred through the fluid path.

6. The device of claim 1, further comprising an interlock configured for rotation with the disc of the coupling member, the interlock preventing the transfer member from extending toward the coupling member until the opening in the disc is aligned with the bore of the body.

* * * * *